US012622965B2

(12) United States Patent
Nelidova et al.

(10) Patent No.: US 12,622,965 B2
(45) Date of Patent: May 12, 2026

(54) THERAPEUTICAL TOOLS AND METHODS USING TEMPERATURE-SENSITIVE RECEPTORS FOR TREATING BLINDNESS

(71) Applicants: FRIEDRICH MIESCHER INSTITUTE FOR BIOMEDICAL RESEARCH, Basel (CH); INSTITUTE OF MOLECULAR AND CLINICAL OPHTHALMOLOGY BASEL, Basel (CH)

(72) Inventors: Dasha Nelidova, Basel (CH); Botond Roska, Basel (CH)

(73) Assignees: FRIEDRICH MIESCHER INSTITUTE FOR BIOMEDICAL RESEARCH, Basel (CH); INSTITUTE OF MOLECULAR AND CLINICAL OPHTHALMOLOGY BASEL, Basel (CH)

( * ) Notice: Subject to any disclaimer, the term of this patent is extended or adjusted under 35 U.S.C. 154(b) by 780 days.

(21) Appl. No.: 17/904,462

(22) PCT Filed: Feb. 18, 2021

(86) PCT No.: PCT/IB2021/051384
§ 371 (c)(1),
(2) Date: Aug. 17, 2022

(87) PCT Pub. No.: WO2021/165876
PCT Pub. Date: Aug. 26, 2021

(65) Prior Publication Data
US 2023/0103783 A1      Apr. 6, 2023

(30) Foreign Application Priority Data
Feb. 19, 2020     (EP) ..................................... 20158285

(51) Int. Cl.
| | |
|---|---|
| *A61K 41/00* | (2020.01) |
| *A61K 47/68* | (2017.01) |
| *A61K 47/69* | (2017.01) |
| *A61P 27/02* | (2006.01) |
| *B82Y 5/00* | (2011.01) |
| *C07K 14/46* | (2006.01) |
| *C07K 14/705* | (2006.01) |
| *C12N 15/86* | (2006.01) |

(52) U.S. Cl.
CPC ...... *A61K 41/0052* (2013.01); *A61K 47/6849* (2017.08); *A61K 47/6923* (2017.08); *A61K 47/6929* (2017.08); *A61K 47/6931* (2017.08); *A61P 27/02* (2018.01); *C12N 15/86* (2013.01); *B82Y 5/00* (2013.01); *C07K 14/46* (2013.01); *C07K 14/705* (2013.01); *C07K 2319/21* (2013.01); *C07K 2319/40* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| | | | | |
|---|---|---|---|---|
| 2011/0021541 A1* | 1/2011 | White | ..................... | A61P 19/08 514/263.21 |
| 2012/0245144 A1* | 9/2012 | Heffron | ..................... | A61P 5/00 514/211.1 |
| 2017/0003279 A1* | 1/2017 | Nesterov | ........... | G01N 33/5041 |

FOREIGN PATENT DOCUMENTS

| | | |
|---|---|---|
| EP | 3 437 473 A1 | 2/2019 |
| WO | WO 2008/022772 | 2/2008 |
| WO | WO 2008/022772 A1 | 2/2008 |
| WO | WO 2011/105886 A1 | 9/2011 |
| WO | WO 2013/029025 A1 | 2/2013 |

OTHER PUBLICATIONS

Sanchez-Rodriguez et al. Biotechnology and Bioengineering 2016, vol. 113, No. 10, pp. 2228-2240.*
Calado et al., Tissue Engineering Part A 2014, vol. 20, pp. 2692-2698.*
Bálya, et al. "Retina model with real time implementation" 2005 IEEE International Symposium on Circuits and Systems, Kobe, Japan, 5, pp. 5222-5225, (2005).
Joshi, et al., "Conjugation of Antibodies to Gold Nanorods through Fc Portion: Synthesis and Molecular Specific Imaging", *Bioconjug Chem*, 24(6), pp. 878-888, (2013).
Jüttner et al., "Targeting neuronal and glial cell types with synthetic promoter AAVs in mice, non-human primates and humans", Nature Neuroscience, 22(8), pp. 1345-1356, (2019).
Lakk, et al., "Polymodal TRPV1 and TRPV4 Sensors Colocalize but Do Not Functionally Interact in a Subpopulation of Mouse Retinal Ganglion Cells", *Front Cell Neurosci*, 12, p. 353, (2018).
Qin, et al., "Thermophysical and biological responses of gold nanoparticle laser heating", *Chem Soc Rev*, 41, pp. 1191-1217, (2012).
Ryskamp, et al., "TRPV1 and Endocannabinoids: Emerging Molecular Signals that Modulate Mammalian Vision", *Cells*, 3(3), pp. 914-938, (2014).
Stanley, et al., "Radio-Wave Heating of Iron Oxide Nanoparticles Can Regulate Plasma Glucose in Mice", Science, 336(6081), pp. 604-608, (2012).
Bi et al., "Ectopic Expression of a Microbial-Type Rhodopsin Restores Visual Responses in Mice with Photoreceptor Degeneration," Neuron., vol. 50, No. 1, p. 23-33, (2006).
Carvalho-De-Souza et al., "Photosensitivity of Neurons Enabled by Cell-targeted Gold Nanoparticles," Neuron. vol. 86, No. 1, p. 207-217, (2015).

(Continued)

*Primary Examiner* — Tracy Vivlemore
(74) *Attorney, Agent, or Firm* — Hoxie & Associates LLC

(57) ABSTRACT
The present inventions relates to a method for vision restoration comprising the steps of expressing a temperature-sensitive transient receptor potential (TRP) channel having an extracellular tag in the retina of a subject and of contacting said retina with a nanomaterial conjugated to a molecule specifically binding to said extracellular tag, wherein said nanomaterial generates heat by absorbing radiations of a specific wavelength. And reagents therefor.

10 Claims, 4 Drawing Sheets
Specification includes a Sequence Listing.

(56)  References Cited

OTHER PUBLICATIONS

Lyu et al., "Semiconducting Polymer Nanobioconjugates for Targeted Photothermal Activation of Neurons," Journal of the American Chemical Society, vol. 138, No. 29, p. 9049-9052, (2016); Abstract Only.

Ma et al., "Mammalian Near-Infrared Image Vision through Injectable and Self-Powered Retinal Nanoantennae," Cell vol. 177, p. 243-255, (2019).

Nelidova et al., "Restoring Light Sensitivity Using Tunable Near-Infrared Sensors," Science, vol. 368, No. 6495, p. 1108-1113, (2020); Abstract Only.

Sanchez-Rodriguez et al., "Plasmonic Activation of Gold Nanorods for Remote Stimulation of Calcium Signaling and Protein Expression in HEK 293T Cells: Nanoparticle-Driven Cell Activation," Biotechnology and Engineering, vol. 113, No. 10, p. 2228-2240, (2016); Abstract Only.

Zhu et al., "Mouse Cone Arrestin Gene Characterization: Promoter Targets Expression to Cone Photoreceptors," FEBS Letters, vol. 524, No. 1-3, (2002).

* cited by examiner

THERAPEUTICAL TOOLS AND METHODS USING TEMPERATURE-SENSITIVE RECEPTORS FOR TREATING BLINDNESS

CROSS-REFERENCE TO RELATED APPLICATIONS

This application is a U.S. National Stage Application under 35 U.S.C. § 371 of International Application No. PCT/IB2021/051384, filed on Feb. 18, 2021, which claims priority to, and the benefit of, European application No. 20158285.5, filed on Feb. 19, 2020, the contents of each of which are hereby incorporated by reference in their entireties.

FIELD OF THE INVENTION

The present invention relates to methods of treating blindness using temperature sensitive receptors. The present invention also relates to reagents for use in treating blindness, as well as their use in the manufacture of a medicament for treating blindness.

BACKGROUND OF THE INVENTION

Blindness is a major health problem that disables millions of people worldwide. The most common cause of blindness is the disfunction of the retina. The three most common forms of retinal blindness are retinitis pigmentosa (RP), macular degeneration (MD) and glaucoma (G). In RP and MD the primary problem is the degeneration of photoreceptors and the consequent loss of photosensitivity. There is thus a need to be able to obviate the problems associated with such degeneration of photoreceptors.

One approach has been to develop a retinal prosthesis, a "seeing eye" chip with as many as 1,000 tiny electrodes to be implanted in the eye. This would have the potential to help people who have lost their sight to regain enough vision to function independently, but the numbers of electrodes is simply insufficient to provide a high degree or level of sight to be obtained. Moreover, there are problems associated with inserting foreign bodies into the eye.

Recently a number of genes has been isolated and/or manipulated that when expressed can make cells light sensitive. In some cases additional non-genetic factors are also needed to make cells light sensitive.

This is complex and problems are likely to arise if the channel is delivered to the wrong type of retinal cell.

Bi et al., (Neuron, 50, 2006, p 23-33) discloses the use of microbial-type rhodopsin to restore visual responses in mice with photoreceptor degeneration. However, the expression of the rhodopsin gene is likely to have occurred in a variety of types of cell in the eye which is potentially undesirable and/or problematic. It also appears that the threshold light intensity required for producing responses is much higher than for normal rod and cone photoreceptors, but there is no teaching of how this may be addressed in, for example, low light environments.

An alternative method has been described by some of the present inventors in WO-A-2008/022772, wherein e.g. channelrhodopsin-2 is targeted to e.g. ON-cells. This method has however the disadvantage of being sub-optimal with OFF-cells.

Enabling the detection of near-infrared (NIR) light at wavelengths (>900 nm) far away from the human visible spectrum (390-700 nm) could provide a way of supplementing or restoring vision in affected retinal regions, without interfering with remaining vision. Upconversion nanoparticles applied to the eye allow the perception of NIR light after conversion of NIR back to visible light (Cell 177, 243-255 e215 (2019).). However, they rely on functional photoreceptors. Photoreceptor dysfunction rules out upconversion as a technology to enable NIR light detection in the blind retina.

It is amongst the objects of the present invention to obviate and/or mitigate at least one of the aforementioned disadvantages.

SUMMARY OF THE INVENTION

To address this need, the present inventors considered the use of temperature-sensitive transient receptor potential (TRP) channels. A few species such as boas, pythons and pit vipers can detect infrared light (1-30 μm) using temperature sensitive TRP channels expressed in a specialized organ (Nature 464, 1006-1011 (2010)). Thermal and visual images superimpose within the snake's brain, presumably enabling the snake to react to the environment with greater precision than with use of a single image only (Science 213, 789-791 (1981)). In order to restore vision, TRP channels could potentially be targeted to retinal cell types, as they are sensitive to infrared radiation. However, heat transfer to ectopically-expressed TRP channels via direct near-infrared illumination is inefficient, and requires high intensities that would damage the retina.

In order to develop a more efficient, NIR detector for retinal cell types, the present inventors engineered a two-component system consisting of a genetic and a nanomaterial component. The genetic component consisted of temperature sensitive TRP channels, engineered to incorporate an extracellular epitope recognizable by a specific antibody (Science 336, 604-608 (2012)). The nanomaterial component consisted of gold nanorods conjugated to an antibody against this epitope (Bioconjug Chem 24, 878-888 (2013)). This system uses surface plasmon resonance for heat transfer (Chem Soc Rev 41, 1191-1217 (2012)): gold nanorods capture NIR light at a pre-specified wavelength and use the energy to produce heat and open temperature-sensitive TRP channels in the proximity of the nanorods. Another advantage of this system is that the epitope can be engineered to ensure the specificity of antibody binding to engineered TRP channels since some TRP channels, such as TRPV1, are naturally expressed in the retina (Front Cell Neurosci 12, 353 (2018); Cells 3, 914-938 (2014).). Finally, this system proved to be so versatile, that it can be tailored to respond to any wavelength by varying the physical properties of the nanomaterial.

There is provided a novel approach to restore, or improve, visual function in a blind or vision impaired retina, designed to be compatible with remaining vision, by employing gold nanorods that are coupled to temperature-sensitive engineered TRP channels. These constructs are found to be able to induce NIR light sensitivity in remaining photoreceptor cell bodies of blind mice and in ex vivo human retinas. In mice, NIR light-sensitized photoreceptors activate cortical visual circuits and enable behavioral responses. By means of distinct nanorod and TRP channel types, NIR vision can be tuned to different wavelengths and to different radiant powers. In the human retina, reactivation of light responses in photoreceptors, and their retinal circuits can be observed even eight weeks post-mortem.

The present invention therefore encompasses an isolated nucleic acid molecule comprising a nucleotide sequence coding for a temperature-sensitive transient receptor potential (TRP) channel having an extracellular tag, for use in a method for vision restoration comprising the steps of expressing said temperature-sensitive TRP channel having an extracellular tag in the retina of a subject and of contacting said retina with a nanomaterial conjugated to a molecule specifically binding to said extracellular tag, wherein said nanomaterial generates heat by absorbing radiations of a specific wavelength, wherein said isolated nucleic acid molecule further comprises a promoter operatively linked to said temperature-sensitive TRP channel having an extracellular tag and leading to the specific expression of said temperature-sensitive TRP channel having an extracellular tag in at least one specific cell population of said retina. There is a large variety of known temperature-sensitive TRP channel suitable for the invention, and the temperature-sensitive TRP channel can, for instance, be selected from the group comprising TRPM, TRPA, and TRPV, for instance TRPV1 or TRPA1, and homologs thereof. Similarly, the skill person knows a plurality of tags suitable for the present invention, for instance tag can be selected from the group comprising OLLAS, AviTag, C-tag, Calmodulin-tag, polyglutamate tag, E-tag, FLAG-tag, HA-tag, His-tag, Myc-tag, NE-tag, Rho1D4-tag, S-tag, SBP-tag, Softag 1, Softag 3, Spot-tag, Strep-tag, TC tag, Ty tag, V5 tag, VSV-tag, Xpress tag, Isopeptag, SpyTag, SnoopTag, SnoopTagJr, DogTag, SdyTag, BCCP (Biotin Carboxyl Carrier Protein), Gluta-thione-S-transferase-tag, Green fluorescent protein (GFP)-tag, HaloTag, SNAP-tag, CLIP-tag, Maltose binding pro-tein-tag, Nus-tag, Thioredoxin-tag, Fc-tag, Carbohydrate Recognition Domain or CRDSAT-tag. Particular examples of suitable tags are OLLAS and His-tag. Likewise, there is a multitude of known promoters suitable for the present invention. The promoter can be chosen to lead to the specific expression of the temperature-sensitive TRP channel having an extracellular tag in at least one of retinal cell population selected from cones, rods, horizontal cells, rod bipolar cells, ON bipolar cells, OFF bipolar cells, amacrine cells, ganglion cells. If at least the cell body of a photoreceptor is still present in the retina of the subject, the promoter can be chosen so that it leads to the specific expression of the temperature-sensitive TRP channel having an extracellular tag in at least one photoreceptor type, for instance in cones.

The present invention also encompasses a nanomaterial conjugated to a molecule specifically binding to an extra-cellular tag, for use in a method for vision restoration comprising the steps of expressing a temperature-sensitive transient receptor potential (TRP) channel having an extra-cellular tag in the retina of a subject and of contacting said retina with said nanomaterial conjugated to a molecule specifically binding to an extracellular tag, wherein said an extracellular tag is the extracellular tag of the temperature-sensitive transient receptor potential (TRP) channel, and wherein said nanomaterial is able to generate heat by absorbing radiations of a specific wavelength. The skill person knows a large number of suitable nanomaterials. For instance, the nanomaterial can be selected from the group comprising silver nanoparticles, copper selenides, gold nan-oparticles, platinum nanoparticles, Rose Bengal, W18O19 nanowires, gold nanorods, titania nanoparticles, gold nano-shells, polypyrrole capped Fe3O4 nanoparticles, gold nan-oechinus, CuInS2, ZnS nanoparticles, ITO nanocrystals, palladium nanoparticles, dithienquinoxaline, photofrin, phthalocyanine, malachite green carbon nanotubes, and BODIPY-FL dye. In some embodiments, the nano material can be gold nanorods having a length to width ratio of 5.5 or gold nanorods having a length to width ratio of 4.0.

The present invention hence encompasses a method for vision restoration comprising the steps of expressing a temperature-sensitive transient receptor potential (TRP) channel having an extracellular tag in the retina of a subject and of contacting said retina with a nanomaterial conjugated to a molecule specifically binding to said extracellular tag, wherein said nanomaterial generates heat by absorbing radiations of a specific wavelength.

As immediately evident for the skilled person, the meth-ods of the present invention are not limited to single pairs of tagged temperature-sensitive TRP channel and nanomaterial binding to the particular tagged. Several pairs, reacting to the same wavelength, thus increasing the signal, or to different discrete wavelength, thus broadening the visual spectrum can be used. Therefore, the present invention also encompasses a method for vision restoration as described herein-above comprising at least a further step of expressing a further temperature-sensitive TRP channel having an extracellular tag different from the extracellular tag of the first temperature-sensitive TRP channel having an extracel-lular tag in said retina of said subject and of contacting said retina with a further nanomaterial conjugated to a molecule specifically binding to said different extracellular tag, wherein said further nanomaterial generates heat by absorb-ing radiations of a specific wavelength which is the same or is different from the wavelength specific to the first nano-material.

The present invention further encompasses a vector com-prising any of the nucleic acid molecules described herein above. In some embodiments, this vector can be a viral vector, for instance the vector can be an AAV, a PRV or a lentivirus. In some embodiments, it is an AAV.

The present invention also encompasses a kit comprising at least an isolated nucleic as described herein above and a nanomaterial as described herein above.

SEQUENCE LISTING

Figure 1:
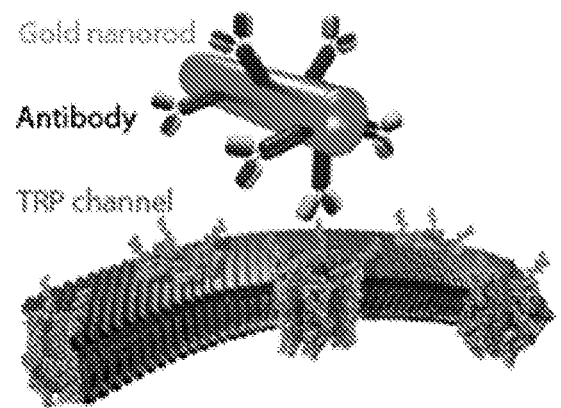
FIG. 1: Components of the near-infrared (NIR) sensor. Engineered TRP channels express protein epitope tags in extracellular domains and bind antibody conjugated gold nanorods.
Figure 2:
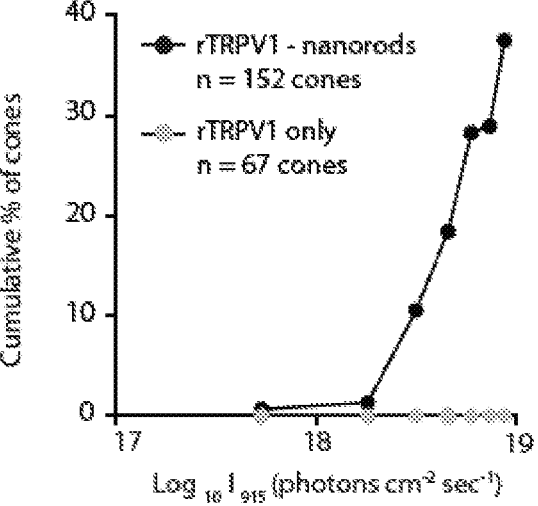
FIG. 2: Light sensitivity of rTRPV1 transduced rd1 cones with and without nanorods (Abs 915 nm).
Figure 3:
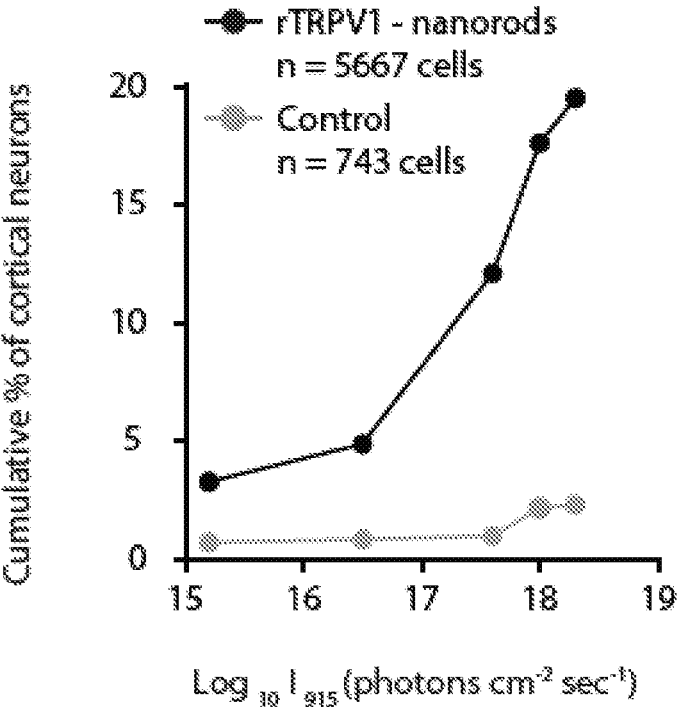
FIG. 3: Light sensitivity of cortical neurons in rTRPV1-nanorod (Abs 915 nm) transduced and control animals.
Figure 4:
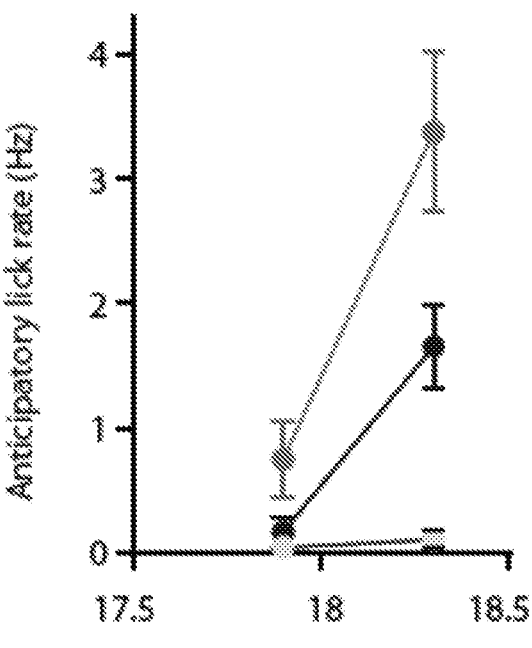
FIG. 4: Average anticipatory lick rates as a function of light intensity. Error bars=s.e.m. Near-infrared (NIR) full-field stimulation of one eye (915 nm, 200 ms) cues water presentation for head-fixed, water-restricted animals. Mice respond by licking before (anticipation) or after the appear-ance of water.
Figure 5:
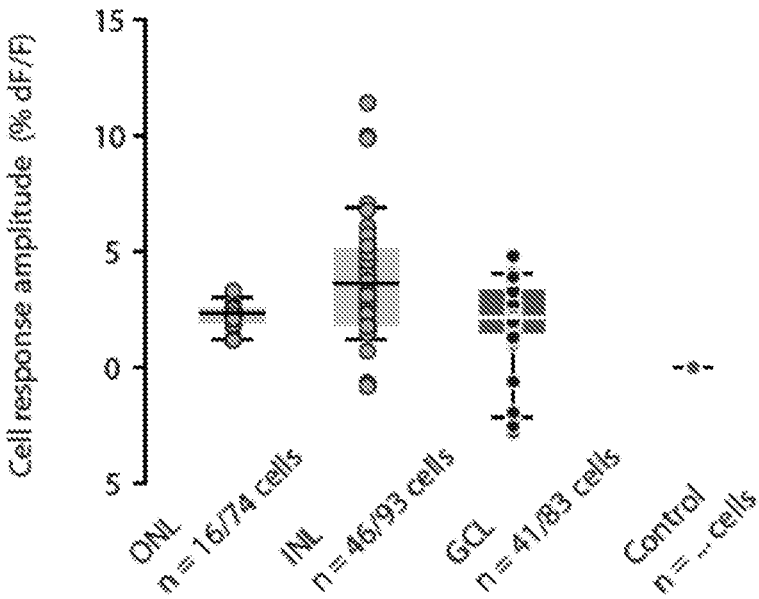
FIG. 5: Light sensitivity in rTRPV1-nanorod (Abs 915 nm) transduced and control human retinas. Responses in rTRPV1-nanorod transduced retinas are shown separately for each layer. All layers of the control human retina remained unresponsive.

In Vivo Mouse:
 SEQ ID NO:1—pAAV-mCar-TRPV1.465-6x-His (rTRPV1)
 SEQ ID NO:2—pAAV-mCar-TRPA1.755-Ollas (sTRPA1) (codon optimized)
 SEQ ID NO:3—pAAV-mCar-TRPA1.824-Ollas (codon optimized)

Ex Vivo Human Retina:

SEQ ID NO:4—pAAV-CAG-TRPV1.465-6xHis SEQ ID NO:4

In Vitro HEK Cells:

SEQ ID NO:5—pAAV-EF1a-TRPV1-2A-EGFP

SEQ ID NO:6—pAAV-EF1a-TRPV1.459-6x-His-2A-mCherry

SEQ ID NO:7—pAAV-EF1a-TRPV1.465-6xHis-2A-mCherry

SEQ ID NO:8—pAAV-EF1a-TRPA1-2A-EGFP

SEQ ID NO:9—pAAV-EF1a-TRPA1-2A-mCherry (codon optimized)

SEQ ID NO:10—pAAV-EF1a-TRPA1.755-Ollas-2A-mCherry (codon optimized)

SEQ ID NO:11—pAAV-EF1a-TRPA1.824.Ollas-2A-mCherry (codon optimized)

SEQ ID NO:12—Ollas peptide SGFANELGPRLMGK

SEQ ID NO:13—T2A self-cleaving peptide LEGRGSLLTCGDVEENPGPAPGST

DETAILED DESCRIPTION OF THE INVENTION

To address this need, the present inventors considered the use of temperature-sensitive transient receptor potential (TRP) channels. A few species such as boas, pythons and pit vipers can detect infrared light (1-30 μm) using temperature sensitive TRP channels expressed in a specialized organ (Nature 464, 1006-1011 (2010)). Thermal and visual images superimpose within the snake's brain, presumably enabling the snake to react to the environment with greater precision than with use of a single image only (Science 213, 789-791 (1981)). In order to restore vision, TRP channels could potentially be targeted to retinal cell types, as they are sensitive to infrared radiation. However, heat transfer to ectopically-expressed TRP channels via direct near-infrared illumination is inefficient, and requires high intensities that would damage the retina.

In order to develop a more efficient, NIR detector for retinal cell types, the present inventors engineered a two-component system consisting of a genetic and a nanomaterial component. The genetic component consisted of temperature sensitive TRP channels, engineered to incorporate an extracellular epitope tag recognizable by a specific antibody (Science 336, 604-608 (2012)). The nanomaterial component consisted of gold nanorods conjugated to an antibody against this epitope (Bioconjug Chem 24, 878-888 (2013)). This system uses surface plasmon resonance for heat transfer (Chem Soc Rev 41, 1191-1217 (2012)): gold nanorods capture NIR light at a pre-specified wavelength and use the energy to produce heat and open temperature-sensitive TRP channels in the proximity of the nanorods. Another advantage of this system is that the epitope can be engineered to ensure the specificity of antibody binding to engineered TRP channels since some TRP channels, such as TRPV1, are naturally expressed in the retina (Front Cell Neurosci 12, 353 (2018); Cells 3, 914-938 (2014).). Finally, this system proved to be so versatile, that it can be tailored to respond to any wavelength by varying the physical properties of the nanomaterial.

The present invention therefore encompasses an isolated nucleic acid molecule comprising a nucleotide sequence coding for a temperature-sensitive transient receptor potential (TRP) channel having an extracellular epitope tag, for use in therapy or prophylaxis of vision loss in a human or animal subject in need thereof, and in particular in a method for vision restoration comprising the steps of expressing said temperature-sensitive TRP channel having an extracellular epitope tag in the retina of a subject and of contacting said retina with a nanomaterial conjugated to a molecule specifically binding to said extracellular epitope tag. According to the invention, said nanomaterial generates heat by absorbing radiations of a specific wavelength. According to the invention, said isolated nucleic acid molecule further comprises a promoter operatively linked to said temperature-sensitive TRP channel having an extracellular epitope tag and leading to the specific expression of said temperature-sensitive TRP channel having an extracellular epitope tag in at least one specific cell population of said retina.

There is a large variety of temperature-sensitive TRP channel suitable for the invention, and the temperature-sensitive TRP channel can, for instance, be selected from the group comprising TRPM, TRPA, and TRPV, for instance TRPV1 or TRPA1, and homologs thereof as well as functional fragments.

The epitope tag is preferably selected from the group consisting of: OLLAS, AviTag, C-tag, Calmodulin-tag, polyglutamate tag, E-tag, FLAG-tag, HA-tag, His-tag, Myc-tag, NE-tag, Rho1D4-tag, S-tag, SBP-tag, Softag 1, Softag 3, Spot-tag, Strep-tag, TC tag, Ty tag, V5 tag, VSV-tag, Xpress tag, Isopeptag, SpyTag, SnoopTag, SnoopTagJr, DogTag, SdyTag, BCCP (Biotin Carboxyl Carrier Protein), Glutathione-S-transferase-tag, Green fluorescent protein (GFP)-tag, HaloTag, SNAP-tag, CLIP-tag, Maltose binding protein-tag, Nus-tag, Thioredoxin-tag, Fc-tag, Carbohydrate Recognition Domain or CRDSAT-tag. Particular examples of suitable tags are OLLAS and His-tag.

Likewise, there is a multitude of known promoters suitable for the present invention. The promoter can be chosen to lead to the specific expression of the temperature-sensitive TRP channel having an extracellular tag in at least one of retinal cell population selected from cones, rods, horizontal cells, rod bipolar cells, ON bipolar cells, OFF bipolar cells, amacrine cells, ganglion cells. If at least the cell body of a photoreceptor is still present in the retina of the subject, the promoter can be chosen so that it leads to the specific expression of the temperature-sensitive TRP channel having an extracellular tag in at least one photoreceptor type, for instance in cones. Examples of such promoters can be found in Jüttner et al., Nature Neuroscience, 2019, 22:1345-1356.

The present invention also encompasses a nanomaterial conjugated to a molecule specifically binding to an extracellular tag, for use in a method for vision restoration comprising the steps of expressing a temperature-sensitive transient receptor potential (TRP) channel having an extracellular tag in the retina of a subject and of contacting said retina with said nanomaterial conjugated to a molecule specifically binding to an extracellular tag, wherein said an extracellular tag is the extracellular tag of the temperature-sensitive transient receptor potential (TRP) channel, and wherein said nanomaterial is able to generate heat by absorbing radiations of a specific wavelength.

In preferred embodiments, the nanomaterial is selected from the group consisting of: silver nanoparticles, copper selenides, gold nanoparticles, platinum nanoparticles, Rose Bengal, W18O19 nanowires, gold nanorods, titania nanoparticles, gold nanoshells, polypyrrole capped Fe3O4 nanoparticles, gold nanoechinus, CuInS2, ZnS nanoparticles, ITO nanocrystals, palladium nanoparticles, dithienquinoxaline, photofrin, phthalocyanine, malachite green carbon nanotubes, and BODIPY-FL dye. In some embodiments, the nano material can be gold nanorods having a length to width ratio of 5.5 or gold nanorods having a length to width ratio of 4.0.

The present invention hence encompasses a method for vision improvement and/or restoration comprising the steps of expressing a temperature-sensitive transient receptor potential (TRP) channel having an extracellular tag in the retina of a subject and of contacting said retina with a nanomaterial conjugated to a molecule specifically binding to said extracellular tag, wherein said nanomaterial generates heat by absorbing radiations of a specific wavelength.

As immediately evident for the skilled person, the methods of the present invention are not limited to single pairs of tagged temperature-sensitive TRP channel and nanomaterial binding to the particular tagged. Several pairs, reacting to the same wavelength, thus increasing the signal, or to different discrete wavelengths, thus broadening the visual spectrum can be used. Therefore, the present invention also encompasses a method for vision restoration as described herein-above comprising at least a further step of expressing a further temperature-sensitive TRP channel having an extracellular tag different from the extracellular tag of the first temperature-sensitive TRP channel having an extracellular tag in said retina of said subject and of contacting said retina with a further nanomaterial conjugated to a molecule specifically binding to said different extracellular tag, wherein said further nanomaterial generates heat by absorbing radiations of a specific wavelength which is the same or is different from the wavelength specific to the first nanomaterial.

The present invention further encompasses a vector comprising any of the nucleic acid molecules described herein above. In some embodiments, this vector can be a viral vector, for instance the vector can be an AAV, a PRV or a lentivirus. In some embodiments, it is an AAV.

The present invention also encompasses a kit comprising at least an isolated nucleic as described herein above and a nanomaterial as described herein above.

Compositions comprising the nucleic acid molecules and/ or nanomaterials of the invention are also encompassed by the present invention. Said compositions can be pharmaceutically acceptable compositions.

Moreover, the nucleic acid molecules and/or nanomaterials of the invention can be used to manufacture medicaments and/or to treat patients for vision restoration.

It is to be understood that the medicament is generally used therapeutically, but it may be used in a prophylactic sense, when a subject has been identified as being likely to suffer from blindness, but actual vision loss has not yet occurred or has only minimally occurred.

By "blindness" is meant total or partial loss of vision. Typically the medicament may be used to treat blindness associated with macular degeneration, glaucoma and/or retinitis pigmentosa. However, it is to be appreciated that any disease or condition which leads to degeneration or non-functioning of photoreceptors in the eye may be treated using the medicament. Moreover, without wishing to be bound by theory, it is believed that the present invention will be particularly effective for curing blindness at early stages of retinal degeneration (rd) when photoreceptor function is lost but the photoreceptor-to-bipolar synapse may still be intact.

Once expressed in an appropriate retinal cell, the nucleic acid molecules of the invention inserts within the plasma membrane of the cell, rendering the cell photosensitive and able to cause ion transport, cation or anion, in response to light. Nevertheless, although it is known that the retina is sensitive to very wide ranges of light intensities due to the adaptive nature of photoreceptors, light-gated ion channels or pumps may not be able to adapt and may therefore respond only to a narrow range of light intensities. If this is the case, such a limitation may be mitigated by use of image intensifiers and/or image converters known in the art. For example, a patient who has been treated by the above described method, may wear, image intensifiers/enhancers mounted, for example, on spectacles or the like.

By way of an example, an image intensifying device, such as those provided by Telesensory (http://www.telesensory-.com), may be combined with a retinal scanning device (RSD) as developed by Microvision (http://www.microvision.com/milprod.html), to provide a head-worn apparatus capable of delivering a bright, intensified image directly to the retina of a patient with impaired vision (http://www.telesensory.com/home8.html). Briefly, a RSD projects images onto the retina such that an individual can view a large, full-motion image without the need for additional screens or monitors. Thus, by projecting an intensified image directly to the retina of an individual with impaired vision, it may be possible to improve vision in those considered to be blind.

In case of expressing the nucleic acid of the invention in retinal bipolar or ganglion cells some aspects of the network processing capabilities of the retina can be lost. For example horizontal cell mediated lateral inhibition can be lost if light activates bipolar or ganglion cells. In these cases a retina like processor (D. Balya and B. Roska: "Retina model with real time implementation", International Symposium on Circuits and Systems ISCAS 2005, Kobe, Japan, May, pp. 5222-5225., also see http://www.anafocus.com/ and http://www.eutecus.com/) can be combined with the Microvision system.

If the nucleic acid molecule of the invention is expressed in photoreceptors as mentioned before the polarity of light response in photoreceptors can inverse. If necessary, that can be corrected with inverting the polarity of the projected image: dark pixels becoming light and light pixels becoming dark.

These and other aspects of the present invention should be apparent to those skilled in the art, from the teachings herein.

For convenience, the meaning of certain terms and phrases employed in the specification, examples, and appended claims are also provided below.

The singular forms "a," "an," and "the" include plural reference unless the context clearly dictates otherwise.

"Polynucleotide" and "nucleic acid", used interchangeably herein, refer to polymeric forms of nucleotides of any length, either ribonucleotides or deoxyribonucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids, PNA and LNA. Polynucleotides may further comprise genomic DNA, cDNA, or DNA-RNA hybrids.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical." The inhibition of hybridization of the completely complementary sequence to the target sequence may be examined using a hybridization assay (Southern or Northern blot, solution hybridization and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarities (e.g., less than about 30% identity); in the absence of non-specific binding, the probe will not hybridize to the second non-complementary target sequence.

Another way of viewing sequence identity in the context to two nucleic acid or polypeptide sequences includes reference to residues in the two sequences that are the same when aligned for maximum correspondence over a specified region. As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

"Cell type" refers to a cell from a given source (e.g., tissue or organ) or a cell in a given state of differentiation, or a cell associated with a given pathology or genetic makeup.

"Polypeptide" and "protein", used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

A "fragment of a protein" refers to a protein that is a portion of another protein. For example, fragments of proteins may comprise polypeptides obtained by digesting full-length protein isolated from cultured cells. In one embodiment, a protein fragment comprises at least about 6 amino acids. In another embodiment, the fragment comprises at least about 10 amino acids. In yet another embodiment, the protein fragment comprises at least about 16 amino acids.

An "expression product" or "gene product" is a biomolecule, such as a protein or mRNA, that is produced when a gene in an organism is transcribed or translated or post-translationally modified.

"Host cell" refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

The term "functional equivalent" is intended to include the "fragments", "mutants", "derivatives", "alleles", "hybrids", "variants", "analogs", or "chemical derivatives" having an activity which is comparable to that of the native gene or virus.

"Isolated" refers to a polynucleotide, a polypeptide, an immunoglobulin, a virus or a host cell that is in an environment different from that in which the polynucleotide, the polypeptide, the immunoglobulin, the virus or the host cell naturally occurs.

"Substantially purified" refers to a compound that is removed from its natural environment and is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% or more free from other components with which it is naturally associated.

"Diagnosis" and "diagnosing" generally includes a determination of a subject's susceptibility to a disease or disorder, a determination as to whether a subject is presently affected by a disease or disorder, a prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

"Biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived therefrom and the progeny thereof. The term specifically encompasses a clinical sample, and further includes cells in cell culture, cell supernatants, cell lysates, serum, plasma, urine, amniotic fluid, biological fluids, and tissue samples. The term also encompasses samples that have been manipulated in any way after procurement, such as treatment with reagents, solubilization, or enrichment for certain components.

"Individual", "subject", "host" and "patient", used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Hybridization" refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

"Stringent conditions" refers to conditions under which a probe may hybridize to its target polynucleotide sequence, but to no other sequences. Stringent conditions are sequence-dependent (e. g., longer sequences hybridize specifically at higher temperatures). Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the target sequence hybridize to the target sequence at equilibrium. Typically, stringent conditions will be those in which the salt concentration is at least about 0.01 to about 1.0 M sodium ion concentration (or other salts) at about pH 7.0 to about pH 8.3 and the temperature is at least about 30° C. for short probes (e. g., 10 to 50 nucleotides). Stringent conditions may also be achieved with the addition of destabilizing agents, such as formamide.

"Biomolecule" includes polynucleotides and polypeptides.

"Biological activity" refers to the biological behavior and effects of a protein or peptide. The biological activity of a protein may be affected at the cellular level and the molecular level. For example, the biological activity of a protein may be affected by changes at the molecular level. For example, an antisense oligonucleotide may prevent translation of a particular mRNA, thereby inhibiting the biological activity of the protein encoded by the mRNA. In addition, an immunoglobulin may bind to a particular protein and inhibit that protein's biological activity.

"Oligonucleotide" refers to a polynucleotide sequence comprising, for example, from about 10 nucleotides (nt) to about 1000 nt. Oligonucleotides for use in the invention are for instance from about 15 nt to about 150 nt, for instance from about 150 nt to about 1000 nt in length. The oligonucleotide may be a naturally occurring oligonucleotide or a synthetic oligonucleotide.

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5'linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e. g., hexose phosphodiester; peptide nucleic acids). The modifications may be internal (single or repeated) or at the end (s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e. g., 3'-substituted ribonucleotides or deoxyribonucleotide monomers), any of which are bound together via 5' to 3'linkages.

"Biomolecular sequence" or "sequence" refers to all or a portion of a polynucleotide or polypeptide sequence.

The term "detectable" refers to a polynucleotide expression pattern which is detectable via the standard techniques of polymerase chain reaction (PCR), reverse transcriptase—(RT) PCR, differential display, and Northern analyses, which are well known to those of skill in the art. Similarly, polypeptide expression patterns may be "detected" via standard techniques including immunoassays such as Western blots.

A "target gene" refers to a polynucleotide, often derived from a biological sample, to which an oligonucleotide probe is designed to specifically hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide may also refer to the specific subsequence of a larger polynucleotide to which the probe is directed or to the overall sequence (e.g., gene or mRNA) whose expression level it is desired to detect.

A "target protein" refers to a polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e. g., gene or mRNA) whose expression level it is desired to detect.

"Complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

"BLAST" refers to Basic Local Alignment Search Tool, a technique for detecting ungapped sub-sequences that match a given query sequence.

"BLASTP" is a BLAST program that compares an amino acid query sequence against a protein sequence database. "BLASTX" is a BLAST program that compares the six-frame conceptual translation products of a nucleotide query sequence (both strands) against a protein sequence database.

A "cds" is used in a GenBank DNA sequence entry to refer to the coding sequence. A coding sequence is a sub-sequence of a DNA sequence that is surmised to encode a gene.

A "consensus" or "contig sequence", as understood herein, is a group of assembled overlapping sequences, particularly between sequences in one or more of the databases of the invention.

The nucleic acid molecules of the present invention can be produced by a virus harbouring a nucleic acid that encodes the relevant gene sequence. The virus may comprise elements capable of controlling and/or enhancing expression of the nucleic acid. The virus may be a recombinant virus. The recombinant virus may also include other functional elements. For instance, recombinant viruses can be designed such that the viruses will autonomously replicate in the target cell. In this case, elements that induce nucleic acid replication may be required in a recombinant virus. The recombinant virus may also comprise a promoter or regulator or enhancer to control expression of the nucleic acid as required. Tissue specific promoter/enhancer elements may be used to regulate expression of the nucleic acid in specific cell types. The promoter may be constitutive or inducible.

A "promoters" is a region of DNA that is generally located upstream (towards the 5' region) of the gene that is needed to be transcribed. The promoter permits the proper activation or repression of the gene which it controls. Examples of promoters which are suitable for the invention are the human rhodopsin promoter (Allocca et al., Novel AAV serotypes efficiently transduce murine photoreceptors, J Virol. (2007)), the human red opsin promoter (Nathan et al., Science. 1986 Apr. 11; 232(4747):193-202), the red cone opsin promoter, the arr3 promoter (Zhu, X. et al. Mouse cone arrestin gene characterization: promoter targets expression to cone photoreceptors. *FEBS Letters* 524, 116-122 (2002)) or the Grm6 promoter (Masu, M. et al. Specific deficit of the ON response in visual transmission by targeted disruption of the mGluR6 gene. *Cell* 180, 757-765 (1995)), or functional fragments thereof. As used herein, the term "promoter" refers to any cis-regulatory elements, including enhancers, silencers, insulators and promoters. A promoter is a region of DNA that is generally located upstream (towards the 5' region) of the gene that is needed to be transcribed. The promoter permits the proper activation or repression of the gene which it controls. In the context of the present invention, the promoters lead to the specific expression of genes operably linked to them in the photoreceptors. "Specific expression" of an exogenous gene, also referred to as "expression only in a certain type of cell" means that at least more than 75%, preferably more than 85%, more that 90% or more than 95%, of the cells expressing the exogenous gene of interest are of the type specified, i.e. photoreceptors in the present case.

Contaminant components of its natural environment are materials that would interfere with the methods and compositions of the invention, and may include enzymes, hormones, and other proteinaceous or nonproteinaceous solutes. Ordinarily, an isolated agent will be prepared by at least one purification step. In one embodiment, the agent is purified to at least about 60%, at least about 65%, at least about 70%, at least about 75%, at least about 80%, at least about 85%, at least about 88%, at least about 90%, at least about 92%, at least about 95%, at least about 97%, at least about 98%, at least about 99%, at least about 99.9%, or at least about 99.99% by weight.

"Expressing" a protein in a cell means to ensure that the protein is present in the cell, e. g., for the purposes of a procedure of interest. In numerous embodiments, "expressing" a protein will comprise introducing a transgene into a cell comprising a polynucleotide encoding the protein, operably linked to a promoter, wherein the promoter is a constitutive promoter, or an inducible promoter where the conditions sufficient for induction are created, as well as a localization sequence. However, a cell that, e. g., naturally expresses a protein of interest, can be used without manipulation and is considered as "expressing" the protein.

A "fluorescent probe" refers to any compound with the ability to emit light of a certain wavelength when activated by light of another wavelength.

"Fluorescence" refers to any detectable characteristic of a fluorescent signal, including intensity, spectrum, wavelength, intracellular distribution, etc.

"Detecting" fluorescence refers to assessing the fluorescence of a cell using qualitative or quantitative methods. For instance, the fluorescence is determined using quantitative means, e. g., measuring the fluorescence intensity, spectrum, or intracellular distribution, allowing the statistical comparison of values obtained under different conditions. The level can also be determined using qualitative methods, such as the visual analysis and comparison by a human of multiple samples, e. g., samples detected using a fluorescent microscope or other optical detector (e. g., image analysis system, etc.) An "alteration" or "modulation" in fluorescence refers to any detectable difference in the intensity, intracellular distribution, spectrum, wavelength, or other aspect of fluorescence under a particular condition as compared to another condition. For example, an "alteration" or "modulation" is detected quantitatively, and the difference is a statistically significant difference. Any "alterations" or "modulations" in fluorescence can be detected using standard instrumentation, such as a fluorescent microscope, CCD, or any other fluorescent detector, and can be detected using an automated system, such as the integrated systems, or can reflect a subjective detection of an alteration by a human observer.

An assay performed in a "homogeneous format" means that the assay can be performed in a single container, with no manipulation or purification of any components being required to determine the result of the assay, e. g., a test agent can be added to an assay system and any effects directly measured. Often, such "homogeneous format" assays will comprise at least one component that is "quenched" or otherwise modified in the presence or absence of a test agent. ell.

Any of a number of cell types can be used in the present invention. For example, any eukaryotic cell, including plant, animal, and fungal cells can be used. In some embodiments, neurone will be used. As used herein, "cells" can include whole cells (untreated cells), permeabilized cells, isolated mitochondria, and proteoliposomes, e. g., proteoliposomes reconstituted with a UCP or another protein of interest. The care and maintenance of cells, including yeast cells, is well known to those of skill in the art and can be found in any of a variety of sources, such as Freshney (1994) Culture of Animal Cells. Manual of Basic Technique, Wiley-Liss, New York, Guthrie & Fink (1991), Guthrie and Fink, Guide to Yeast Genetics and Molecular Biology, Academic Press, Ausubel et al. (1999) Current Protocols in Molecular Biology, Greene Publishing Associates, and others.

Cells can be used at any of a wide range of densities, depending on the dye, the test agent, and the particular assay conditions. For instance, a density of about $OD_{600}$=0.01 to 1 is used, for example between about 0.05 and 0.5, e.g. about 0.1.

Methods for expressing heterologous proteins in cells are well known to those of skill in the art, and are described, e. g., in Ausubel (1999), Guthrie and Fink (1991), Sherman, et al. (1982) Vlethods ineast Genetics, Cold Spring Harbor Laboratories, Freshney, and others. Typically, in such embodiments, a polynucleotide encoding a heterologous protein of interest will be operably linked to an appropriate expression control sequence for the particular host cell in which the heterologous protein is to be expressed. Any of a large number of well-known promoters can be used in such method. The choice of the promoter will depend on the expression levels to be achieved and on the desired cellular specificity. Additional elements such as polyadenylation signals, 5' and 3' untranslated sequences, etc. are also described in well-known reference books.

In metazoan (animals having the body composed of cells differentiated into tissues and organs) cells, promoters and other elements for expressing heterologous proteins are commonly used and are well known to those of skill. See, e. g., Cruz & Patterson (1973) Tissue Culture, Academic Press; Meth. Enzymology 68 (1979), Academic Press; Freshney, 3rd Edition (1994) Culture of Animal Cells: A Manual of Basic Techniques, Wiley-Liss. Promoters and control sequences for such cells include, e. g., the commonly used early and late promoters from Simian Virus 40 (SV40), or other viral promoters such as those from polyoma, adenovirus 2, bovine papilloma virus, or avian sarcoma viruses, herpes virus family (e. g., cytomegalovirus, herpes simplex virus, or Epstein-Barr Virus), or immunoglobulin promoters and heat shock promoters (see, e. g. Sambrook, Ausubel, Meth. Enzymology Pouwells, et al., supra (1987)). In addition, regulated promoters, such as metallothionein, (i. e., MT-1 and MT-2), glucocorticoid, or antibiotic gene "switches" can be used. Enhancer regions of such promoters can also be used.

Expression cassettes are typically introduced into a vector that facilitates entry of the expression cassette into a host cell and maintenance of the expression cassette in the host cell. Such vectors are commonly used and are well know to those of skill in the art. Numerous such vectors are commercially available, e. g., from Invitrogen, Stratagene, Clontech, etc., and are described in numerous guides, such as Ausubel, Guthrie, Strathem, or Berger, all supra. Such vectors typically include promoters, polyadenylation signals, etc. in conjunction with multiple cloning sites, as well as additional elements such as origins of replication, selectable marker genes (e. g., LEU2, URA3, TRP 1, HIS3, GFP), centromeric sequences, etc.

For expression in mammalian cells, any of a number of vectors can be used, such as pSV2, pBC12BI, and p91023, as well as lytic virus vectors (e. g., vaccinia virus, adenovirus, baculovirus), episomal virus vectors (e. g., bovine papillomavirus), and retroviral vectors (e. g., murine retroviruses).

As used herein, the term "disorder" refers to an ailment, disease, illness, clinical condition, or pathological condition.

As used herein, the term "pharmaceutically acceptable carrier" refers to a carrier medium that does not interfere with the effectiveness of the biological activity of the active ingredient, is chemically inert, and is not toxic to the patient to whom it is administered.

As used herein, the term "pharmaceutically acceptable derivative" refers to any homolog, analog, or fragment of an agent, e.g. identified using a method of screening of the invention, that is relatively non-toxic to the subject.

The term "therapeutic agent" refers to any molecule, compound, or treatment, that assists in the prevention or treatment of disorders, or complications of disorders.

Compositions comprising such an agent formulated in a compatible pharmaceutical carrier may be prepared, packaged, and labeled for treatment.

If the complex is water-soluble, then it may be formulated in an appropriate buffer, for example, phosphate buffered saline or other physiologically compatible solutions.

Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e. g., sorbitol syrup, cellulose derivatives or hydrogenated edible fats); emulsifying agents (e. g., lecithin or acacia); non-aqueous vehicles (e. g., almond oil, oily esters, or fractionated vegetable oils); and preservatives (e. g., methyl or propyl-p-hydroxybenzoates or sorbic acid). The pharmaceutical compositions may take the form of, for example, tablets or capsules prepared by conventional means with pharmaceutically acceptable excipients such as binding agents (e. g., pregelatinized maize starch, polyvinyl pyrrolidone or hydroxypropyl methylcellulose); fillers (e. g., lactose, microcrystalline cellulose or calcium hydrogen phosphate); lubricants (e. g., magnesium stearate, talc or silica); disintegrants (e. g., potato starch or sodium starch glycolate); or wetting agents (e. g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e. g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e. g., gelatin for use in an inhaler or insufflator may be formulated containing a powder mix of the compound and a suitable powder base such as lactose or starch.

The compounds may be formulated for parenteral administration by injection, e. g., by bolus injection or continuous infusion. Formulations for injection may be presented in unit dosage form, e. g., in ampoules or in multi-dose containers, with an added preservative.

The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e. g., sterile pyrogen-free water, before use.

The compounds may also be formulated in rectal compositions such as suppositories or retention enemas, e. g., containing conventional suppository bases such as cocoa butter or other glycerides.

The compounds may also be formulated as a topical application, such as a cream or lotion.

In addition to the formulations described previously, the compounds may also be formulated as a depot preparation. Such long acting formulations may be administered by implantation (for example, subcutaneously or intramuscularly) or by intramuscular injection.

Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The composition of the invention can be injected into the eye by intravitreal injection or by subretinal injection. The subretinal space, by definition, is the space between RPE cells and photoreceptors. In the subretinal space, injected material comes into direct contact with the plasma membrane of the photoreceptor, and RPE cells and subretinal blebs The invention also provides kits for carrying out the therapeutic regimens of the invention. Such kits comprise in one or more containers therapeutically or prophylactically effective amounts of the compositions in pharmaceutically acceptable form.

The composition in a vial of a kit may be in the form of a pharmaceutically acceptable solution, e. g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e. g., saline, dextrose solution, etc.), preferably sterile, to reconstitute the complex to form a solution for injection purposes.

In another embodiment, a kit further comprises a needle or syringe, preferably packaged in sterile form, for injecting the complex, and/or a packaged alcohol pad. Instructions are optionally included for administration of compositions by a clinician or by the patient.

The major groups of TRP channels include TRPM (melastatin), TRPV (vanilloid), TRPC (canonical), TRPP (polycystin), TRPML (mucolipin), and TRPA (subfamily A). At least TRPM, TRPA, and TRPV channels can respond to changes in temperature, with TRPM and TRPA known to respond to cold and TRPV known to respond to warmth, noxious heat, and pain.

Expression cassettes are typically introduced into a vector that facilitates entry of the expression cassette into a host cell and maintenance of the expression cassette in the host cell. Such vectors are commonly used and are well known to those of skill in the art. Numerous such vectors are commercially available, e. g., from Invitrogen, Stratagene, Clontech, etc., and are described in numerous guides, such as Ausubel, Guthrie, Strathem, or Berger, all supra. Such vectors typically include promoters, polyadenylation signals, etc. in conjunction with multiple cloning sites, as well as additional elements such as origins of replication, selectable marker genes (e. g., LEU2, URA3, TRP 1, HIS3, GFP), centromeric sequences, etc.

Viral vectors, for instance an AAV, a PRV or a lentivirus, are suitable to target and deliver genes to photoreceptors using a promoter of the invention.

Adeno-associated virus (AAV) is a small virus that infects humans and some other primate species. In many cases, AAV vectors integrate into the host cell genome. Gene therapy vectors using AAV can infect both dividing and quiescent cells and persist in an extrachromosomal state without integrating into the genome of the host cell, although in the native virus some integration of virally carried genes into the host genome does occur. These features make AAV a very attractive candidate for creating viral vectors for gene therapy. AAV belongs to the genus *Dependoparvovirus*, which in turn belongs to the family Parvoviridae. The virus is a small (20 nm) replication-defective, nonenveloped virus. AAV2 is the most popular serotype in various AAV-based research. However, it has been shown that other serotypes can be more effective as gene delivery vectors. For instance AAV6 appears much better in infecting airway epithelial cells, AAV7 presents very high transduction rate of murine skeletal muscle cells (similar to AAV1 and AAV5), AAV8 is superb in transducing hepatocytes and AAV1 and 5 were shown to be very efficient in gene delivery to vascular endothelial cells. In the brain, most AAV serotypes show neuronal tropism, while AAV5 also transduces astrocytes. AAV6, a hybrid of AAV1 and AAV2, also shows lower immunogenicity than AAV2. Serotypes can differ with the respect to the receptors they are bound to. For example, AAV4 and AAV5 transduction can be inhibited by soluble sialic acids (of different form for each of these serotypes), and AAV5 was shown to enter cells via the platelet-derived growth factor receptor. Recently, several useful AAV9 have also been published.

The output of retinal cells can be measured using an electrical method, such as a multi-electrode array or a patch-clamp, or using a visual method, such as the detection of fluorescence.

As used herein, "tags" or "protein tags" are peptide sequences genetically grafted onto a recombinant protein. There are many examples of tags known to the skilled person and the one listed herein-below are only nonrestrictive examples. Any tag that can be bound by a binding molecule conjugatable to nanomaterial can be used for the purpose of the present invention. These tags can be removable by chemical agents or by enzymatic means, such as proteolysis or intein splicing.

Tags can be appended to proteins so that they can be purified from their crude biological source using an affinity technique. These include chitin binding protein (CBP), maltose binding protein (MBP), Strep-tag and glutathione-S-transferase (GST).

The poly(His) tag, or His tag, is a widely used protein tag, which binds to metal matrices.

Tags can have the function of a solubilizing agent, e.g. for recombinant proteins expressed in chaperone-deficient species such as E. coli, to assist in the proper folding in proteins and keep them from precipitating. These include thioredoxin (TRX) and poly(NANP). Some affinity tags have a dual role as a solubilization agent, such as MBP, and GST.

Tags can also be used to alter chromatographic properties of the protein to afford different resolution across a particular separation technique. Often, these consist of polyanionic amino acids, such as FLAG-tag.

Epitope tags are short peptide sequences which are chosen because high-affinity antibodies can be reliably produced in many different species. These are usually derived from viral genes, which explain their high immunoreactivity. Epitope tags include V5-tag, Myc-tag, HA-tag, Spot-tag and NE-tag. These tags can be useful for western blotting, immunofluorescence and immunoprecipitation experiments, although they also find use in antibody purification.

Fluorescence tags can also be used to give visual readout on a protein. GFP and its variants are the most commonly used fluorescence tags. More advanced applications of GFP include using it as a folding reporter.

Protein tags may allow specific enzymatic modification (such as biotinylation by biotin ligase) or chemical modification (such as reaction with FlAsH-EDT2 for fluorescence imaging).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

In order to develop a more efficient, NIR detector for retinal cell types, the present inventors engineered a two-component system consisting of a genetic and a nanomaterial component.

First, they developed a system based on rat TRPV1 channels and gold nanorods with absorption maxima at 915 nm. 915 nm was selected to ensure low water absorption. The inventors inserted a 6x-His epitope tag in the middle of the first TRPV1 extracellular loop, after amino acid 459 or 465, since analysis of TRPV1 structure suggested that insertion at these sites would not disrupt protein function. To measure if tagged channels are functional, they performed whole cell voltage clamp in HEK cells expressing TRPV1.459-6x-His, TRPV1.465-6x-His or untagged TRPV1 while activating the channels by TRPV1 agonist capsaicin. The size of evoked currents were similar between TRPV1.465-6x-His and TRPV1 (Mann-Whitney U test, P=0.8551; TRPV1.465-6x-His, 1633±164 pA, n32 15 cells; TRPV1, 1766±276 pA, n=14 cells; mean±s.e.m), but less in TRPV1.459-6x-His (Mann-Whitney U test, P=0.0207; TRPV1.459-6x-His, 976±118 pA, n=19 cells; mean±s.e.m). Therefore, they used TRPV1.465-6x-His (rTRPV1) in subsequent experiments.

The inventors targeted rTRPV1 to cone photoreceptors of the Pde6brd1 (known as rd1) mouse via subretinal injection of adeno-associated virus (AAV) and a photoreceptor-specific promoter (mCar) to restrict expression. Rd1 mice have severe photoreceptor degeneration with complete loss of rod and dysfunctional light-insensitive cone photoreceptors by four weeks of age postnatal (P28). 55±10% of rd1 cones expressed rTRPV1 in the cell membrane (n=12,813 cones mm−2, n=7042 TRPV1 positive cones mm−2, mean±s.d). 98±1.6% of rat TRPV1 positive cells were cones (n=7216 TRPV1 positive cells mm−2, n=7042 TRPV1 positive cones mm−2, mean±s.d). All TRPV1 positive cones expressed the 6x-His tag (Mann-Whitney U test, P=0.7052).

To measure if NIR light drives responses in cones, the inventors performed two-photon calcium imaging of individual cone cell bodies and axon terminals in wholemount rd1 retinas in three conditions: first, rTRPV1 with 915 nm nanorods, second, rTRPV without nanorods and third, 915 nm nanorods without rTRPV1. To detect calcium signals, the inventors genetically targeted the calcium indicator GCaMP6s to cones via AAV that expresses GCaMP6s under a cone-specific promoter (ProA7). GCaMP6s was expressed in 67±5.1% of rd1 cones (n=12,813 cones mm−2, n=8635 GCaMP6s positive cones mm−2, mean±s.d).

rTRPV1 expressing cones showed large light evoked increases of calcium signal in the presence of nanorods ("NIR cone response"). rTRPV1 expressing cones without nanorods did not react to light. NIR cone response was larger (Mann-Whitney U Test, P=1.7×10-16; dF/F; rTRPV1-nanorods, 325±59.1%, n=57 cones; WT, 75±0.7%, n=115 cones; mean±s.e.m) and of opposite polarity compared to the visible light response of wild-type mice. More cones responded in the presence of both rTRPV1 and nanorods than with nanorods alone (Chi Squared Test, P=1.3×10-11; rTRPV1-nanorod, 38%, n=152 cones; nanorod only, 7%, n=194 cones). Response amplitudes did not differ between cell bodies and terminals (Mann-Whitney U test, P=0.981) indicating signal propagation to terminals. All subsequent experiments used both the TRP channel and the nanorod component ("NIR sensor"). Control mice were uninjected rd1 mice.

To assess if NIR retinal output propagates to higher visual centers, the inventors generated rd1 mice with GCaMP6s expression in layer 4 of the primary visual cortex (V1). Layer 4 receives feedforward connections from the lateral geniculate nucleus (LGN), one of the main output stations of the retina. They performed two-photon, single cell, layer 4 calcium imaging in vivo in NIR sensor injected and uninjected control mice and monitored cortical neural activity during light stimulation of the eye. Cortical activation was light intensity dependent. Some neurons responded preferentially at lower intensities. More cells responded in NIR sensor injected animals than in controls (Chi Squared Test, P=8.4×10-25; rTRPV1-nanorods, 19.5% %, n=5667 cells; control, 2.3%, n=743 cells). Response amplitudes were larger in NIR sensor injected animals (Mann-Whitney U test, P=6.2×10-8; dF/F; rTRPV1-nanorods, 45.0±1.3%, n=1105 cells; control, 12.1±3.8%, n=17 cells; mean±s.e.m). Enabling light sensitivity in a blind human retina requires specialized projector eye goggles that utilize specific wavelengths. Compatibility with current and future NIR projector goggles requires tunable NIR detectors.

Nanorod absorption spectra are wavelength-tuned by varying nanorod aspect ratios (length to width ratios). To tune neuronal activity to specific NIR wavelengths, the inventors selected a second type of gold nanorod with peak absorption at 980 nm (aspect ratio 5.5) and compared to the 915 nm nanorod (aspect ratio 4.0). Both types were paired to rTRPV1. For each nanorod type, the inventors then performed in vivo layer 4 cortical calcium imaging in rd1 mice twice: first, with stimulus wavelength matched to nanorod peak absorption, and second, with stimulus wavelength offset from the peak. To classify cortical neurons as 915 nm or 980 nm responsive, the inventors provided the computation of a wavelength preference index (WPI) for each NIR light responsive neuron. They found a strong preference for 980 nm over 915 nm light using nanorods tuned to 980 nm (Wilcoxon Signed Rank Test, P=1.1×10-33; 85% of neurons with WPI<0, n=263 total neurons). Similarly, in animals with nanorods tuned to 915 nm, more cortical neurons preferred 915 nm over 980 nm light (Wilcoxon Signed Rank Test, P=7.6×10-6; 63% of neurons with WPI<0, n=169 total neurons). Thus there is provided a nanorod technology which can be exploited to tune visual responses to any wavelength required.

Inventors provided a tuning of molecular components to increase sensitivity. A variety of TRPA1 channels serve as heat sensors in snakes. TRPA1 from the rat snake (*Elaphe obsolete lindheimen*) is more heat sensitive than rTRPV1. To determine the suitability of rat snake TRPA1 as a NIR sensor component, the inventors first engineered rat snake TRPA1 to express the peptide epitope tag Ollas within the first or second extracellular loop. They used Ollas since anti-Ollas antibodies show improved immunodetection compared to 6x-His and other conventional epitope tag antibodies. To identify loop domains, first, the location of extracellular loop domains of human TRPA1 were determined from its cryo-EM structure. Subsequently, potential loop domains of rat snake TRPA1 were identified after pairwise sequence alignment, between human and rat snake TRPA1. There is 62% sequence identity between rat snake and human sequences. Ollas was placed after amino acid 755 or 758, corresponding to the first loop, or after amino acid 824, corresponding to the second loop.

To measure if tagged channels are functional, the inventors performed whole cell voltage clamp in HEK cells expressing TRPA1.755-Ollas, TRPA1.758-Ollas, TRPA1.824-Ollas or untagged TRPA1 while activating the channels by TRPA1 agonist allyl isothiocyanate (AITC). The size of evoked currents were similar between TRPA1.755-Ollas and TRPA1 (Mann-Whitney U test, P=0.2220; TRPA1.755-Ollas, 315±56 pA, n=22 cells; TRPA1, 542±192 pA, n=7 cells; mean±s.e.m) and between TRPA1.824-Ollas and TRPA1 (Mann-Whitney U test, P=0.5222; TRPA1.824-Ollas, 566±83 pA, n=12 cells; mean±s.e.m). Currents were undetectable for TRPA1.758-Ollas (n=8). The inventors used TRPA1.755-Ollas (sTRPA1) in subsequent experiments.

They targeted sTRPA1 to cone photoreceptors of the rd1 mouse using the same AAV based approach as for rTRPV1. To activate the channel, 915 nm nanorods were conjugated to anti-Ollas antibodies. 50±13% of rd1 cone photoreceptor expressed sTRPA1 in the cell membrane (n=12,813 cones mm–2, n=6362 Ollas positive cones mm–2, mean±s.d). 99±0.8% of Ollas positive cells were cones (n=6403 Ollas positive cells mm–2, n=6362 Ollas positive cones mm–2, mean±s.d).

To compare rTRPV1 and sTRPA1 sensitivities, the inventors performed behavioral tests in TRP channel transduced rd1 mice. In the task, NIR light of two different intensities cued water appearance for water-restricted, head-fixed animals. The inventors evaluated anticipatory lick rates, defined as lick signal after a NIR flash but before the appearance of water. TRP transduced mice learned to associate NIR with water within four days. At the lower intensity anticipatory lick rates were similar between control mice and mice with rTRPV1 (Mann-Whitney U test, P=0.7028; rTRPV1-nanorod, 0.17±0.12 Hz, n=9 mice; control, 0.043±0.02 Hz, n=10 mice; mean±s.e.m) but higher for mice injected with sTRPA1 (Mann-Whitney U test, P=0.0186, sTRPA1-nanorod, 0.75±0.31 Hz, n=9 mice; mean±s.e.m). At the higher intensity rTRPV1 led to higher lick rates compared to control mice (Mann-Whitney U test, P=0.001; rTRPV1-nanorod, 1.7±0.34 Hz, n=9 mice; control, 0.11±0.057 Hz, n=10 mice; mean±s.e.m), but lower than with sTRPA1 (Mann-Whitney U test, P=0.0188; sTRPA1-nanorod, 3.4±0.64 Hz, n=9 mice; mean±s.e.m).

Finally, the inventors provided NIR sensitivity to in a blind human retina. They targeted rTRPV1 to adult human ex vivo retinal explants, kept alive in culture for eight weeks post mortem. Cultured retinas lose light sensitivity after 16 hours. Using a CAG promoter, a density of 2477±889 rTRPV1 positive photoreceptors was achieved per mm² of explant tissue (mean±s.d). 94.5±4.2% of rTRPV1 positive cells were photoreceptors (n=2583 rTRPV1 positive cells mm$^{-2}$, n=2477 rTRPV1 positive photoreceptors mm$^{-2}$, mean±s.d).

High-speed three-dimensional acousto-optic calcium imaging of neuronal network activity permits observation of response propagation from photoreceptors through the retina. To detect NIR light driven responses in the human retina, the inventors deposited nanorods (Abs 915 nm) over the photoreceptor side of the retina and performed two-photon calcium imaging of individual cells in the outer nuclear layer (ONL), which hosts photoreceptors, the inner nuclear layer (INL), which hosts horizontal, bipolar and amacrine cells, and the ganglion cell layer (GCL) which hosts ganglion and amacrine cells. To record calcium signals, the fluorescent calcium dye Oregon Green 488 BAPTA-1 (OGB-1) was electroporated into the cells. NIR light-evoked activation could be detected in rTRPV1 transduced (n=3), but not in control (n=3) retinal explants. rTRPV1 expressing photoreceptors showed NIR light-evoked increases of calcium signal. In cells of the INL and GCL layers, bidirectional changes in the calcium signal indicate activation of excitatory and inhibitory retinal pathways. More cells responded in the GCL than in the ONL, reflecting convergent retinal circuit organization (Chi Squared Test, P=0.0006; GCL, n=41 responding neurons, n=83 total neurons, 49.4%; ONL, n=16 responding photoreceptors, n=74 total photoreceptors, 21.6%). There was no significant difference in number of NIR light responding cells between INL and GCL (Chi Squared Test, P=0.89; INL, n=46 responding neurons, n=93 total neurons, 49.5%).

Materials and Methods

Wild-type (strain: C57BL/6J, stock number: 632) and rd1 mice (strain: C3H/HeNCrL, stock number: 025) were obtained from Charles River. Scnn1a-Cre mice (strain: B6;C3-Tg(Scnn1a-cre)3Aibs/J, stock number: 009613) and Ai94(TITL-GCaMP6s)-D mice (strain: B6.Cg-Igs7.tm94.1 (tetO-GCaMP6s)Hze.IJ, stock: 024104) were purchased from Jackson Laboratory. Ai94(TITL-GCaMP6s)-D mice were initially crossed to Scnn1a-Cre mice to obtain mice hemizygous for each gene. Hemizygous offspring were subsequently crossed to rd1 mice. Mice used for cortical experiments were hemizygous for Cre and GCaMP6s and homozygous for the rd1 mutation. Experiments were performed on 7-11 week old mice. Access to water was restricted for behavioral training but was otherwise freely available.

Human retinal tissue was obtained after corneal tissue harvest from adult multi-organ donors with no reported history of eye disease, n=2 eyes from n=2 donors. After cornea isolation, the iris, lens, and vitreous were removed and the retina was submerged in flowing Ames' medium (Sigma, A1420) saturated with 95% O2 and 5% CO2. The time elapsed from central retinal artery clamp to artificial ex vivo perfusion did not exceed 5 min. Samples used for tissue culture were of mid-peripheral origin, midway between the fovea and the anterior retinal border. For organotypic retinal culture, 4×4 mm retinal pieces were isolated and placed photoreceptor-side-up on polycarbonate membranes inserts (Corning, 3412). The cultures were maintained at 37° C. and 5% CO2 in DMEM/F12 medium (Thermo Fisher Scientific), supplemented with 0.1% bovine serum albumin (BSA), 10 µM O-acetyl-L-carnitine hydrochloride, 1 mM fumaric acid, 0.5 mM galactose, 1 mM glucose, 0.5 mM glycine, 10 mM HEPES, 0.05 mM mannose, 13 mM sodium bicarbonate, 3 mM taurine, 0.1 mM putrescine dihydrochloride, 0.35 µM retinol, 0.3 µM retinyl acetate, 0.2 µM (+)-α-tocopherol, 0.5 mM ascorbic acid, 0.05 µM sodium selenite, 0.02 µM hydrocortisone, 0.02 µM progesterone, 1 µM insulin, 0.003 µM 3,3',5-triiodo-L-thyronine, 2 000 U penicillin and 2 mg streptomycin (Sigma). For AAV infection, 40 µL of virus was applied per retinal explant 4-5 days after plating. The culture medium was renewed every 48 hours. Light responses were recorded from samples 8 weeks post-mortem.

Gold nanorods tuned to 915 nm or 980 nm were purchased from Nanopartz Inc (Loveland, USA) and were functionalized by conjugation to anti-Histidine (Millipore, Mouse monoclonal anti-polyHis, 05949) or anti-OLLAS (Novus Biologicals, Rat monoclonal anti-OLLAS Epitope Tag L2, NBP1-06713) antibodies. 1010 nanorods were administrated per eye. Additional nanorod related information can be found in Table 1.

TABLE 1

| Nanorod properties | Nanorods, 915 nm Anti-6x-His | Nanorods, 980 nm Anti-6x-His | Nanorods, 915 nm Anti-Ollas |
|---|---|---|---|
| Surface plasmon resonance (nm) | 905-915 | 980-990 | 903-915 |
| Concentration (nanorods/mL) | $10^{13}$ | $10^{13}$ | $10^{13}$ |
| IgG (per nanorod) | 18-22 | 24-25 | 19-20 |
| pH | 7 | 7 | 7 |
| Solution | PBS | PBS | PBS |
| Zeta Potential (mV) | −18 | −15 | −16 |

For TRP channel design, rat TRPV1 (NM 031982.1) and snake *Elaphe (Pantherophis)obsoleta lindheimeri* TRPA1 (GU 562966) open reading frame sequences were chemically synthesized by Genewiz Inc (South Plainfield, USA). The snake sequence was codon optimized for Mus musculus (Java Codon Adaptation Tool, www.jcat.de). Rat TRPV1 protein was tagged by 6x-His introduced in the first extracellular loop, after amino acid 459 or 465. Extracellular loop location was determined based on the cryo-EM structure of rat TRPV1 (PDB 3J5P). Snake TRPA1 protein was tagged by Ollas SGFANELGPRLMGK flanked by GSG linkers, introduced after amino acid 755 or 758 (first loop) or 824 (second loop). To identify loop domains, first, the location of extracellular loop domains of human TRPA1 (PDB 3J9P) were determined from its cryo-EM structure. Subsequently, predicted loop domains of snake TRPA1 were identified after pairwise sequence alignment, generated using HHPRED (L. Zimmermann et al. J Mol Biol 430, 2237-2243 (2018)), between C-terminal domains of human (Uniprot O75762) and snake TRPA1 (Uniprot D4P382).

TABLE 2

| TRP plasmid list. mCar refers to photoreceptor specific mouse cone arrestin promoter | | | |
|---|---|---|---|
| Plasmids generated | TRP origin | Promoter | Experiment |
| pAAV-EF1a-TRPV1 -T2A-GFP | rat | EF1a | HEK293T |
| pAAV-EF1a-TRPV1,459-6x-His-T2A-mCherry | rat | EF1a | HEK293T |
| pAAV-EF1a-TRPV1.465-6x-His-T2A-mCherry | rat | EF1a | HEK293T |
| pAAV-EF1a-TRPA1-T2A-GFP | snake | EF1a | HEK293T |
| pAAV-EF1a-TRPA1.755-Ollas-T2A-mCherry | snake | EF1a | HEK293T |
| pAAV-EF1a-TRPA1.758-Ollas-T2A-mCherry | snake | EF1a | HEK293T |
| pAAV-EF1a-TRPA1.824-Ollas-T2A-mCherry | snake | EF1a | HEK293T |
| pAAV-mCar-TRPV1.465-6x-His (rTRPV1) | rat | mCar | Mouse |
| pAAV-mCar-TRPA.755-Ollas (sTRPA1) | snake | mCar | Mouse |
| pAAV-CAG-TRPV1.465-6x-His | rat | CAG | Human |

For in vitro HEK293T cell experiments, sequences encoding TRP variants were fused to T2A self-cleaving peptide LEGRGSLLTCGDVEENPGPAPGST and either mCherry or GFP fluorescent protein. Variants were inserted into linearized pAAV-EF1a-CatCh-GFP plasmid via restriction sites and homologous recombination, replacing the CatCh-GFP sequence. pAAV-EF1a-CatCh-GFP plasmid was constructed by adaptor PCR and the Clontech In-Fusion kit using pcDNA3.1(-)-CatCh-GFP (a kind gift of E. Bamberg, MPI, Frankfurt) and pAAV-EF1a-GFP. To generate pAAV-mCAR-TRPV1.465-6x-His (rTRPV1), plasmid pAAV-mCar-MAC-mCherry was linearized with NotI/HindIII. Subsequently, PCR amplified TRPV1.465-6x-His (from pAAV-EF1a-TRPV1.465-6x-His-T2A-mCherry) was inserted, replacing the MAC-mCherry sequence. To generate pAAV-mCAR-TRPA1.755-Ollas (sTRPA1), plasmid pAAV-mCar-MAC-mCherry was linearized with NotI/MluI.

Subsequently, PCR amplified TRPA1.755-Ollas (from pAAV-EF1a-TRPA1.755-Ollas-T2A-mCherry) was inserted, replacing the MAC-mCherry sequence. To generate pAAV-CAG-TRPV1.465-6x-His, plasmid pAAV-CAG-ChrimsonR-tdtomato was linearized with ClaI/HindIII. Subsequently, PCR amplified TRPV1.465-6x-His (from pAAV-EF1a-TRPV1.465-6x-His-T2A-mCherry) was inserted, replacing the ChrimsonR-tdtomato sequence. The names of TRP plasmids generated are listed in Table S2. To generate pAAV-ProA7-GCaMP6s for cone photoreceptor activity monitoring, plasmid pAAV-EF1a-GCaMP6s (Addgene, 67526) was linearized with MluI/BamHI. Subsequently, PCR amplified ProA7 promoter (from pAAV-ProA7-EGFP) was inserted, replacing the EF1a sequence. To induce GCaMP6s expression in cortical experiments, AAV-pCAG-FLEX2-tTA2 plasmid was obtained from Addgene (65458).

AAV production was carried as described previously in J. Juttner et al. Nat Neurosci 22, 1345-1356 (2019). Briefly, HEK293T cells were co-transfected with an AAV transgene plasmid, an AAV helper plasmid encoding the AAV Rep2 and Cap proteins for the selected serotype, and the pHGT1-Adeno1 helper plasmid harboring adenoviral genes (kindly provided by C. Cepko, Harvard Medical School, Boston) using branched polyethyleneimine (PEI, Polysciences). The AAVs were isolated using a discontinuous iodixanol gradient (OptiPrep, Sigma, D1556) and ultracentrifugation. AAV particles were purified and concentrated in Millipore Amicon 100K columns. Genome copy number titration was performed using real-time PCR (Applied Biosystems, TaqMan reagents). AAVs were used when titer was equal to or greater than 1013 genome copies mL−1. serotype BP2 was used to deliver TRP channels to photoreceptors (T. Cronin et al. EMBO Mol Med 6, 1175-1190 (2014)). To induce GCaMP6s expression in cortical experiments, serotype PHP.eB (18) was used to deliver AAV-pCAG-FLEX2-tTA2.

Ocular injections to deliver AAVs expressing TRP variants and/or functionalized nanorods were performed on 4 week old mice anesthetized with 2.5% isoflurane. A small incision was made with a sharp 30 gauge needle at the nasal corneo-scleral junction and AAV and/or nanorods were co-injected through this incision into the subretinal space using a blunt 5 μL Hamilton syringe held in a micromanipulator. For cone photoreceptor activity monitoring, cone specific AAV-ProA7-GCaMP6s (11) was co-injected subretinally with rTRPV1 and/or nanorods. A maximum volume of 2.5 μL was administered per eye. For primary visual cortex activity monitoring, AAV-pCAG-FLEX2-tTA2 was delivered by intravenous retro-orbital injection as previously described by D. Hillier et al. Nat Neurosci 20, 960-968 (2017) 2 weeks after initial ocular injection of rTRPV1 and nanorods. There was a minimum incubation time of 3 weeks after intraocular injection before performing experiments on AAV injected animals.

Craniotomy surgery for in vivo two-photon imaging was performed as described previously (19). Briefly, mice were anesthetized with a mixture of fentanyl (Mepha) (0.05 mg/kg), medetomidine (Virbac) (0.5 mg/kg) and midazolam (Roche) (5.0 mg/kg) and were head-fixed in a stereotaxic frame (Narishige, SR-5M-HT). A circular craniotomy of ~3.5 mm diameter was made above the primary visual cortex. After removal of the skull flap, the cortical surface was kept moist with a cortex buffer containing 125 mM NaCl, 5 mM KCl, 10 mM glucose, 10 mM HEPES, 2 mM MgSO4 and 2 mM CaCl2. The cortex was then covered with a 3 mm diameter glass coverslip and sealed with dental acrylic cement (Paladur, Kulzer). A metal bar for head fixation during imaging was glued to the skull (Vetbond, 3M) followed by further dental cement treatment. For behavioral experiments, a custom-made titanium headbar was attached to the skull with tissue adhesive and dental cement.

For HEK293T cell experiments, cells were maintained at 37° C. on poly-D-lysine/laminin coated coverslips (GG-12-Laminin, Neuvitro) in DMEM supplemented with 10% fetal bovine serum. Cells were transfected with plasmids containing TRP variants using branched PEI. Cells were perfused in oxygenated Ringer's medium containing 110 mM NaCl, 2.5 mM KCl, 1 mM CaCl2, 1.6 mM MgCl2, 10 mM D-glucose and 22 mM NaHCO3 at ~36° C. for the duration of the experiment. Recordings were made in whole-cell voltage clamp mode with borosilicate pipettes (Sutter Instrument Company) pulled to between 4-6 MΩ resistance, voltage clamping the cells to −60 mV. The intracellular solution contained 115 mM potassium gluconate, 9.7 mM KCl, 1 mM MgCl2, 0.5 mM CaCl2, 1.5 mM EGTA, 10 mM HEPES, 4 mM ATP-Na2, 0.5 GTP-Na2 at pH 7.2. For comparison of currents between tagged and untagged channels, TRPV1 agonist capsaicin (Sigma, 360376) and TRPA1 agonist allyl isothiocyanate (AITC, Sigma, W203408) were bath applied at 2.5 μM and 700 μM, respectively, using a valve system (VC-6, Warner Instruments). Electrophysiological recordings were made using an Axon Multiclamp 700B amplifier (Molecular Devices). Signals were digitized at 10 kHz (National Instruments). Data was analyzed offline using MATLAB (MathWorks).

Near-infrared (NIR) pulses were produced by two custom-made, single wavelength NIR diode lasers emitting at 915 nm or 980 nm, modelled after J. Yao, B. Liu, and F. Qin. Biophys J 96, 3611-3619 (2009). The laser diode was driven by a pulsed quasi-CW current power supply (Lumina Power, Bradford, USA). The controller had a rise time of 25 μs. Laser emission from the diode was collimated using an aspherical lens (f ¼ 11.5 mm, 0.25 NA). For ex vivo retinal experiments, laser output was launched into a fiber optic patch cable (Thorlabs, M79L01) interconnected with a fiber optic cannula (Thorlabs, CFM14L20) (both 400 μm, 0.39 NA). The cannula was positioned 300 μm above and 300 μm lateral to the imaging plane, at angle of 30-35°. Full-field, 100 ms pulses were delivered every 2-10 s. For in vivo cortical and behavioral experiments lasers were connected to a fiber optic patch cable positioned 6 mm from the cornea (550 μm, 0.22 NA) (Thorlabs, M37L02). A visible laser line (532 nm), coupled to both NIR lasers, aided alignment over the center of the pupil. Full-field, 100 ms (cortex) and 200 ms (behavior) pulses were delivered every 2-30 s. Total laser power output, as a function of driving voltage, was measured by placing cannula (CFM14L20) and patch cable (M37L02) output at the entrance of an integrating sphere photodiode power sensor (Thorlabs, S142C) with a PM100D read-out unit. Oscilloscope read-out of laser response time was obtained by applying a step control voltage to the lasers. Light intensities are indicated in the text.

For two-photon calcium imaging of mouse cone photoreceptors, wild-type and rd1 retinas were isolated in oxygenated Ringer's medium. For cone photoreceptor calcium-based activity monitoring mouse retinas were mounted ganglion cell-layer-up on filter paper (MF-membrane, Millipore, HAWP01300) with a 2×2 mm aperture to allow for light stimulation of the photoreceptors. To expose photoreceptors, the pigment epithelium layer was peeled away. Nanorods were reapplied to the photoreceptor side after peeling (1010 nanorods). During imaging, the retina was continuously perfused with oxygenated Ringer's medium at ~36° C. The calcium sensor GCaMP6s was targeted to cone photoreceptors virally, using cell-type specific promoter ProA7 (Juttner et al. 2019) to restrict expression to cones. GCaMP6s-expressing cone cell bodies and axon terminals were imaged in a wholemount preparation of the retina. The two-photon microscope system used has been described previously by K. Yonehara et al. Neuron 79, 1078-1085 (2013). Briefly, the system was equipped with a two-photon laser scanning at 920 nm (Spectra Physics, Santa Clara, USA) and a 60× objective (Fluor, 1.0 NA, Nikon). Images were acquired using custom software developed by Z. Raics (SELS Software, Hungary), taking images of 150×150 pixels at 10 frames per s. Fluorescence was analyzed semi-online via custom-made software written in Python by Z. Raics (A. Drinnenberg et al. Neuron 99, 117-134 e111 (2018)). Cone axon terminals and cell bodies were segmented manually. Fluorescence values were then normalized as $\Delta F/F$, where F represents baseline fluorescence (mean fluorescence of a 1-2 s time window before the onset of the stimulus). Full-field, 915 nm, 100 ms stimulus was presented 2-3 times at each intensity. Full-field, 405 nm, 2 s stimulation was used for wild-type cones. Responses to different trials were averaged before calculating the peak response. Peak responses were analyzed offline using MAT-LAB. NIR induced peak responses were the means of 3 dF/F values within 2 s of stimulation onset, including the maximum value and its immediately adjacent 2 data points. Peak responses in wild-type cone axon terminals were calculated as the means of $\Delta F/F$ values during the second half of the stimulation period.

For two-photon calcium imaging in mouse primary visual cortex, Cre- and Tet-dependent Ai94-GCaMP6s mice were crossed to Scnn1a-Cre mice and to rd1 mice (see Animals). Tetracycline-controlled transactivator (tTA2), delivered by intravenous retro-orbital injection (see Injections), induced Layer 4 specific GCaMP6s expression 7-10 days later. GCaMP6s expressing neurons were imaged using a two-photon laser scanning at 920 nm (Femto2D RC, Femtonics, Budapest, Hungary), equipped with a 16× Nikon water-immersion objective (0.8 NA). During imaging, mice were anesthetized with chlorprothixene (Sigma, C1671) (2.5 mg/kg) and maintained with 0.25% isoflurane. A Python-based user interface controlled visual stimulation, data recording and alignment. Layer 4 imaging was performed in steps of 20 μm, at depths of 300-440 μm below the pial surface (23). 250×350 pixel images were acquired at 6-10 frames per s. Eyes were dilated with atropine 0.5% (Thea, 2094264) 15 min before starting imaging. Using an optical cable, full-field, 100 ms NIR light was presented 5 times at each intensity to the contralateral eye. To evaluate cortical wavelength preference, NIR stimulation was performed with wavelengths matched to and offset from nanorod absorption maxima. The same layer 4 population was imaged twice, once with 915 nm stimulation of the eye and once with 980 nm stimulation. To establish response correspondence during nanorod tuning experiments, imaging planes were manually aligned to image the same neurons across two conditions (matched and unmatched stimulation wavelengths). Detection of active cells was performed online as previously described by D. Hillier et al. Nat Neurosci 20, 960-968 (2017) and subsequently refined offline by A. Giovannucci et al. Elife 8, (2019). Responses were measured as the relative change in fluorescence ($\Delta F/F$) from baseline within 600 ms after stimulation onset. Responses to 5 trials were averaged before calculating the peak response. Cells were considered NIR responsive if a change in fluorescence was evident in at least 60% of trials. Wavelength preference index (WPI) was defined as: WPI=($\Delta F/F$ mismatched−$\Delta F/F$ matched)/($\Delta F/F$ mismatched+$\Delta F/F$ matched).

For mouse behavioral vision assessment, Rd1 mice underwent headbar surgery and were left to recover for 2-3 days before being placed on a water restriction schedule. Thereafter, mice were handled daily and received ~0.5-1 mL of water per session, until body weight reached ~80% of the ad libitum weight (typically within 5-7 days). Health status and weight were monitored daily. Before starting behavioral evaluation, mice were progressively habituated to the experimental setup, including head fixation and enclosure within a 'body' tube (Z. V. Guo et al. PLoS One 9, e88678 (2014)). Enclosure of the mouse body within a cylindrical acrylic tube was found to maximize animal comfort during head fixation. Eyes were dilated with atropine 0.5% 15 min before behavioral evaluation. Experiments were performed in the dark. Mice performed a voluntary action NIR detection task by licking a waterspout (blunt 18G needle, 5 mm from mouth) in response to full-field, 915 nm, 200 ms stimulation of one eye. Water (~7 μL) was automatically dispensed 500 ms after NIR light onset, through a calibrated gravity water system gated with a solenoid pinch valve. NIR intensities were $8.5 \times 10^{17}$ photons cm−2 s−1 or $1.9 \times 10^{18}$ photons cm−2 s−1, randomly interleaved. Inter-trial intervals ranged between 10-30 s. Mice were evaluated over 4 days. Typical sessions lasted 40 min during which mice performed ~100 trials. To assess the impact of the NIR light cue, lick rates were quantified in a time interval after NIR stimulus but before water valve opening. Spontaneous background lick rates (1 s time window before the onset of the stimulus) were subtracted from stimulus-driven lick rates. An Arduino Uno board provided control of the behavioral protocol, including lick detection, water valve opening, and variation of NIR stimulus intensities. Lick events were detected by a transistor-based circuit and recorded by a USB 6002 (National Instruments, Austin) data acquisition device. Custom control software was written in Python (Z. Raics, SELS Software).

For two-photon calcium imaging in ex vivo human retina, Oregon Green 488 Bapta-1 (OGB-1) calcium dye (Invitrogen, O-6806) was bulk electroporated into human retinal explants as described before (26). Briefly, the retina was flat mounted on anodisc filter membranes (#13, 0.2 μm pore size, GE Healthcare, Maidstone, UK) ganglion cell-layer-up. Low melting temperature 1% agarose gel (Sigma, A2790) was added to the ganglion cell side to stabilize the retina and was kept in place throughout the experiment. Nanorods were added to the photoreceptor side (1010 nanorods). Retinas were electroporated between 3 mm horizontal plate electrodes (Sonidel, CUY700P3E) with 10 μL of 5 mM OGB-1 in Ames' medium using 10-12 pulses (9 V, 100 ms, 1 Hz) from TGP110 Pulse Generator (Aim & TTi, Cambridge, England). The tissue was left to recover for 60 min before recording activity. During activity monitoring the human retina was continuously perfused with oxygenated Ames' solution at ~36° C. For acousto-optic imaging, a z-stack was taken before NIR stimulation with the acousto-optic deflector two-photon (AOD) microscope using a 16× water immersion objective (0.8 NA) to capture the 3D volume of the retina. Within this volume, the experimenter manually selected the cell soma position of OGB-1 filled cells. 100 ms NIR full-field light stimulus was presented 5 times at each intensity. During stimulation the AOD scanned a set of square XY planes encompassing each cell body at 30 Hz.

For immunofluorescence and confocal imaging, HEK293T cells and retinas were fixed overnight in 4% paraformaldehyde and washed overnight with phosphate buffered saline (PBS) at 4° C. To improve antibody penetration, wholemount retinas were subjected to freeze-thaw cycles after cryoprotection with 30% sucrose. After washing in PBS, retinal wholemounts, 3% agarose-embedded (SeaKem, Lonza, 50004) 150 µm thick retinal vibratome sections (Leica VT1000 S) or HEK293T cells on coverslips were incubated for 2-4 h in blocking buffer containing 10% normal donkey serum (NDS, Chemicon), 1% BSA, 0.5% TritonX-100, and 0.01% sodium azide (Sigma) in PBS. Primary antibody treatment was performed for 5-7 days at room temperature in buffer containing 3% NDS, 1% BSA, 0.01% sodium azide, and 0.5% TritonX-100 in PBS.

Primary antibodies used were rat monoclonal anti-GFP (Nacalai, 04404-84), rabbit polyclonal anti-GFP (Thermo Fisher Scientific, A11122), mouse monoclonal anti-CAR (H. Zhang et al. Invest Ophthalmol Vis Sci 44, 2858-2867 (2003)), rat monoclonal anti-RFP (Chromotek, 5F8-100), rabbit anti-RFP (Rockland, 600-401-379), rabbit polyclonal anti-Capsaicin receptor (Millipore, AB5370), rat monoclonal anti-OLLAS (Novus Biologicals, NBP1-06713), mouse monoclonal anti-polyHis (Millipore, 05949). Hoechst was used to stain cell nuclei. For microscopy retinas were mounted on glass slides with ProLong Gold antifade reagent (Invitrogen, P36982).

A Zeiss LSM 700 laser scanning confocal microscope was used to acquire images of antibody stained cells and tissues with an EC Plan-Neofluar 40×/1.30 oil M27 objective at up to 4 excitation laser lines according to secondary antibody specification. Expression was assessed from 1024×1024 pixel images in a z-stack with 0.75 µm steps. Images were processed using Imaris (Bitplane) and Image J (Fiji). AAV transduction was quantified from retinal wholemounts. In each sample the entire thickness of the retina was scanned by confocal microscopy at 3 or 5 randomly chosen areas in AAV transduced regions. Quantification was performed separately for outer nuclear layer, inner nuclear layer and ganglion cell layer.

To measure nanorod sizes by transmission electron microscopy 4 µL of nanorod stock solution was adsorbed for 2 min to glow-discharged formvar carbon-coated copper grids (Ted Pella Inc, Redding, USA, 01753-F). The grids were then blotted and negatively stained on 2 droplets of 2% uranyl acetate solution (Electron Microscopy Sciences, 22400) for 20 s. Samples were imaged at a nominal magnification of 30000× using a Tecnai Spirit electron microscope (FEI, Eindhoven, Netherlands) operating at 120 kV. Electron micrographs were recorded using a bottom mount 4K×4K CCD FEI Eagle camera.

For scanning electron microscopy, retinal samples were placed on glass slides. Nanorod stock solution was applied for 40 min at room temperature, followed by extensive rinses with deionized H2O. The retina was dehydrated progressively for 30-50-70-90-95-100 min (2×) and was then immersed in hexamethyldisilazane (Sigma, 440191) for 10 min (2×). Subsequently, the samples were dried for 90 min at 60° C. Samples were metalized with gold palladium (Quorum, SC7620) for 15 s and imaged in a scanning electron microscope (FEI Versa 3D) at 5 kV and 3 nm per pixel with an ETD detector. Lookup tables were inverted in post-processing.

The invention claimed is:

1. An isolated nucleic acid molecule comprising a nucleotide sequence coding for a temperature-sensitive transient receptor potential (TRP) channel having an extracellular epitope tag, for use in a method for vision restoration comprising the steps of expressing said temperature-sensitive TRP channel having an extracellular tag in the retina of a subject and of contacting said retina with a nanomaterial conjugated to a molecule specifically binding to said extracellular tag, wherein said nanomaterial generates heat by absorbing radiations of a specific wavelength, wherein said isolated nucleic acid molecule further comprises a promoter operatively linked to said temperature-sensitive TRP channel having an extracellular tag and leading to the specific expression of said temperature-sensitive TRP channel having an extracellular tag in at least one specific cell population of said retina, and wherein said promoter leads to the specific expression of said temperature-sensitive TRP channel having an extracellular tag in at least one photoreceptor type.

2. The isolated nucleic acid molecule of claim 1, wherein said temperature-sensitive TRP channel is selected from the group consisting of: TRPM, TRPA, TRPV, and homologs thereof.

3. The isolated nucleic acid molecule of claim 1, wherein said epitope tag is selected from the group consisting of:

OLLAS, AviTag, C-tag, Calmodulin-tag, polyglutamate tag, E-tag, FLAG-tag, HA-tag, His-tag, Myc-tag, NE-tag, Rho1D4-tag, S-tag, SBP-tag, Softag 1, Softag 3, Spot-tag, Strep-tag, TC tag, Ty tag, V5 tag, VSV-tag, Xpress tag, Isopeptag, SpyTag, SnoopTag, SnoopTagJr, DogTag, SdyTag, BCCP (Biotin Carboxyl Carrier Protein), Glutathione-S-transferase-tag, Green fluorescent protein (GFP)-tag, HaloTag, SNAP-tag, CLIP-tag, Maltose binding protein-tag, Nus-tag, Thioredoxin-tag, Fc-tag, and Carbohydrate Recognition Domain or CRDSAT-tag.

4. The isolated nucleic acid molecule of claim 1, wherein said tag is selected from OLLAS and His-tag.

5. A vector comprising the nucleic acid molecule of claim 1.

6. The vector of claim 5, wherein said vector is a viral vector.

7. The vector of claim 6, wherein said vector is an AAV vector, a PRV vector or a lentivirus vector.

8. The isolated nucleic acid molecule of claim 2, wherein said temperature-sensitive TRP channel is TRPV1, TRPA1, or homologs thereof.

9. The isolated nucleic acid of claim 1, wherein said promoter leads to the specific expression of said temperature-sensitive TRP channel having an extracellular tag in cones.

10. The vector of claim 7, wherein said vector is an AAV vector.

* * * * *

SEQUENCE LISTING

```
<160> NUMBER OF SEQ ID NOS: 13

<210> SEQ ID NO 1
<211> LENGTH: 4284
<212> TYPE: DNA
<213> ORGANISM: Mus musculus

<400> SEQUENCE: 1
ctgcgcgctc gctcgctcac tgaggccgcc cgggcaaagc ccgggcgtcg ggcgaccttt        60
ggtcgcccgg cctcagtgag cgagcgagcg cgcagagagg gagtggccaa ctccatcact       120
aggggttcct tgtagttaat gattaacccg ccatgctact tatctacgta gccatgctct       180
aggaagatcg gaattcgccc ttaagctagg gttcttccca ttttggctac atggtctttt       240
tttttacctt tttggttcct ttggcctttt ggcttttggc ttccagggct tctggatccc       300
ccccaacccc tcccatacac atacacatgt gcactcgtgc actcaaccca gcacaggata       360
atgttcattc ttgacctttc cacatacatc tggctatgtt ctctctctta tctacaataa       420
atctcctcca ctatacttag gagcagttat gttcttcttc tttctttctt ttttttttt       480 ttcattcagt aacatcatca gaatcccta gctctggcct acctcctcag taacaatcag       540
ctgatccctg gccactaatc tgtactcact aatctgtttt ccaaactctt ggcccctgag       600
ctaattatag cagtgcttca tgccacccac cccaacccta ttcttgttct ctgactccca       660
ctaatctaca cattcagagg attgtggata taagaggctg ggaggccagc ttagcaacca       720
gagctggagg atccatcaca ctggcggccg cgccaccatg gaacaacggg ctagcttaga       780
ctcagaggag tctgagtccc caccccaaga gaactcctgc ctggaccctc cagacagaga       840
ccctaactgc aagccacctc cagtcaagcc ccacatcttc actaccagga gtcgtacccg       900
```

-continued

```
gcttttggg aagggtgact cggaggaggc ctctcccctg gactgcccct atgaggaagg      960
cgggctggct tcctgcccta tcatcactgt cagctctgtt ctaactatcc agaggcctgg     1020
ggatggacct gccagtgtca ggccgtcatc ccaggactcc gtctccgctg gtgagaagcc     1080
cccgaggctc tatgatcgca ggagcatctt cgatgctgtg gctcagagta actgccagga     1140
gctggagagc ctgctgccct tcctgcagag gagcaagaag cgcctgactg acagcgagtt     1200
caaagaccca gagacaggaa agacctgtct gctaaaagcc atgctcaatc tgcacaatgg     1260
gcagaatgac accatcgctc tgctcctgga cgttgcccgg aagacagaca gcctgaagca     1320
gtttgtcaat gccagctaca cagacagcta ctacaagggc cagacagcac tgcacattgc     1380
cattgaacgg cggaacatga cgctggtgac cctcttggtg gagaatggag cagatgtcca     1440
ggctgcggct aacggggact tcttcaagaa aaccaaaggg aggcctggct tctactttgg     1500
tgagctgccc ctgtccctgg ctgcgtgcac caaccagctg gccattgtga agttcctgct     1560
gcagaactcc tggcagcctg cagacatcag cgcccgggac tcagtgggca cacggtgct      1620 tcatgccctg gtggaggtgg cagataacac agttgacaac accaagttcg tgacaagcat     1680
gtacaacgag atcttgatcc tgggggccaa actccacccc acgctgaagc tggaagagat     1740
caccaacagg aaggggctca cgccactggc tctggctgct agcagtggga agatcggggt     1800
cttggcctac attctccaga gggagatcca tgaacccgag tgccgacacc tatccaggaa     1860
gttcaccgaa tgggcctatg ggccagtgca ctcctccctt tatgacctgt cctgcattga     1920
cacctgtgaa aagaactcgg ttctggaggt gatcgcttac agcagcagtg agacccctaa     1980
ccgtcatgac atgcttctcg tggaacccctt gaaccgactc ctacaggaca agtgggacag     2040
atttgtcaag cgcatcttct acttcaactt cttcgtctac tgcttgtata tgatcatctt     2100
caccgcggct gcctactatc ggcctgtgga aggcttgccc ccctataagc tgcaccacca     2160
ccaccaccac aaaaacaccg ttgggggacta tttccgagtc accggagaga tcttgtctgt     2220
gtcaggagga gtctacttct tcttccgagg gattcaatat ttcctgcaga ggcgaccatc     2280
cctcaagagt ttgtttgtgg acagctacag tgagatactt ttctttgtac agtcgctgtt     2340
catgctggtg tctgtggtac tgtacttcag ccaacgcaag gagtatgtgg cttccatggt     2400
gttctccctg gccatgggct ggaccaacat gctctactat acccgaggat tccagcagat     2460
gggcatctat gctgtcatga ttgagaagat gatcctcaga gacctgtgcc ggtttatgtt     2520
cgtctacctc gtgttcttgt ttggattttc cacagctgtg gtgacactga ttgaggatgg     2580
gaagaataac tctctgccta tggagtccac accacacaag tgccgggggt ctgcctgcaa     2640
gccaggtaac tcttacaaca gcctgtattc cacatgtctg gagctgttca gttccaccat     2700
cggcatgggc gacctggagt tcactgagaa ctacgacttc aaggctgtct tcatcatcct     2760
gttactggcc tatgtgattc tcacctacat ccttctgctc aacatgctca ttgctctcat     2820
gggtgagacc gtcaacaaga ttgcacaaga gagcaagaac atctggaagc tgcagagagc     2880
catcaccatc ctggatacag agaagagctt cctgaagtgc atgaggaagg ccttccgctc     2940
tggcaagctg ctgcaggtgg ggttcactcc tgacggcaag gatgactacc ggtggtgttt     3000
cagggtggac gaggtaaact ggactacctg gaacaccaat gtgggtatca tcaacgagga     3060
cccaggcaac tgtgagggcg tcaagcgcac cctgagcttc tccctgaggt caggccgagt     3120
ttcagggaga aactggaaga actttgccct ggttccccctt ctgagggatg caagcactcg     3180
agatagacat gccacccagc aggaagaagt tcaactgaag cattatacgg gttcccttaa     3240
gccagaggat gctgaggttt tcaaggattc catggtccca ggggagaaat aaaagcttgg     3300
```

-continued

```
atccaatcaa cctctggatt acaaaatttg tgaaagattg actggtattc ttaactatgt    3360
tgctcctttt acgctatgtg gatacgctgc tttaatgcct ttgtatcatg ctattgcttc    3420
ccgtatggct ttcattttct cctccttgta taaatcctgg ttgctgtctc tttatgagga    3480
gttgtggccc gttgtcaggc aacgtggcgt ggtgtgcact gtgtttgctg acgcaacccc    3540
cactggttgg ggcattgcca ccacctgtca gctcctttcc gggactttcg ctttccccct    3600
ccctattgcc acggcggaac tcatcgccgc ctgccttgcc cgctgctgga caggggctcg    3660
gctgttgggc actgacaatt ccgtggtgtt gtcgggggaag ctgacgtcct ttccatggct    3720
gctcgcctgt gttgccacct ggattctgcg cgggacgtcc ttctgctacg tcccttcggc    3780
cctcaatcca gcggaccttc cttcccgcgg cctgctgccg gctctgcggc ctcttccgcg    3840
tcttcgagat ctgcctcgac tgtgccttct agttgccagc catctgttgt ttgcccctcc    3900
cccgtgcctt ccttgaccct ggaaggtgcc actcccactg tcctttccta ataaaatgag    3960
gaaattgcat cgcattgtct gagtaggtgt cattctattc tggggggtgg ggtggggcag    4020
gacagcaagg gggaggattg ggaagacaat agcaggcatg ctggggactc gagttaaggg    4080
cgaattcccg attaggatct tcctagagca tggctacgta gataagtagc atggcgggtt    4140
aatcattaac tacaaggaac ccctagtgat ggagttggcc actccctctc tgcgcgctcg    4200
ctcgctcact gaggccgggc gaccaaaggt cgcccgacgc ccgggctttg cccgggcggc    4260
ctcagtgagc gagcgagcgc gcag                                           4284
```

<210> SEQ ID NO 2
<211> LENGTH: 4606
<212> TYPE: DNA
<213> ORGANISM: Mus musculus

<400> SEQUENCE: 2

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctacgta gccatgctct     180
aggaagatcg gaattcgccc ttaagctagg gttcttccca ttttggctac atggtctttt     240 ttttttacctt tttggttcct ttggcctttt ggcttttggc ttccagggct tctggatccc     300
ccccaacccc tcccatacac atacacatgt gcactcgtgc actcaaccca gcacaggata     360
atgttcattc ttgacctttc cacatacatc tggctatgtt ctctctctta tctacaataa     420
atctcctcca ctatacttag gagcagttat gttcttcttc tttctttctt tttttttttt     480
ttcattcagt aacatcatca gaatccccta gctctggcct acctcctcag taacaatcag     540
ctgatccctg gccactaatc tgtactcact aatctgtttt ccaaactctt ggcccctgag     600
ctaattatag cagtgcttca tgccacccac cccaacccta ttcttgttct ctgactccca     660
ctaatctaca cattcagagg attgtggata taagaggctg ggaggccagc ttagcaacca     720
gagctggagg atccatcaca ctggcggccg cgccaccatg aagaggagca tcctgaagtg     780
gttccagagc agggaccaga agcagcaccc cagcagctac gagggcgtgg tgtgcgaggc     840
cgacgcctgc agcgtggcca gccaggacgt gttcaaggtg atcagcgacg gcagcacctg     900
caggctgagg agcttcatca agaagaacag ggagggcctg aagaagctgg acaagctgaa     960
cgccaccccc ctgcaccacg ccgccggcaa gggccagctg gagctgatgc agatgatcat    1020
ggacgacagc agcttcgagg ccctgaacgt gaccgacagc agcggcaaca ccccccctgca   1080
```

-continued

```
ctgggccacc aagaagcagc agaccgagag cgtgaagctg ctgctgagca ggggcgccaa    1140
ccccaacatc ctgaacagca acatggtgag cccccctgcac tgggccgtgc agtacctgtg    1200
caacgacctg gtgaagatct tcctggagtg cagcatcacc gacgtgaacc tggagggcga    1260
gggcggcaac acccccatcc tggtggcctg ctacaaggac aacagcgagg ccctgaagct    1320
gctgatcgag aacggcggcg acatcgccaa ggccaacaac atgggctgca tgcccgtgca    1380
cgccgccgcc ttcagcggca gcaagctgtg cctggagatc atcatcaaga ggggcgtgga    1440
gctgggctac agccccgaga accacatcaa cttcaccaac aacggcaagt gcagccccct    1500
gcacctggcc gtgcagagca gggacctgga gatgatcaag atgtgcatcg agtacgcgc     1560 ccagatcgac ctgaagcaga acgacaactg caccgccctg cacttcgccg ccacccaggg    1620
cgccaccgag atcctgaagc tgatgatgag cagctacacc ggcgaggaga gcatcatcaa    1680
cgccctggac ggcaacaagg agaccctgct gcacagggcc gccctgttcg accaccacga    1740
gctggccgag tacctgatca gcaagggcgc caacatcaac agcgtggaca tcgagggcag    1800
gacccccctg ctgctggcca ccagctgcgc cagctggaag atcgtgaacc tgctgctgag    1860
caagggcgcc aacgtggagc tgaaggacct gctgggccac aacttcctgc acctgaccgt    1920
gctgcagccc ggcggcctgc agcacctgaa cgaggacttc ctgaagatga gcacatcag     1980 ggacctgatc accgaggagg accaggaggg ctgcacccccc ctgcactacg ccagcaagca    2040
gggcgtgccc ctgagcgtga acatcctgct ggagatgaac gtgagcgtgt acgccaagag    2100
cagggacaag aagagccccc tgcacttcgc cgccagctac ggcaggatca acacctgcct    2160
gaggctgctg gaggccatgg aggacaccag gctgctgaac gagggcgaca agaagggcat    2220
gacccccctg cacctggccg cccagaacgg ccacgagaag gtggtgcagt cctgctgaa     2280 gaagggcgcc ctgttcctgt gcgactacaa gggctggacc gccctgcacc acgccgcctt    2340
cggcggctac accaggacca tgcagatcat cctgaacacc aacatgaagg ccaccgacaa    2400
ggtgaacgac gagggcaaca ccgccctgca cctggccgcc agggaggggcc acgccaaggc    2460 cgtgaagctg ctgctggacg acaacgccaa gatcctgctg aacagcgccg aggccagctt    2520
cctgcacgag gccatccaca cggcaggaa ggacgtggtg aacgccgtga tcctgcacaa     2580
gaggtgggag gagagcatca ccaccttcag ccaccacagc agcatcaaca agtgcgccat    2640
cctggagatg gtggagtacc tgcccgagtg cctgaagctg gtgctggaca actgcatcat    2700
cgagagcccc gacgagaagg gcagcaagga cttctgcatc gagtacaact tcaggtacct    2760
gcagtgcccc ctgaagctga agaagaagtt caaggagaac gagggcatca tctacgagcc    2820
cctgctggcc ctgaacggca tggtgaggca acacgggtg gagctgctga gccacccgt     2880 gtgcaccgag tacctgctga tgaagtggat ggcctacggc ttcagggccc acatcctgaa    2940
cctggccgtg tacagcctgg gcctgatccc cctgaccctg ctggtgaccc acctggagcc    3000
cgacgtgtgc ttcaacgcca ccggcagcgg cagcggcttc gccaacgagc tgggcccccag    3060 gctgatgggc aagggcagcg gcctgaagta cggccccttc gacaacaagg acagcaactt    3120
catcaaggtg tgcatgagcc tggtgttcat catgagcctg ttcggcatct gcaaggagat    3180
catccagctg ttccagcaga gctgaacta cctgctggac tacagcaacc tgctggactg     3240
gaccatctac accaccagca tcatcttcgt gagcagcctg ttcgtgatgc tgcccatcag    3300
gctgcagtgg gactgcggcg ccatcgccat cctgctggcc tggaccaact tcctgctgta    3360
cctgcagagg ttcgagaact acggcatcta catcgtgatg ttctgggaga tcctgaggac    3420
cctgatcagg atcgtgatcg tgttcttctt cctgatgctg gccttcggcc tgagcttcta    3480
```

-continued

```
cgtgctgctg ggcagccagc agacctacgg cacccctac  ctgagcgtga tgcagacctt   3540
cagcatgatg atcggcgaca acaactacag ggaggccttc ctggagccca tgctggccga   3600
caagctgccc ttcccttcc  tgagcttcat catcctgatc atcttcagca tgctgatccc   3660
catcctgctg atgaacctgc tgatcggcct ggccgtgggc gacatcgccg aggtgcagaa   3720
gttcgccgcc atgaagagga tcgccatgca ggtgaacctg cacaccaacc tggagaagaa   3780
gctgccctac tggttcctga gcagggtgga ccaggagagc atcgtggtgt accccaacaa   3840
gcccaggtac tgcggcttca tgaccgtgtt ccagtactgc ttcggctggg acaacaccgc   3900
cgccgacacc cagagcgccg acaccaccct ggagctggag gtgctgaagc agaagtacag   3960
gctgaaggac atcgccgccc tggtggagaa gcagcacaac ctgctgaagc tggtggccca   4020
gaagatggag atcatgagcg aggccgagga cgaggacccc aacgacctgt ccagaacaa    4080 gttcaggaag gagcagctgg agcacaagaa cagcaagtgg gacaccgtgc tgaaggccgt   4140
gaagagcaag tgcgcctgat aaacgcgtgg atctgcctcg actgtgcctt ctagttgcca   4200
gccatctgtt gtttgcccct ccccgtgcc  ttccttgacc ctggaaggtg ccactcccac   4260
tgtcctttcc taataaaatg aggaaattgc atcgcattgt ctgagtaggt gtcattctat   4320 tctgggggt  ggggtggggc aggacagcaa gggggaggat tgggaagaca atagcaggca   4380 tgctgggac  tcgagttaag ggcgaattcc cgattaggat cttcctagag catggctacg   4440
tagataagta gcatggcggg ttaatcatta actacaagga accctagtg  atggagttgg   4500 ccactccctc tctgcgcgct cgctcgctca ctgaggccgg gcgaccaaag gtcgcccgac   4560
gcccgggctt tgcccgggcg gcctcagtga gcgagcgagc gcgcag             4606
```

```
<210> SEQ ID NO 3
<211> LENGTH: 4606
<212> TYPE: DNA
<213> ORGANISM: Mus musculus

<400> SEQUENCE: 3
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagg gttcttccca tttttggctac atggtctttt   240 tttttacctt tttggttcct ttggcctttt ggcttttggc ttccagggct tctggatccc    300
ccccaacccc tcccatacac atacacatgt gcactcgtgc actcaaccca gcacaggata    360
atgttcattc ttgacctttc cacatacatc tggctatgtt ctctctctta tctacaataa    420
atctcctcca ctatacttag gagcagttat gttcttcttc tttctttctt tttttttttt    480
ttcattcagt aacatcatca gaatcccta  gctctggcct acctcctcag taacaatcag    540
ctgatccctg gccactaatc tgtactcact aatctgtttt ccaaactctt ggccctgag     600 ctaattatag cagtgcttca tgccacccac cccaacccta ttcttgttct ctgactccca    660
ctaatctaca cattcagagg attgtggata taagaggctg ggaggccagc ttagcaacca    720
gagctggagg atccatcaca ctggcggccg cgccaccatg aagaggagca tcctgaagtg    780
gttccagagc agggaccaga agcagcaccc cagcagctac gagggcgtgg tgtgcgaggc    840
cgacgcctgc agcgtggcca gccaggacgt gttcaaggtg atcagcgacg gcagcacctg    900
caggctgagg agcttcatca agaagaacag ggagggcctg aagaagctgg acaagctgaa    960
```

-continued

```
cgccaccccc ctgcaccacg ccgccggcaa gggccagctg gagctgatgc agatgatcat    1020
ggacgacagc agcttcgagg ccctgaacgt gaccgacagc agcggcaaca cccccctgca    1080
ctgggccacc aagaagcagc agaccgagag cgtgaagctg ctgctgagca ggggcgccaa    1140
ccccaacatc ctgaacagca acatggtgag cccccctgcac tgggccgtgc agtacctgtg    1200
caacgacctg gtgaagatct tcctggagtg cagcatcacc gacgtgaacc tggagggcga    1260
gggcggcaac acccccatcc tggtggcctg ctacaaggac aacagcgagg ccctgaagct    1320
gctgatcgag aacggcggcg acatcgccaa ggccaacaac atgggctgca tgcccgtgca    1380
cgccgccgcc ttcagcggca gcaagctgtg cctggagatc atcatcaaga ggggcgtgga    1440
gctgggctac agccccgaga accacatcaa cttcaccaac aacggcaagt gcagccccct    1500
gcacctggcc gtgcagagca gggacctgga gatgatcaag atgtgcatcg agtacggcgc    1560
ccagatcgac ctgaagcaga cgacaactg caccgccctg cacttcgccg ccacccaggg    1620
cgccaccgag atcctgaagc tgatgatgag cagctacacc ggcgaggaga gcatcatcaa    1680
cgccctggac ggcaacaagg agaccctgct gcacagggcc gccctgttcg accaccacga    1740
gctggccgag tacctgatca gcaagggcgc caacatcaac agcgtggaca tcgagggcag    1800 gaccccctg ctgctggcca ccagctgcgc cagctggaag atcgtgaacc tgctgctgag    1860
caagggcgcc aacgtggagc tgaaggacct gctgggccac aacttcctgc acctgaccgt    1920
gctgcagccc ggcggcctgc agcacctgaa cgaggacttc ctgaagatga gcacatcag    1980 ggacctgatc accgaggagg accaggaggg ctgcaccccc ctgcactacg ccagcaagca    2040
gggcgtgccc ctgagcgtga acatcctgct ggagatgaac gtgagcgtgt acgccaagag    2100
cagggacaag aagagccccc tgcacttcgc cgccagctac ggcaggatca cacctgcct    2160 gaggctgctg gaggccatgg aggacaccag gctgctgaac gagggcgaca agaagggcat    2220 gaccccctg cacctggccg cccagaacgg ccacgagaag gtggtgcagt cctgctgaa    2280 gaagggcgcc ctgttcctgt gcgactacaa gggctggacc gccctgcacc acgccgcctt    2340
cggcggctac accaggacca tgcagatcat cctgaacacc aacatgaagg ccaccgacaa    2400
ggtgaacgac gagggcaaca ccgccctgca cctggccgcc agggagggcc acgccaaggc    2460
cgtgaagctg ctgctggacg acaacgccaa gatcctgctg aacagcgccg aggccagctt    2520
cctgcacgag gccatccaca cggcaggaa ggacgtggtg aacgccgtga tcctgcacaa    2580
gaggtgggag gagagcatca ccaccttcag ccaccacagc agcatcaaca agtgcgccat    2640
cctggagatg gtggagtacc tgcccgagtg cctgaagctg gtgctggaca actgcatcat    2700
cgagagcccc gacgagaagg gcagcaagga cttctgcatc gagtacaact tcaggtacct    2760
gcagtgcccc ctgaagctga agaagaagtt caaggagaac gagggcatca tctacgagcc    2820
cctgctggcc ctgaacggca tggtgaggca acagggtg gagctgctga gccacccgt    2880 gtgcaccgag tacctgctga tgaagtggat ggcctacggc ttcagggccc acatcctgaa    2940
cctggccgtg tacagcctgg gcctgatccc cctgaccctg ctggtgaccc acctggagcc    3000
cgacgtgtgc ttcaacgcca ccctgaagta cggcccccttc gacaacaagg acagcaactt    3060
catcaaggtg tgcatgagcc tggtgttcat catgagcctg ttcggcatct gcaaggagat    3120
catccagctg ttccagcaga agctgaacta cctgctggac tacagcaacc tgctggactg    3180
gaccatctac accaccagca tcatcttcgt gagcagcctg ttcgtgatgg cagcggcag    3240 cggcttcgcc aacgagctgg gcccccaggct gatgggcaag ggcagcggcc tgcccatcag    3300
gctgcagtgg gactgcggcg ccatcgccat cctgctggcc tggaccaact tcctgctgta    3360
```

```
cctgcagagg ttcgagaact acggcatcta catcgtgatg ttctgggaga tcctgaggac      3420
cctgatcagg atcgtgatcg tgttcttctt cctgatgctg gccttcggcc tgagcttcta      3480
cgtgctgctg ggcagccagc agacctacgg cacccccta c ctgagcgtga tgcagacctt      3540
cagcatgatg atcggcgaca caactacag g gaggccttc ctggagccca tgctggccga      3600
caagctgccc ttccccttcc tgagcttcat catcctgatc atcttcagca tgctgatccc      3660
catcctgctg atgaacctgc tgatcggcct ggccgtgggc gacatcgccg aggtgcagaa      3720
gttcgccgcc atgaagagga tcgccatgca ggtgaacctg cacaccaacc tggagaagaa      3780
gctgccctac tggttcctga gcaggtgga ccaggagagc atcgtggtgt accccaacaa      3840
gcccaggtac tgcggcttca tgaccgtgtt ccagtactgc ttcggctggg acaacaccgc      3900
cgccgacacc cagagcgccg acaccaccct ggagctggag gtgctgaagc agaagtacag      3960
gctgaaggac atcgccgccc tggtggagaa gcagcacaac ctgctgaagc tggtggccca      4020
gaagatggag atcatgagcg aggccgagga cgaggacccc aacgacctgt ccagaacaa      4080 gttcaggaag gagcagctgg agcacaagaa cagcaagtgg gacaccgtgc tgaaggccgt      4140
gaagagcaag tgcgcctgat aaacgcgtgg atctgcctcg actgtgcctt ctagttgcca      4200
gccatctgtt gtttgcccct cccccgtgcc ttccttgacc ctggaaggtg ccactcccac      4260
tgtcctttcc taataaaatg aggaaattgc atcgcattgt ctgagtaggt gtcattctat      4320
tctggggggt ggggtggggc aggacagcaa ggggggaggat tgggaagaca atagcaggca      4380
tgctggggac tcgagttaag ggcgaattcc cgattaggat cttcctagag catggctacg      4440
tagataagta gcatggcggg ttaatcatta actacaagga accctagtg atggagttgg      4500 ccactccctc tctgcgcgct cgctcgctca ctgaggccgg gcgaccaaag gtcgcccgac      4560
gcccgggctt tgcccgggcg gcctcagtga gcgagcgagc gcgcag                     4606
```

```
<210> SEQ ID NO 4
<211> LENGTH: 4197
<212> TYPE: DNA
<213> ORGANISM: Mus musculus

<400> SEQUENCE: 4
```

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggggtccc tgcggccgca cgcgtcgtgg tacctctggt cgttacataa       180
cttacggtaa atggcccgcc tggctgaccg cccaacgacc cccgcccatt gacgtcaata       240
atgacgtatg ttcccatagt aacgccaata gggactttcc attgacgtca atgggtggag       300
tatttacggt aaactgccca cttggcagta catcaagtgt atcatatgcc aagtacgccc       360
cctattgacg tcaatgacgg taaatggccc gcctggcatt atgcccagta catgacctta       420
tgggactttc ctacttggca gtacattact cgaggccacg ttctgcttca ctctccccat       480 ctccccccc ctccccaccc ccaattttgt atttatttat tttttaatta ttttgtgcag       540 cgatggggg ggggggggg ggggggcgcg cgccaggcgg ggcggggcgg ggcgagggc         600 ggggcgggc gaggcggaga ggtgcggcgg cagccaatca gagcggcgcg ctccgaaagt       660
ttccttttat ggcgaggcgg cggcggcggc ggccctataa aaagcgaagc gcgcggcggg       720
cgggagcggg atcagccacc gcggtggcgg cctagagtcg acgaggaact gaaaaaccag       780
aaagttaact ggtaagttta gtctttttgt cttttatttc aggtcccgga tccggtggtg       840
```

-continued

```
gtgcaaatca aagaactgct cctcagtgga tgttgccttt acttctaggc ctgtacggaa      900
gtgttacttc tgctctaaaa gctgcggaat tgtacccgcg gccgatccac cggtcgcatc      960
gatgccacca tggaacaacg ggctagctta gactcagagg agtctgagtc cccacccaa      1020 gagaactcct gcctggaccc tccagacaga gaccctaact gcaagccacc tccagtcaag      1080
ccccacatct tcactaccag gagtcgtacc cggcttttg ggaagggtga ctcggaggag       1140
gcctctcccc tggactgccc ttatgaggaa ggcgggctgg cttcctgccc tatcatcact      1200
gtcagctctg ttctaactat ccagaggcct ggggatggac ctgccagtgt caggccgtca      1260
tcccaggact ccgtctccgc tggtgagaag cccccgaggc tctatgatcg caggagcatc      1320
ttcgatgctg tggctcagag taactgccag gagctggaga gcctgctgcc cttcctgcag      1380
aggagcaaga agcgcctgac tgacagcgag ttcaaagacc cagagacagg aaagacctgt      1440
ctgctaaaag ccatgctcaa tctgcacaat gggcagaatg acaccatcgc tctgctcctg      1500
gacgttgccc ggaagacaga cagcctgaag cagtttgtca atgccagcta cacagacagc      1560
tactacaagg gccagacagc actgcacatt gccattgaac ggcggaacat gacgctggtg      1620
accctcttgg tggagaatgg agcagatgtc caggctgcgg ctaacgggga cttcttcaag      1680
aaaaccaaag ggaggcctgg cttctacttt ggtgagctgc ccctgtccct ggctgcgtgc      1740
accaaccagc tggccattgt gaagttcctg ctgcagaact cctggcagcc tgcagacatc      1800
agcgcccggg actcagtggg caacacggtg cttcatgccc tggtggaggt ggcagataac      1860
acagttgaca acaccaagtt cgtgacaagc atgtacaacg agatcttgat cctgggggcc      1920
aaactccacc ccacgctgaa gctggaagag atcaccaaca ggaaggggct cacgccactg      1980
gctctggctg ctagcagtgg gaagatcggg gtcttggcct acattctcca gagggagatc      2040
catgaacccg agtgccgaca cctatccagg aagttcaccg aatgggccta tgggccagtg      2100
cactcctccc tttatgacct gtcctgcatt gacacctgtg aaaagaactc ggttctggag      2160
gtgatcgctt acagcagcag tgagacccct aaccgtcatg acatgcttct cgtggaaccc      2220
ttgaaccgac tcctacagga caagtgggac agatttgtca agcgcatctt ctacttcaac      2280
ttcttcgtct actgcttgta tatgatcatc ttcaccgcgg ctgcctacta tcggcctgtg      2340
gaaggcttgc cccctataa gctgcaccac caccaccacc acaaaaacac cgttgggggac      2400 tatttccgag tcaccggaga gatcttgtct gtgtcaggag gagtctactt cttcttccga      2460
gggattcaat atttcctgca gaggcgacca tccctcaaga gtttgtttgt ggacagctac      2520
agtgagatac ttttctttgt acagtcgctg ttcatgctgg tgtctgtggt actgtacttc      2580
agccaacgca aggagtatgt ggcttccatg gtgttctccc tggccatggg ctggaccaac      2640 atgtctctact ataccegagg attccagcag atgggcatct atgctgtcat gattgagaag     2700
atgatcctca gagacctgtg ccggtttatg ttcgtctacc tcgtgttctt gtttggattt      2760
tccacagctg tggtgacact gattgaggat gggaagaata actctctgcc tatggagtcc      2820
acaccacaca agtgccgggg gtctgcctgc aagccaggta actcttacaa cagcctgtat      2880
tccacatgtc tggagctgtt caagttcacc atcggcatgg gcgacctgga gttcactgag      2940
aactacgact tcaaggctgt cttcatcatc ctgttactgg cctatgtgat tctcacctac      3000
atccttctgc tcaacatgct cattgctctc atgggtgaga ccgtcaacaa gattgcacaa      3060
gagagcaaga acatctggaa gctgcagaga gccatcacca tcctggatac agagaagagc      3120
ttcctgaagt gcatgaggaa ggccttccgc tctggcaagc tgctgcaggt ggggttcact      3180
cctgacggca aggatgacta ccggtggtgt ttcagggtgg acgaggtaaa ctggactacc      3240
```

-continued

```
tggaacacca atgtgggtat catcaacgag acccaggca actgtgaggg cgtcaagcgc      3300
accctgagct tctccctgag gtcaggccga gtttcaggga gaaactggaa gaactttgcc      3360
ctggttcccc ttctgaggga tgcaagcact cgagatagac atgccaccca gcaggaagaa      3420
gttcaactga agcattatac gggttccctt aagccagagg atgctgaggt tttcaaggat      3480
tccatggtcc caggggagaa ataaaagctt gcctcgagca gcgctgctcg agagatctac      3540
gggtggcatc cctgtgaccc ctccccagtg cctctcctgg ccctggaagt tgccactcca      3600
gtgcccacca gccttgtcct aataaaatta agttgcatca ttttgtctga ctaggtgtcc      3660
ttctataata ttatggggtg gaggggggtg gtatggagca aggggcaagt tgggaagaca      3720
acctgtaggg cctgcggggt ctattgggaa ccaagctgga gtgcagtggc acaatcttgg      3780
ctcactgcaa tctccgcctc ctgggttcaa gcgattctcc tgcctcagcc tcccgagttg      3840
ttgggattcc aggcatgcat gaccaggctc agctaatttt tgttttttt gtagagacgg      3900 ggtttcacca tattggccag gctggtctcc aactcctaat ctcaggtgat ctacccacct      3960
tggcctccca aattgctggg attacaggcg tgaaccactg ctcccttccc tgtccttctg      4020
attttgtagg taaccacgtg cggaccgagc ggccgcagga acccctagtg atggagttgg      4080
ccactccctc tctgcgcgct cgctcgctca ctgaggccgg gcgaccaaag gtcgcccgac      4140
gcccgggctt tgcccgggcg gcctcagtga gcgagcgagc gcgcagctgc ctgcagg       4197
```

<210> SEQ ID NO 5
<211> LENGTH: 6056
<212> TYPE: DNA
<213> ORGANISM: Mus musculus

<400> SEQUENCE: 5

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc tgcggccgca cgcgtaagct ttgcaaagat ggataaagtt       180
ttaaacagag aggaatcttt gcagctaatg gaccttctag gtcttgaaag gagtgggaat       240
tggctccggt gcccgtcagt gggcagagcg cacatcgccc acagtccccg agaagttggg       300 gggagggggtc ggcaattgaa ccggtgccta gagaaggtgg cgcggggtaa actgggaaag       360
tgatgtcgtg tactggctcc gccttttttcc cgagggtggg ggagaaccgt atataagtgc       420
agtagtcgcc gtgaacgttc tttttcgcaa cgggtttgcc gccagaacac aggtaagtgc       480
cgtgtgtggt tcccgcgggc ctggcctctt tacgggttat ggcccttgcg tgccttgaat       540
tacttccact ggctgcagta cgtgattctt gatcccgagc ttcgggttgg aagtgggtgg       600
gagagttcga ggccttgcgc ttaaggagcc ccttcgcctc gtgcttgagt tgaggcctgg       660
cctgggcgct ggggccgccg cgtgcgaatc tggtggcacc ttcgcgcctg tctcgctgct       720
ttcgataagt ctctagccat ttaaaatttt tgatgacctg ctgcgacgct ttttttctgg       780
caagatagtc ttgtaaatgc gggccaagat ctgcacactg gtatttcggt ttttggggcc       840
gcgggcggcg acggggcccg tgcgtcccag cgcacatgtt cggcgaggcg gggcctgcga       900
gcgcggccac cgagaatcgg acggggggtag tctcaagctg gccggcctgc tctggtgcct       960
ggcctcgcgc cgccgtgtat cgccccgccc tgggcggcaa ggctggcccg gtcggcacca      1020
gttgcgtgag cggaaagatg gccgcttccc ggccctgctg cagggagctc aaaatggagg      1080
acgcggcgct cgggagagcg ggcgggtgag tcacccacac aaaggaaaag ggcctttccg      1140
```

-continued

```
tcctcagccg tcgcttcatg tgactccacg gagtaccggg cgccgtccag gcacctcgat   1200
tagttctcga gctttggag tacgtcgtct ttaggttggg gggagggtt ttatgcgatg     1260 gagtttcccc acactgagtg ggtggagact gaagttaggc cagcttggca cttgatgtaa   1320
ttctccttgg aatttgccct ttttgagttt ggatcttggt tcattctcaa gcctcagaca   1380
gtggttcaaa gttttttct tccatttcag gtgtcgtgag gtaccggcgg ccgcgccacc    1440
atggaacaac gggctagctt agactcagag gagtctgagt ccccaccca agagaactcc    1500 tgcctggacc ctccagacag agaccctaac tgcaagccac ctccagtcaa gccccacatc    1560
ttcactacca ggagtcgtac ccggcttttt gggaagggtg actcggagga ggcctctccc    1620
ctggactgcc cttatgagga aggcgggctg gcttcctgcc ctatcatcac tgtcagctct   1680
gttctaacta tccagaggcc tggggatgga cctgccagtg tcaggccgtc atcccaggac    1740
tccgtctccg ctggtgagaa gcccccgagg ctctatgatc gcaggagcat cttcgatgct   1800
gtggctcaga gtaactgcca ggagctggag agcctgctgc ccttcctgca gaggagcaag   1860
aagcgcctga ctgacagcga gttcaaagac ccagagacag gaaagacctg tctgctaaaa   1920
gccatgctca atctgcacaa tgggcagaat gacaccatcg ctctgctcct ggacgttgcc    1980
cggaagacag acagcctgaa gcagtttgtc aatgccagct acacagacag ctactacaag    2040
ggccagacag cactgcacat tgccattgaa cggcggaaca tgacgctggt gaccctcttg    2100
gtggagaatg gagcagatgt ccaggctgcg gctaacgggg acttcttcaa gaaaaccaaa    2160
gggaggcctg gcttctactt tggtgagctg ccctgtccc tggctgcgtg caccaaccag    2220
ctggccattg tgaagttcct gctgcagaac tcctggcagc ctgcagacat cagcgcccgg    2280
gactcagtgg gcaacacggt gcttcatgcc ctggtggagg tggcagataa cacagttgac    2340
aacaccaagt tcgtgacaag catgtacaac gagatcttga tcctgggggc caaactccac    2400
cccacgctga agctggaaga gatcaccaac aggaaggggc tcacgccact ggctctggct    2460
gctagcagtg ggaagatcgg ggtcttggcc tacattctcc agagggagat ccatgaaccc    2520
gagtgccgac acctatccag gaagttcacc gaatgggcct atgggccagt gcactcctcc    2580
ctttatgacc tgtcctgcat tgacacctgt gaaaagaact cggttctgga ggtgatcgct    2640
tacagcagca gtgagacccc taaccgtcat gacatgcttc tcgtggaacc cttgaaccga    2700
ctcctacagg acaagtggga cagatttgtc aagcgcatct tctacttcaa cttcttcgtc    2760
tactgcttgt atatgatcat cttcaccgcg gctgcctact atcggcctgt ggaaggcttg    2820
cccccctata agctgaaaaa caccgttggg gactatttcc gagtcaccgg agagatcttg    2880
tctgtgtcag gaggagtcta cttcttcttc cgagggattc aatatttcct gcagaggcga    2940
ccatccctca agagtttgtt tgtggacagc tacagtgaga tactttctt tgtacagtcg    3000 ctgttcatgc tggtgtctgt ggtactgtac ttcagccaac gcaaggagta tgtggcttcc    3060
atggtgttct ccctggccat gggctggacc aacatgctct actatacccg aggattccag    3120
cagatgggca tctatgctgt catgattgag aagatgatcc tcagagacct gtgccggttt    3180
atgttcgtct acctcgtgtt cttgtttgga ttttccacag ctgtggtgac actgattgag    3240
gatgggaaga taactctct gcctatggag tccacaccac acaagtgccg ggggtctgcc    3300
tgcaagccag gtaactctta caacagcctg tattccacat gtctggagct gttcaagttc    3360
accatcggca tgggcgacct ggagttcact gagaactacg acttcaaggc tgtcttcatc    3420
atcctgttac tggcctatgt gattctcacc tacatccttc tgctcaacat gctcattgct    3480 ctcatggggtg agaccgtcaa caagattgca caagagagca agaacatctg gaagctgcag    3540
```

-continued

```
agagccatca ccatcctgga tacagagaag agcttcctga agtgcatgag gaaggccttc   3600
cgctctggca agctgctgca ggtggggttc actcctgacg gcaaggatga ctaccggtgg   3660
tgtttcaggg tggacgaggt aaactggact acctggaaca ccaatgtggg tatcatcaac   3720
gaggacccag gcaactgtga gggcgtcaag cgcaccctga gcttctccct gaggtcaggc   3780
cgagtttcag ggagaaactg gaagaacttt gccctggttc cccttctgag ggatgcaagc   3840
actcgagata gacatgccac ccagcaggaa gaagttcaac tgaagcatta tacgggatcc   3900
cttaagccag aggatgctga ggttttcaag gattccatgg tcccagggga gaaactcgag   3960
ggcagaggaa gtcttctaac atgcggtgac gtggaggaga atcccggccc tgcaccggga   4020
tccaccatgg tgagcaaggg cgaggagctg ttcaccgggg tggtgcccat cctggtcgag   4080
ctggacggcg acgtaaacgg ccacaagttc agcgtgtccg gcgagggcga gggcgatgcc   4140
acctacggca agctgaccct gaagttcatc tgcaccaccg gcaagctgcc cgtgccctgg   4200
cccaccctcg tgaccaccct gacctacggc gtgcagtgct tcagccgcta ccccgaccac   4260
atgaagcagc acgacttctt caagtccgcc atgcccgaag ctacgtcca ggagcgcacc   4320 atcttcttca aggacgacgg caactacaag acccgcgccg aggtgaagtt cgagggcgac   4380
accctggtga accgcatcga gctgaagggc atcgacttca aggaggacgg caacatcctg   4440
gggcacaagc tggagtacaa ctacaacagc cacaacgtct atatcatggc cgacaagcag   4500
aagaacggca tcaaggtgaa cttcaagatc cgccacaaca tcgaggacgg cagcgtgcag   4560
ctcgccgacc actaccagca gaacacccc atcggcgacg ccccgtgct gctgcccgac   4620 aaccactacc tgagcaccca gtccgccctg agcaaagacc ccaacgagaa gcgcgatcac   4680
atggtcctgc tggagttcgt gaccgccgcc gggatcactc tcggcatgga cgagctgtac   4740
aagtgataaa agcttgaatt cgatatcaag cttatcgata tcaacctct ggattacaaa   4800 atttgtgaaa gattgactgg tattcttaac tatgttgctc cttttacgct atgtggatac   4860
gctgctttaa tgcctttgta tcatgctatt gcttcccgta tggctttcat tttctcctcc   4920
ttgtataaat cctggttgct gtctctttat gaggagttgt ggcccgttgt caggcaacgt   4980
ggcgtggtgt gcactgtgtt tgctgacgca accccactg gttggggcat tgccaccacc   5040
tgtcagctcc tttccgggac tttcgctttc ccctcccta ttgccacggc ggaactcatc   5100
gccgcctgcc ttgcccgctg ctggacaggg gctcggctgt tgggcactga caattccgtg   5160
gtgttgtcgg ggaaatcatc gtcctttcct tggctgctcg cctatgttgc cacctggatt   5220
ctgcgcggga cgtccttctg ctacgtccct tcggccctca atccagcgga ccttccttcc   5280
cgcggcctgc tgccggctct gcggcctctt ccgcgtcttc gccttcgccc tcagacgagt   5340
cggatctccc tttgggccgc ctccccgcat cgataccgag cgctgctcga gagatctacg   5400
ggtggcatcc ctgtgacccc tccccagtgc ctctcctggc cctggaagtt gccactccag   5460
tgcccaccag ccttgtccta ataaaattaa gttgcatcat tttgtctgac taggtgtcct   5520
tctataatat tatgggtgg aggggggtgg tatggagcaa ggggcaagtt gggaagacaa   5580
cctgtagggc ctgcggggtc tattgggaac caagctggag tgcagtggca caatcttggc   5640
tcactgcaat ctccgcctcc tgggttcaag cgattctcct gcctcagcct cccgagttgt   5700
tgggattcca ggcatgcatg accaggctca gctaattttt gtttttttgg tagagacggg   5760
gtttcaccat attggccagg ctggtctcca actcctaatc tcaggtgatc tacccacctt   5820
ggcctcccaa attgctggga ttacaggcgt gaaccactgc tcccttccct gtccttctga   5880
```

-continued

```
ttttgtaggt aaccacgtgc ggaccgagcg gccgcaggaa cccctagtga tggagttggc     5940
cactccctct ctgcgcgctc gctcgctcac tgaggccggg cgaccaaagg tcgcccgacg     6000
cccgggcttt gcccgggcgg cctcagtgag cgagcgagcg cgcagctgcc tgcagg        6056

<210> SEQ ID NO 6
<211> LENGTH: 6059
<212> TYPE: DNA
<213> ORGANISM: Mus musculus

<400> SEQUENCE: 6
cctgcaggca gctgcgcgct cgctcgctca ctgaggccgc ccgggcaaag cccgggcgtc       60
gggcgacctt tggtcgcccg gcctcagtga gcgagcgagc gcgcagagag ggagtggcca      120
actccatcac taggggttcc tgcggccgca cgcgtaagct ttgcaaagat ggataaagtt      180
ttaaacagag aggaatcttt gcagctaatg gaccttctag gtcttgaaag gagtgggaat      240
tggctccggt gcccgtcagt gggcagagcg cacatcgccc acagtccccg agaagttggg      300
gggaggggtc ggcaattgaa ccggtgccta gagaaggtgg cgcggggtaa actgggaaag      360
tgatgtcgtg tactggctcc gccttttttcc cgagggtggg ggagaaccgt atataagtgc      420
agtagtcgcc gtgaacgttc ttttttcgcaa cgggtttgcc gccagaacac aggtaagtgc      480
cgtgtgtggt tcccgcgggc ctggcctctt tacgggttat ggcccttgcg tgccttgaat      540
tacttccact ggctgcagta cgtgattctt gatcccgagc ttcgggttgg aagtgggtgg      600
gagagttcga ggccttgcgc ttaaggagcc ccttcgcctc gtgcttgagt tgaggcctgg      660
cctgggcgct ggggccgccg cgtgcgaatc tggtggcacc ttcgcgcctg tctcgctgct      720
ttcgataagt ctctagccat ttaaaatttt tgatgacctg ctgcgacgct ttttttctgg      780
caagatagtc ttgtaaatgc gggccaagat ctgcacactg gtatttcggt ttttggggcc      840
gcgggcggcg acgggcccg tgcgtcccag cgcacatgtt cggcgaggcg gggcctgcga      900
gcgcggccac cgagaatcgg acgggggtag tctcaagctg gccggcctgc tctggtgcct      960
ggcctcgcgc cgccgtgtat cgccccgccc tgggcggcaa ggctggcccg gtcggcacca     1020
gttgcgtgag cggaaagatg gccgcttccc ggccctgctg cagggagctc aaaatggagg     1080
acgcggcgct cgggagagcg ggcgggtgag tcacccacac aaaggaaaag ggcctttccg     1140
tcctcagccg tcgcttcatg tgactccacg gagtaccggg cgccgtccag gcacctcgat     1200
tagttctcga gcttttggag tacgtcgtct ttaggttggg gggaggggtt ttatgcgatg     1260
gagtttcccc acactgagtg ggtggagact gaagttaggc cagcttggca cttgatgtaa     1320
ttctccttgg aatttgccct ttttgagttt ggatcttggt tcattctcaa gcctcagaca     1380
gtggttcaaa gtttttttct tccatttcag gtgtcgtgag gtaccggcgg ccgcgccacc     1440
atggaacaac gggctagctt agactcagag gagtctgagt ccccacccca agagaactcc     1500
tgcctggacc ctccagacag agaccctaac tgcaagccac ctccagtcaa gccccacatc     1560
ttcactacca ggagtcgtac ccggcttttt gggaagggtg actcggagga ggcctctccc     1620
ctggactgcc cttatgagga aggcgggctg gcttcctgcc ctatcatcac tgtcagctct     1680
gttctaacta tccagaggcc tggggatgga cctgccagtg tcaggccgtc atcccaggac     1740
tccgtctccg ctggtgagaa gccccgagg ctctatgatc gcaggagcat cttcgatgct     1800
gtggctcaga gtaactgcca ggagctggag agcctgctgc ccttcctgca gaggagcaag     1860
aagcgcctga ctgacagcga gttcaaagac ccagagacag gaaagacctg tctgctaaaa     1920
gccatgctca atctgcacaa tgggcagaat gacaccatcg ctctgctcct ggacgttgcc     1980
```

-continued

```
cggaagacag acagcctgaa gcagtttgtc aatgccagct acacagacag ctactacaag     2040
ggccagacag cactgcacat tgccattgaa cggcggaaca tgacgctggt gaccctcttg     2100
gtggagaatg gagcagatgt ccaggctgcg gctaacgggg acttcttcaa gaaaaccaaa     2160
gggaggcctg gcttctactt tggtgagctg cccctgtccc tggctgcgtg caccaaccag     2220
ctggccattg tgaagttcct gctgcagaac tcctggcagc ctgcagacat cagcgcccgg     2280
gactcagtgg gcaacacggt gcttcatgcc ctggtggagg tggcagataa cacagttgac     2340
aacaccaagt tcgtgacaag catgtacaac gagatcttga tcctgggggc caaactccac     2400
cccacgctga agctggaaga gatcaccaac aggaaggggc tcacgccact ggctctggct     2460
gctagcagtg ggaagatcgg ggtcttggcc tacattctcc agagggagat ccatgaaccc     2520
gagtgccgac acctatccag gaagttcacc gaatgggcct atgggccagt gcactcctcc     2580
ctttatgacc tgtcctgcat tgacacctgt gaaaagaact cggttctgga ggtgatcgct     2640
tacagcagca gtgagacccc taaccgtcat gacatgcttc tcgtggaacc cttgaaccga     2700
ctcctacagg acaagtggga cagatttgtc aagcgcatct tctacttcaa cttcttcgtc     2760
tactgcttgt atatgatcat cttcaccgcg gctgcctact atcggcctgt ggaaggccac     2820
caccaccacc accacttgcc cccctataag ctgaaaaaca ccgttgggga ctatttccga     2880
gtcaccggag agatcttgtc tgtgtcagga ggagtctact tcttcttccg agggattcaa     2940
tatttcctgc agaggcgacc atccctcaag agtttgtttg tggacagcta cagtgagata     3000 ctttttctttg tacagtcgct gttcatgctg gtgtctgtgg tactgtactt cagccaacgc     3060
aaggagtatg tggcttccat ggtgttctcc ctggccatgg gctggaccaa catgctctac     3120
tatacccgag gattccagca gatgggcatc tatgctgtca tgattgagaa gatgatcctc     3180
agagacctgt gccggtttat gttcgtctac ctcgtgttct tgtttggatt ttccacagct     3240
gtggtgacac tgattgagga tgggaagaat aactctctgc ctatggagtc cacaccacac     3300
aagtgccggg ggtctgcctg caagccaggt aactcttaca acagcctgta ttccacatgt     3360
ctggagctgt tcaagttcac catcggcatg ggcgacctgg agttcactga gaactacgac     3420
ttcaaggctg tcttcatcat cctgttactg gcctatgtga ttctcaccta catccttctg     3480
ctcaacatgc tcattgctct catgggtgag accgtcaaca agattgcaca agagagcaag     3540
aacatctgga agctgcagag agccatcacc atcctggata cagagaagag cttcctgaag     3600
tgcatgagga aggccttccg ctctggcaag ctgctgcagg tggggttcac tcctgacggc     3660
aaggatgact accggtggtg tttcagggtg gacgaggtaa actggactac ctggaacacc     3720
aatgtgggta tcatcaacga ggacccaggc aactgtgagg gcgtcaagcg caccctgagc     3780
ttctccctga ggtcaggccg agtttcaggg agaaactgga agaactttgc cctggttccc     3840
cttctgaggg atgcaagcac tcgagataga catgccaccc agcaggaaga agttcaactg     3900
aagcattata cggggttccct taagccagag gatgctgagg ttttcaagga ttccatggtc     3960
ccaggggaga aactcgaggg cagaggaagt cttctaacat gcggtgacgt ggaggagaat     4020
cccggccctg caccgggatc caccatggtg agcaagggcg aggaggataa catggccatc     4080
atcaaggagt tcatgcgctt caaggtgcac atggagggcc cgtgaacgg ccacgagttc     4140 gagatcgagg gcgagggcga gggccgcccc tacgagggca cccagaccgc caagctgaag     4200
gtgaccaagg gtggccccct gcccttcgcc tgggacatcc tgtcccctca gttcatgtac     4260
ggctccaagg cctacgtgaa gcaccccgcc gacatccccg actacttgaa gctgtccttc     4320
```

-continued

```
cccgagggct tcaagtggga gcgcgtgatg aacttcgagg acggcggcgt ggtgaccgtg    4380
acccaggact cctccctgca ggacggcgag ttcatctaca aggtgaagct gcgcggcacc    4440
aacttcccct ccgacggccc cgtaatgcag aagaagacca tgggctggga ggcctcctcc    4500
gagcggatgt accccgagga cggcgccctg aagggcgaga tcaagcagag gctgaagctg    4560
aaggacggcg gccactacga cgctgaggtc aagaccacct acaaggccaa gaagcccgtg    4620
cagctgcccg gcgcctacaa cgtcaacatc aagttggaca tcacctccca caacgaggac    4680
tacaccatcg tggaacagta cgaacgcgcc gagggccgcc actccaccgg cggcatggac    4740
gagctgtaca gtaatgagaa attcgatatc aagcttatcg ataatcaacc tctggattac    4800
aaaatttgtg aaagattgac tggtattctt aactatgttg ctccttttac gctatgtgga    4860
tacgctgctt taatgccttt gtatcatgct attgcttccc gtatggcttt cattttctcc    4920
tccttgtata aatcctggtt gctgtctctt tatgaggagt tgtggcccgt tgtcaggcaa    4980
cgtggcgtgg tgtgcactgt gtttgctgac gcaaccccca ctggttgggg cattgccacc    5040
acctgtcagc tcctttccgg actttcgct ttccccctcc ctattgccac ggcggaactc    5100
atcgccgcct gccttgcccg ctgctggaca ggggctcggc tgttgggcac tgacaattcc    5160
gtggtgttgt cggggaaatc atcgtccttt ccttggctgc tcgcctatgt tgccacctgg    5220
attctgcgcg ggacgtcctt ctgctacgtc ccttcggccc tcaatccagc ggaccttcct    5280
tcccgcggcc tgctgccggc tctgcggcct cttccgcgtc ttcgccttcg ccctcagacg    5340
agtcggatct ccctttgggc cgcctccccg catcgatacc gagcgctgct cgagagatct    5400
acgggtggca tccctgtgac ccctccccag tgcctctcct ggccctggaa gttgccactc    5460
cagtgcccac cagccttgtc ctaataaaat taagttgcat cattttgtct gactaggtgt    5520
ccttctataa tattatgggg tggaggggggg tggtatggag caaggggcaa gttgggaaga    5580
caacctgtag ggcctgcggg gtctattggg aaccaagctg gagtgcagtg gcacaatctt    5640
ggctcactgc aatctccgcc tcctgggttc aagcgattct cctgcctcag cctcccgagt    5700
tgttgggatt ccaggcatgc atgaccaggc tcagctaatt tttgtttttt tggtagagac    5760
ggggtttcac catattggcc aggctggtct ccaactccta atctcaggtg atctacccac    5820
cttggcctcc caaattgctg ggattacagg cgtgaaccac tgctcccttc cctgtccttc    5880
tgattttgta ggtaaccacg tgcggaccga gcggccgcag gaacccctag tgatggagtt    5940
ggccactccc tctctgcgcg ctcgctcgct cactgaggcc gggcgaccaa aggtcgcccg    6000
acgcccgggc tttgcccggg cggcctcagt gagcgagcga gcgcgcagct gcctgcagg     6059
```

<210> SEQ ID NO 7
<211> LENGTH: 6059
<212> TYPE: DNA
<213> ORGANISM: Mus musculus

<400> SEQUENCE: 7

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc tgcggccgca cgcgtaagct ttgcaaagat ggataaagtt     180
ttaaacagag aggaatcttt gcagctaatg gaccttctag gtcttgaaag gagtgggaat     240
tggctccggt gcccgtcagt gggcagagcg cacatcgccc acagtccccg agaagttggg     300 gggagggggtc ggcaattgaa ccggtgccta gagaaggtgg cgcggggtaa actgggaaag     360
tgatgtcgtg tactggctcc gcctttttcc cgagggtggg ggagaaccgt atataagtgc     420
```

-continued

```
agtagtcgcc gtgaacgttc tttttcgcaa cgggtttgcc gccagaacac aggtaagtgc    480
cgtgtgtggt tcccgcgggc ctggcctctt tacgggttat ggcccttgcg tgccttgaat    540
tacttccact ggctgcagta cgtgattctt gatcccgagc ttcgggttgg aagtgggtgg    600
gagagttcga ggccttgcgc ttaaggagcc ccttcgcctc gtgcttgagt tgaggcctgg    660
cctgggcgct ggggccgccg cgtgcgaatc tggtggcacc ttcgcgcctg tctcgctgct    720
ttcgataagt ctctagccat ttaaaatttt tgatgacctg ctgcgacgct ttttttctgg    780
caagatagtc ttgtaaatgc gggccaagat ctgcacactg gtatttcggt ttttggggcc    840
gcgggcggcg acggggcccg tgcgtcccag cgcacatgtt cggcgaggcg gggcctgcga    900
gcgcggccac cgagaatcgg acgggggtag tctcaagctg gccggcctgc tctggtgcct    960
ggcctcgcgc cgccgtgtat cgccccgccc tgggcggcaa ggctggcccg gtcggcacca   1020
gttgcgtgag cggaaagatg gccgcttccc ggccctgctg cagggagctc aaaatggagg   1080
acgcggcgct cgggagagcg ggcgggtgag tcacccacac aaaggaaaag ggcctttccg   1140
tcctcagccg tcgcttcatg tgactccacg gagtaccggg cgccgtccag gcacctcgat   1200
tagttctcga gcttttggag tacgtcgtct ttaggttggg gggaggggtt ttatgcgatg   1260
gagtttcccc acactgagtg ggtggagact gaagttaggc cagcttggca cttgatgtaa   1320
ttctccttgg aatttgccct tttttgagttt ggatcttggt tcattctcaa gcctcagaca   1380
gtggttcaaa gttttttttct tccatttcag gtgtcgtgag gtaccggcgg ccgcgccacc   1440
atggaacaac gggctagctt agactcagag gagtctgagt ccccacccca agagaactcc   1500
tgcctggacc ctccagacag agaccctaac tgcaagccac ctccagtcaa gccccacatc   1560
ttcactacca ggagtcgtac ccggcttttt gggaagggtg actcggagga ggcctctccc   1620
ctggactgcc cttatgagga aggcgggctg gcttcctgcc ctatcatcac tgtcagctct   1680
gttctaacta tccagaggcc tggggatgga cctgccagtg tcaggccgtc atcccaggac   1740
tccgtctccg ctggtgagaa gccccgagg ctctatgatc gcaggagcat cttcgatgct   1800
gtggctcaga gtaactgcca ggagctggag agcctgctgc ccttcctgca gaggagcaag   1860
aagcgcctga ctgacagcga gttcaaagac ccagagacag gaaagacctg tctgctaaaa   1920
gccatgctca atctgcacaa tgggcagaat gacaccatcg ctctgctcct ggacgttgcc   1980
cggaagacag acagcctgaa gcagtttgtc aatgccagct acacagacag ctactacaag   2040
ggccagacag cactgcacat tgccattgaa cggcggaaca tgacgctggt gaccctcttg   2100
gtggagaatg gagcagatgt ccaggctgcg gctaacgggg acttcttcaa gaaaaccaaa   2160
gggaggcctg gcttctactt tggtgagctg cccctgtccc tggctgcgtg caccaaccag   2220
ctggccattg tgaagttcct gctgcagaac tcctggcagc ctgcagacat cagcgcccgg   2280
gactcagtgg gcaacacggt gcttcatgcc ctggtggagg tggcagataa cacagttgac   2340
aacaccaagt tcgtgacaag catgtacaac gagatcttga tcctgggggc caaactccac   2400
cccacgctga agctggaaga gatcaccaac aggaaggggc tcacgccact ggctctggct   2460
gctagcagtg ggaagatcgg ggtcttggcc tacattctcc agagggagat ccatgaaccc   2520
gagtgccgac acctatccag gaagttcacc gaatgggcct atgggccagt gcactcctcc   2580
ctttatgacc tgtcctgcat tgacacctgt gaaaagaact cggttctgga ggtgatcgct   2640
tacagcagca gtgagacccc taaccgtcat gacatgcttc tcgtggaacc cttgaaccga   2700
ctcctacagg acaagtggga cagatttgtc aagcgcatct tctacttcaa cttcttcgtc   2760
```

```
tactgcttgt atatgatcat cttcaccgcg gctgcctact atcggcctgt ggaaggcttg      2820
cccccctata agctgcacca ccaccaccac cacaaaaaca ccgttgggga ctatttccga      2880
gtcaccggag agatcttgtc tgtgtcagga ggagtctact tcttcttccg agggattcaa      2940
tatttcctgc agaggcgacc atccctcaag agtttgtttg tggacagcta cagtgagata      3000
cttttctttg tacagtcgct gttcatgctg gtgtctgtgg tactgtactt cagccaacgc      3060
aaggagtatg tggcttccat ggtgttctcc ctggccatgg gctggaccaa catgctctac      3120
tatacccgag gattccagca gatgggcatc tatgctgtca tgattgagaa gatgatcctc      3180
agagacctgt gccggtttat gttcgtctac ctcgtgttct tgtttggatt ttccacagct      3240
gtggtgacac tgattgagga tgggaagaat aactctctgc ctatggagtc cacaccacac      3300
aagtgccggg ggtctgcctg caagccaggt aactcttaca acagcctgta ttccacatgt      3360
ctggagctgt tcaagttcac catcggcatg ggcgacctgg agttcactga gaactacgac      3420
ttcaaggctg tcttcatcat cctgttactg gcctatgtga ttctcaccta catccttctg      3480
ctcaacatgc tcattgctct catgggtgag accgtcaaca agattgcaca agagagcaag      3540
aacatctgga agctgcagag agccatcacc atcctggata cagagaagag cttcctgaag      3600
tgcatgagga aggccttccg ctctggcaag ctgctgcagg tggggttcac tcctgacggc      3660
aaggatgact accggtggtg tttcagggtg gacgaggtaa actggactac ctggaacacc      3720
aatgtgggta tcatcaacga ggacccaggc aactgtgagg gcgtcaagcg caccctgagc      3780
ttctccctga ggtcaggccg agtttcaggg agaaactgga agaactttgc cctggttccc      3840
cttctgaggg atgcaagcac tcgagataga catgccaccc agcaggaaga agttcaactg      3900
aagcattata cgggttccct taagccagag gatgctgagg ttttcaagga ttccatggtc      3960
ccaggggaga aactcgaggg cagaggaagt cttctaacat gcggtgacgt ggaggagaat      4020
cccggccctg caccgggatc caccatggtg agcaagggcg aggaggataa catggccatc      4080
atcaaggagt tcatgcgctt caaggtgcac atggagggct ccgtgaacgg ccacgagttc      4140
gagatcgagg gcgagggcga gggccgcccc tacgagggca cccagaccgc caagctgaag      4200
gtgaccaagg gtggccccct gcccttcgcc tgggacatcc tgtcccctca gttcatgtac      4260
ggctccaagg cctacgtgaa gcaccccgcc gacatccccg actacttgaa gctgtccttc      4320
cccgagggct tcaagtggga gcgcgtgatg aacttcgagg acggcggcgt ggtgaccgtg      4380
acccaggact cctccctgca ggacggcgag ttcatctaca aggtgaagct gcgcggcacc      4440
aacttcccct ccgacggccc cgtaatgcag aagaagacca tgggctggga ggcctcctcc      4500
gagcggatgt accccgagga cggcgccctg aagggcgaga tcaagcagag gctgaagctg      4560
aaggacggcg gccactacga cgctgaggtc aagaccacct acaaggccaa gaagcccgtg      4620
cagctgcccg gcgcctacaa cgtcaacatc aagttggaca tcacctccca caacgaggac      4680
tacaccatcg tggaacagta cgaacgcgcc gagggccgcc actccaccgg cggcatggac      4740
gagctgtaca agtaatgaga attcgatatc aagcttatcg ataatcaacc tctggattac      4800
aaaatttgtg aaagattgac tggtattctt aactatgttg ctccttttac gctatgtgga      4860
tacgctgctt taatgccttt gtatcatgct attgcttccc gtatggcttt cattttctcc      4920
tccttgtata aatcctggtt gctgtctctt tatgaggagt tgtggcccgt tgtcaggcaa      4980
cgtggcgtgg tgtgcactgt gtttgctgac gcaaccccca ctggttgggg cattgccacc      5040
acctgtcagc tcctttccgg gactttcgct ttccccctcc ctattgccac ggcggaactc      5100
atcgccgcct gccttgcccg ctgctggaca ggggctcggc tgttgggcac tgacaattcc      5160
```

```
gtggtgttgt cggggaaatc atcgtccttt ccttggctgc tcgcctatgt tgccacctgg    5220
attctgcgcg ggacgtcctt ctgctacgtc ccttcggccc tcaatccagc ggaccttcct    5280
tcccgcggcc tgctgccggc tctgcggcct cttccgcgtc ttcgccttcg ccctcagacg    5340
agtcggatct ccctttgggc cgcctccccg catcgatacc gagcgctgct cgagagatct    5400
acgggtggca tccctgtgac ccctccccag tgcctctcct ggccctggaa gttgccactc    5460
cagtgcccac cagccttgtc ctaataaaat taagttgcat cattttgtct gactaggtgt    5520
ccttctataa tattatgggg tggagggggg tggtatggag caagggcaa gttgggaaga     5580 caacctgtag ggcctgcggg gtctattggg aaccaagctg gagtgcagtg gcacaatctt    5640
ggctcactgc aatctccgcc tcctgggttc aagcgattct cctgcctcag cctcccgagt    5700
tgttgggatt ccaggcatgc atgaccaggc tcagctaatt tttgtttttt tggtagagac    5760
ggggtttcac catattggcc aggctggtct ccaactccta atctcaggtg atctacccac    5820
cttggcctcc caaattgctg ggattacagg cgtgaaccac tgctcccttc cctgtccttc    5880
tgattttgta ggtaaccacg tgcggaccga gcggccgcag gaacccctag tgatggagtt    5940
ggccactccc tctctgcgcg ctcgctcgct cactgaggcc gggcgaccaa aggtcgcccg    6000
acgcccgggc tttgcccggg cggcctcagt gagcgagcga gcgcgcagct gcctgcagg     6059
```

<210> SEQ ID NO 8
<211> LENGTH: 6056
<212> TYPE: DNA
<213> ORGANISM: Mus musculus

<400> SEQUENCE: 8

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtaagct ttgcaaagat ggataaagtt     180
ttaaacagag aggaatcttt gcagctaatg gaccttctag gtcttgaaag gagtgggaat     240
tggctccggt gcccgtcagt gggcagagcg cacatcgccc acagtccccg agaagttggg     300 gggagggggtc ggcaattgaa ccggtgccta gagaaggtgg cgcggggtaa actgggaaag    360
tgatgtcgtg tactggctcc gccttttttcc cgagggtggg ggagaaccgt atataagtgc    420
agtagtcgcc gtgaacgttc tttttcgcaa cgggtttgcc gccagaacac aggtaagtgc     480
cgtgtgtggt tcccgcgggc ctggcctctt tacgggttat ggcccttgcg tgccttgaat    540
tacttccact ggctgcagta cgtgattctt gatcccgagc ttcgggttgg aagtgggtgg    600
gagagttcga ggccttgcgc ttaaggagcc ccttcgcctc gtgcttgagt tgaggcctgg    660
cctgggcgct ggggccgccg cgtgcgaatc tggtggcacc ttcgcgcctg tctcgctgct    720
ttcgataagt ctctagccat ttaaaatttt tgatgacctg ctgcgacgct ttttttctgg    780
caagatagtc ttgtaaatgc gggccaagat ctgcacactg gtatttcggt ttttggggcc    840
gcgggcggcg acggggcccg tgcgtcccag cgcacatgtt cggcgaggcg gggcctgcga    900
gcgcggccac cgagaatcgg acggggggtag tctcaagctg gccggcctgc tctggtgcct    960
ggcctcgcgc cgccgtgtat cgccccgccc tgggcggcaa ggctggcccg gtcggcacca   1020
gttgcgtgag cggaaagatg gccgcttccc ggccctgctg cagggagctc aaaatggagg   1080
acgcggcgct cgggagagcg ggcgggtgag tcacccacac aaaggaaaag ggcctttccg   1140
tcctcagccg tcgcttcatg tgactccacg gagtaccggg cgccgtccag gcacctcgat   1200
```

-continued

```
tagttctcga gcttttggag tacgtcgtct ttaggttggg gggaggggtt ttatgcgatg    1260
gagtttcccc acactgagtg ggtggagact gaagttaggc cagcttggca cttgatgtaa    1320
ttctccttgg aatttgccct ttttgagttt ggatcttggt tcattctcaa gcctcagaca    1380
gtggttcaaa gtttttttct tccatttcag gtgtcgtgag gtaccggcgg ccgcgccacc    1440
atggaacaac gggctagctt agactcagag gagtctgagt ccccacccca agagaactcc    1500
tgcctggacc ctccagacag agaccctaac tgcaagccac ctccagtcaa gccccacatc    1560
ttcactacca ggagtcgtac ccggcttttt gggaagggtg actcggagga ggcctctccc    1620
ctggactgcc cttatgagga aggcgggctg gcttcctgcc ctatcatcac tgtcagctct    1680
gttctaacta tccagaggcc tggggatgga cctgccagtg tcaggccgtc atcccaggac    1740
tccgtctccg ctggtgagaa gcccccgagg ctctatgatc gcaggagcat cttcgatgct    1800
gtggctcaga gtaactgcca ggagctggag agcctgctgc ccttcctgca gaggagcaag    1860
aagcgcctga ctgacagcga gttcaaagac ccagagacag gaaagacctg tctgctaaaa    1920
gccatgctca atctgcacaa tgggcagaat gacaccatcg ctctgctcct ggacgttgcc    1980
cggaagacag acagcctgaa gcagtttgtc aatgccagct acacagacag ctactacaag    2040
ggccagacag cactgcacat tgccattgaa cggcggaaca tgacgctggt gaccctcttg    2100
gtggagaatg gagcagatgt ccaggctgcg gctaacgggg acttcttcaa gaaaaccaaa    2160
gggaggcctg gcttctactt tggtgagctg cccctgtccc tggctgcgtg caccaaccag    2220
ctggccattg tgaagttcct gctgcagaac tcctggcagc ctgcagacat cagcgcccgg    2280
gactcagtgg gcaacacggt gcttcatgcc ctggtggagg tggcagataa cacagttgac    2340
aacaccaagt tcgtgacaag catgtacaac gagatcttga tcctgggggc caaactccac    2400
cccacgctga agctggaaga gatcaccaac aggaaggggc tcacgccact ggctctggct    2460
gctagcagtg ggaagatcgg ggtcttggcc tacattctcc agagggagat ccatgaaccc    2520
gagtgccgac acctatccag gaagttcacc gaatgggcct atgggccagt gcactcctcc    2580
ctttatgacc tgtcctgcat tgacacctgt gaaaagaact cggttctgga ggtgatcgct    2640
tacagcagca gtgagacccc taaccgtcat gacatgcttc tcgtggaacc cttgaaccga    2700
ctcctacagg acaagtggga cagatttgtc aagcgcatct tctacttcaa cttcttcgtc    2760
tactgcttgt atatgatcat cttcaccgcg gctgcctact atcggcctgt ggaaggcttg    2820
cccccctata agctgaaaaa caccgttggg gactatttcc gagtcaccgg agagatcttg    2880
tctgtgtcag gaggagtcta cttcttcttc cgagggattc aatatttcct gcagaggcga    2940
ccatccctca agagtttgtt tgtggacagc tacagtgaga tactttttctt tgtacagtcg    3000 ctgttcatgc tggtgtctgt ggtactgtac ttcagccaac gcaaggagta gtgtggcttcc    3060 atggtgttct ccctggccat gggctggacc aacatgctct actatacccg aggattccag    3120
cagatgggca tctatgctgt catgattgag aagatgatcc tcagagacct gtgccggttt    3180
atgttcgtct acctcgtgtt cttgtttgga ttttccacag ctgtggtgac actgattgag    3240
gatgggaaga ataactctct gcctatggag tccacaccac acaagtgccg ggggtctgcc    3300
tgcaagccag gtaactctta caacagcctg tattccacat gtctggagct gttcaagttc    3360
accatcggca tgggcgacct ggagttcact gagaactacg acttcaaggc tgtcttcatc    3420
atcctgttac tggcctatgt gattctcacc tacatccttc tgctcaacat gctcattgct    3480
ctcatgggtg agaccgtcaa caagattgca caagagagca agaacatctg gaagctgcag    3540
agagccatca ccatcctgga tacagagaag agcttcctga agtgcatgag gaaggccttc    3600
```

-continued

```
cgctctggca agctgctgca ggtggggttc actcctgacg gcaaggatga ctaccggtgg      3660
tgtttcaggg tggacgaggt aaactggact acctggaaca ccaatgtggg tatcatcaac      3720
gaggacccag gcaactgtga gggcgtcaag cgcaccctga gcttctccct gaggtcaggc      3780
cgagtttcag ggagaaactg gaagaacttt gccctggttc cccttctgag ggatgcaagc      3840
actcgagata gacatgccac ccagcaggaa gaagttcaac tgaagcatta tacgggatcc      3900
cttaagccag aggatgctga ggttttcaag gattccatgg tcccagggga gaaactcgag      3960
ggcagaggaa gtcttctaac atgcggtgac gtggaggaga atcccggccc tgcaccggga      4020
tccaccatgg tgagcaaggg cgaggagctg ttcaccgggg tggtgcccat cctggtcgag      4080
ctggacggcg acgtaaacgg ccacaagttc agcgtgtccg gcgagggcga gggcgatgcc      4140
acctacggca agctgaccct gaagttcatc tgcaccaccg gcaagctgcc cgtgccctgg      4200
cccaccctcg tgaccaccct gacctacggc gtgcagtgct tcagccgcta ccccgaccac      4260
atgaagcagc acgacttctt caagtccgcc atgcccgaag ctacgtcca ggagcgcacc       4320 atcttcttca aggacgacgg caactacaag acccgcgccg aggtgaagtt cgagggcgac      4380
accctggtga accgcatcga gctgaagggc atcgacttca aggaggacgg caacatcctg      4440
gggcacaagc tggagtacaa ctacaacagc cacaacgtct atatcatggc cgacaagcag      4500
aagaacggca tcaaggtgaa cttcaagatc cgccacaaca tcgaggacgg cagcgtgcag      4560
ctcgccgacc actaccagca gaacacccc atcggcgacg ccccgtgct gctgcccgac        4620 aaccactacc tgagcaccca gtccgccctg agcaaagacc ccaacgagaa gcgcgatcac      4680
atggtcctgc tggagttcgt gaccgccgcc gggatcactc tcggcatgga cgagctgtac      4740
aagtgataaa agcttgaatt cgatatcaag cttatcgata tcaacctct ggattacaaa       4800 atttgtgaaa gattgactgg tattcttaac tatgttgctc cttttacgct atgtggatac      4860
gctgctttaa tgcctttgta tcatgctatt gcttcccgta tggctttcat tttctcctcc      4920
ttgtataaat cctggttgct gtctctttat gaggagttgt ggcccgttgt caggcaacgt      4980
ggcgtggtgt gcactgtgtt tgctgacgca accccactg gttggggcat tgccaccacc       5040
tgtcagctcc tttccgggac tttcgctttc cccctcccta ttgccacggc ggaactcatc      5100
gccgcctgcc ttgcccgctg ctggacaggg gctcggctgt tgggcactga caattccgtg      5160
gtgttgtcgg ggaaatcatc gtcctttcct tggctgctcg cctatgttgc cacctggatt      5220
ctgcgcggga cgtccttctg ctacgtccct tcggccctca atccagcgga ccttccttcc      5280
cgcggcctgc tgccggctct gcggcctctt ccgcgtcttc gccttcgccc tcagacgagt      5340
cggatctccc tttgggccgc ctccccgcat cgataccgag cgctgctcga gagatctacg      5400
ggtggcatcc ctgtgacccc tccccagtgc ctctcctggc cctggaagtt gccactccag      5460
tgcccaccag ccttgtccta ataaaattaa gttgcatcat tttgtctgac taggtgtcct      5520
tctataatat tatggggtgg aggggggtgg tatggagcaa gggggaagtt gggaagacaa      5580
cctgtagggc ctgcggggtc tattgggaac caagctggag tgcagtggca caatcttggc      5640
tcactgcaat ctccgcctcc tgggttcaag cgattctcct gcctcagcct cccgagttgt      5700
tgggattcca ggcatgcatg accaggctca gctaattttt gtttttttgg tagagacggg      5760
gtttcaccat attggccagg ctggtctcca actcctaatc tcaggtgatc tacccacctt      5820
ggcctcccaa attgctggga ttacaggcgt gaaccactgc tcccttccct gtccttctga      5880
ttttgtaggt aaccacgtgc ggaccgagcg gccgcaggaa cccctagtga tggagttggc      5940
```

-continued

```
cactccctct ctgcgcgctc gctcgctcac tgaggccggg cgaccaaagg tcgcccgacg    6000
cccgggcttt gcccgggcgg cctcagtgag cgagcgagcg cgcagctgcc tgcagg       6056

<210> SEQ ID NO 9
<211> LENGTH: 6869
<212> TYPE: DNA
<213> ORGANISM: Mus musculus

<400> SEQUENCE: 9
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtaagct ttgcaaagat ggataaagtt     180
ttaaacagag aggaatcttt gcagctaatg gaccttctag gtcttgaaag gagtgggaat     240
tggctccggt gcccgtcagt gggcagagcg cacatcgccc acagtccccg agaagttggg     300
gggaggggtc ggcaattgaa ccggtgccta gagaaggtgg cgcggggtaa actgggaaag     360
tgatgtcgtg tactggctcc gccttttttcc cgagggtggg ggagaaccgt atataagtgc     420
agtagtcgcc gtgaacgttc tttttcgcaa cgggtttgcc gccagaacac aggtaagtgc     480
cgtgtgtggt tcccgcgggc ctggcctctt tacgggttat ggcccttgcg tgccttgaat     540
tacttccact ggctgcagta cgtgattctt gatcccgagc ttcgggttgg aagtgggtgg     600
gagagttcga ggccttgcgc ttaaggagcc ccttcgcctc gtgcttgagt tgaggcctgg     660
cctgggcgct ggggccgccg cgtgcgaatc tggtggcacc ttcgcgcctg tctcgctgct     720
ttcgataagt ctctagccat ttaaaatttt tgatgacctg ctgcgacgct ttttttctgg     780
caagatagtc ttgtaaatgc gggccaagat ctgcacactg gtatttcggt ttttggggcc     840
gcgggcggcg acgggcccg tgcgtcccag cgcacatgtt cggcgaggcg gggcctgcga     900
gcgcggccac cgagaatcgg acgggggtag tctcaagctg gccggcctgc tctggtgcct     960
ggcctcgcgc cgccgtgtat cgccccgccc tgggcggcaa ggctggcccg gtcggcacca    1020
gttgcgtgag cggaaagatg gccgcttccc ggccctgctg cagggagctc aaaatggagg    1080
acgcggcgct cgggagagcg ggcgggtgag tcacccacac aaaggaaaag ggcctttccg    1140
tcctcagccg tcgcttcatg tgactccacg gagtaccggg cgccgtccag gcacctcgat    1200
tagttctcga gcttttggag tacgtcgtct ttaggttggg gggaggggtt ttatgcgatg    1260
gagtttcccc acactgagtg ggtggagact gaagttaggc cagcttggca cttgatgtaa    1320
ttctccttgg aatttgccct tttttgagttt ggatcttggt tcattctcaa gcctcagaca    1380
gtggttcaaa gtttttttct tccatttcag gtgtcgtgag gtaccggatc cgctagcgcc    1440
accatgaaga ggagcatcct gaagtggttc cagagcaggg accagaagca gcaccccagc    1500
agctacgagg gcgtggtgtg cgaggccgac gcctgcagcg tggccagcca ggacgtgttc    1560
aaggtgatca gcgacggcag cacctgcagg ctgaggagct tcatcaagaa gaacaggggag    1620 ggcctgaaga agctggacaa gctgaacgcc acccccctgc accacgccgc cggcaagggc    1680
cagctggagc tgatgcagat gatcatggac gacagcagct cgaggccct gaacgtgacc    1740 gacagcagcg gcaacacccc cctgcactgg gccaccaaga gcagcagac cgagagcgtg    1800 aagctgctgc tgagcagggg cgccaacccc aacatcctga acagcaacat ggtgagcccc    1860
ctgcactggg ccgtgcagta cctgtgcaac gacctggtga agatcttcct ggagtgcagc    1920
atcaccgacg tgaacctgga gggcgagggc ggcaacaccc ccatcctggt ggcctgctac    1980
aaggacaaca gcgaggccct gaagctgctg atcgagaacg gcggcgacat cgccaaggcc    2040
```

-continued

```
aacaacatgg gctgcatgcc cgtgcacgcc gccgccttca gcggcagcaa gctgtgcctg   2100
gagatcatca tcaagagggg cgtggagctg ggctacagcc ccgagaacca catcaacttc   2160
accaacaacg gcaagtgcag ccccctgcac ctggccgtgc agagcaggga cctggagatg   2220
atcaagatgt gcatcgagta cggcgcccag atcgacctga agcagaacga caactgcacc   2280
gccctgcact tcgccgccac ccagggcgcc accgagatcc tgaagctgat gatgagcagc   2340
tacaccggcg aggagagcat catcaacgcc ctggacggca acaaggagac cctgctgcac   2400
agggccgccc tgttcgacca ccacgagctg gccgagtacc tgatcagcaa gggcgccaac   2460
atcaacagcg tggacatcga gggcaggacc cccctgctgc tggccaccag ctgcgccagc   2520
tggaagatcg tgaacctgct gctgagcaag ggcgccaacg tggagctgaa ggacctgctg   2580
ggccacaact tcctgcacct gaccgtgctg cagcccggcg gcctgcagca cctgaacgag   2640
gacttcctga agatgaagca catcagggac ctgatcaccg aggaggacca ggagggctgc   2700 accccctgc actacgccag caagcagggc gtgcccctga gcgtgaacat cctgctggag   2760
atgaacgtga gcgtgtacgc caagagcagg gacaagaaga gcccctgca cttcgccgcc   2820 agctacggca ggatcaacac ctgcctgagg ctgctggagg ccatggagga caccaggctg   2880
ctgaacgagg gcgacaagaa gggcatgacc cccctgcacc tggccgccca aacggccac   2940 gagaaggtg tgcagttcct gctgaagaag ggcgccctgt tcctgtgcga ctacaagggc   3000
tggaccgccc tgcaccacgc cgccttcggc ggctacacca ggaccatgca gatcatcctg   3060
aacaccaaca tgaaggccac cgacaaggtg aacgacgagg gcaacaccgc cctgcacctg   3120
gccgccaggg agggccacgc caaggccgtg aagctgctgc tggacgacaa cgccaagatc   3180
ctgctgaaca gcgccgaggc cagcttcctg cacgaggcca tccacaacgg caggaaggac   3240
gtggtgaacg ccgtgatcct gcacaagagg tgggaggaga gcatcaccac cttcagccac   3300
cacagcagca tcaacaagtg cgccatcctg gagatggtgg agtacctgcc cgagtgcctg   3360
aagctggtgc tggacaactg catcatcgag agccccgacg agaagggcag caaggacttc   3420
tgcatcgagt acaacttcag gtacctgcag tgccccctga gctgaagaa gaagttcaag   3480 gagaacgagg gcatcatcta cgagcccctg ctggccctga cggcatggt gaggcacaac   3540 agggtggagc tgctgagcca ccccgtgtgc accgagtacc tgctgatgaa gtggatggcc   3600
tacggcttca gggcccacat cctgaacctg gccgtgtaca gcctgggcct gatccccctg   3660 acCtgctgg tgacccacct ggagcccgac gtgtgcttca cgccaccct gaagtacggc   3720 ccttcgaca acaaggacag caacttcatc aaggtgtgca tgagcctggt gttcatcatg   3780
agcctgttcg gcatctgcaa ggagatcatc cagctgttcc agcagaagct gaactacctg   3840
ctggactaca gcaacctgct ggactggacc atctacacca ccagcatcat cttcgtgagc   3900
agcctgttcg tgatgctgcc catcaggctg cagtgggact gcggcgccat cgccatcctg   3960
ctggcctgga ccaacttcct gctgtacctg cagaggttcg agaactacgg catctacatc   4020
gtgatgttct gggagatcct gaggaccctg atcaggatcg tgatcgtgtt cttcttcctg   4080
atgctggcct tcggcctgag cttctacgtg ctgctgggca gccagcagac ctacggcacc   4140
ccctacctga gcgtgatgca gaccttcagc atgatgatcg cgacaacaa ctacaggag   4200 gccttcctgg agcccatgct ggccgacaag ctgcccttcc ccttcctgag cttcatcatc   4260
ctgatcatct tcagcatgct gatccccatc ctgctgatga acctgctgat cggcctggcc   4320
gtgggcgaca tcgccgaggt gcagaagttc gccgccatga agaggatcgc catgcaggtg   4380
```

-continued

```
aacctgcaca ccaacctgga gaagaagctg ccctactggt tcctgagcag ggtggaccag   4440
gagagcatcg tggtgtaccc caacaagccc aggtactgcg gcttcatgac cgtgttccag   4500
tactgcttcg gctgggacaa caccgccgcc gacacccaga gcgccgacac caccctggag   4560
ctggaggtgc tgaagcagaa gtacaggctg aaggacatcg ccgccctggt ggagaagcag   4620
cacaacctgc tgaagctggt ggcccagaag atggagatca tgagcgaggc cgaggacgag   4680
gaccccaacg acctgttcca gaacaagttc aggaaggagc agctggagca caagaacagc   4740
aagtgggaca ccgtgctgaa ggccgtgaag agcaagtgcg ccgtcgaggg cagaggaagt   4800
cttctaacat gcggtgacgt ggaggagaat cccggccctg caccgggatc caccatggtg   4860
agcaagggcg aggaggataa catggccatc atcaaggagt tcatgcgctt caaggtgcac   4920
atggagggct ccgtgaacgg ccacgagttc gagatcgagg gcgagggcga gggccgcccc   4980
tacgagggca cccagaccgc caagctgaag gtgaccaagg gtggcccccct gcccttcgcc   5040 tgggacatcc tgtcccctca gttcatgtac ggctccaagg cctacgtgaa gcaccccgcc   5100
gacatccccg actacttgaa gctgtccttc cccgagggct tcaagtggga gcgcgtgatg   5160
aacttcgagg acggcggcgt ggtgaccgtg acccaggact cctccctgca ggacggcgag   5220
ttcatctaca aggtgaagct gcgcggcacc aacttccccct ccgacggccc cgtaatgcag   5280
aagaagacca tgggctggga ggcctcctcc gagcggatgt accccgagga cggcgccctg   5340
aagggcgaga tcaagcagag gctgaagctg aaggacggcg gccactacga cgctgaggtc   5400
aagaccacct acaaggccaa gaagcccgtg cagctgcccg gcgcctacaa cgtcaacatc   5460
aagttggaca tcacctccca caacgaggac tacaccatcg tggaacagta cgaacgcgcc   5520
gagggccgcc actccaccgg cggcatggac gagctgtaca gtaatgagaa ttcgatatc   5580 aagcttatcg ataatcaacc tctggattac aaaatttgtg aaagattgac tggtattctt   5640
aactatgttg ctccttttac gctatgtgga tacgctgctt taatgccttt gtatcatgct   5700
attgcttccc gtatggcttt catttttctc ccttgtata aatcctggtt gctgtctctt   5760
tatgaggagt tgtggcccgt tgtcaggcaa cgtggcgtgg tgtgcactgt gtttgctgac   5820 gcaacccccca ctggttgggg cattgccacc acctgtcagc tcctttccgg gactttcgct   5880
ttccccctcc ctattgccac ggcggaactc atcgccgcct gccttgcccg ctgctggaca   5940
ggggctcggc tgttgggcac tgacaattcc gtggtgttgt cggggaaatc atcgcctttt   6000
ccttggctgc tcgcctatgt tgccacctgg attctgcgcg ggacgtcctt ctgctacgtc   6060
ccttcggccc tcaatccagc ggaccttcct tcccgcggcc tgctgccggc tctgcggcct   6120
cttccgcgtc ttcgccttcg ccctcagacg agtcggatct ccctttgggc cgcctccccg   6180
catcgatacc gagcgctgct cgagagatct acgggtggca tccctgtgac ccctccccag   6240
tgcctctcct ggccctggaa gttgccactc cagtgcccac cagccttgtc ctaataaaat   6300
taagttgcat cattttgtct gactaggtgt ccttctataa tattatgggg tggaggggggg   6360 tggtatggag caagggcaa gttgggaaga caacctgtag ggcctgcggg gtctattggg   6420
aaccaagctg gagtgcagtg gcacaatctt ggctcactgc aatctccgcc tcctgggttc   6480
aagcgattct cctgcctcag cctcccgagt tgttgggatt ccaggcatgc atgaccaggc   6540
tcagctaatt tttgtttttt tggtagagac ggggtttcac catattggcc aggctggtct   6600
ccaactccta atctcaggtg atctacccac cttggcctcc caaattgctg ggattacagg   6660
cgtgaaccac tgctcccttc cctgtccttc tgattttgta ggtaaccacg tgcggaccga   6720
gcggccgcag gaacccctag tgatggagtt ggccactccc tctctgcgcg ctcgctcgct   6780
```

-continued

```
cactgaggcc gggcgaccaa aggtcgcccg acgcccgggc tttgcccggg cggcctcagt    6840
gagcgagcga gcgcgcagct gcctgcagg                                      6869

<210> SEQ ID NO 10
<211> LENGTH: 6929
<212> TYPE: DNA
<213> ORGANISM: Mus musculus

<400> SEQUENCE: 10
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac tagggggttcc tgcggccgca cgcgtaagct ttgcaaagat ggataaagtt    180
ttaaacagag aggaatcttt gcagctaatg gaccttctag gtcttgaaag gagtgggaat    240
tggctccggt gcccgtcagt gggcagagcg cacatcgccc acagtccccg agaagttggg    300
gggaggggtc ggcaattgaa ccggtgccta gagaaggtgg cgcggggtaa actgggaaag    360
tgatgtcgtg tactggctcc gcctttttcc cgagggtggg ggagaaccgt atataagtgc    420
agtagtcgcc gtgaacgttc tttttcgcaa cgggtttgcc gccagaacac aggtaagtgc    480
cgtgtgtggt tcccgcgggc ctggcctctt tacgggttat ggcccttgcg tgccttgaat    540
tacttccact ggctgcagta cgtgattctt gatcccgagc ttcgggttgg aagtgggtgg    600
gagagttcga ggccttgcgc ttaaggagcc ccttcgcctc gtgcttgagt tgaggcctgg    660
cctgggcgct ggggccgccg cgtgcgaatc tggtggcacc ttcgcgcctg tctcgctgct    720
ttcgataagt ctctagccat ttaaaatttt tgatgacctg ctgcgacgct ttttttctgg    780
caagatagtc ttgtaaatgc gggccaagat ctgcacactg gtatttcggt ttttggggcc    840
gcgggcggcg acggggcccg tgcgtcccag cgcacatgtt cggcgaggcg gggcctgcga    900
gcgcggccac cgagaatcgg acgggggtag tctcaagctg gccggcctgc tctggtgcct    960
ggcctcgcgc cgccgtgtat cgccccgccc tgggcggcaa ggctggcccg gtcggcacca   1020
gttgcgtgag cggaaagatg gccgcttccc ggccctgctg cagggagctc aaaatggagg   1080
acgcggcgct cgggagagcg ggcgggtgag tcacccacac aaaggaaaag ggcctttccg   1140
tcctcagccg tcgcttcatg tgactccacg gagtaccggg cgccgtccag gcacctcgat   1200
tagttctcga gcttttggag tacgtcgtct ttaggttggg gggaggggtt ttatgcgatg   1260
gagtttcccc acactgagtg ggtggagact gaagttaggc cagcttggca cttgatgtaa   1320
ttctccttgg aatttgccct ttttgagttt ggatcttggt tcattctcaa gcctcagaca   1380
gtggttcaaa gtttttttct tccatttcag gtgtcgtgag gtaccggatc cgctagcgcc   1440
accatgaaga ggagcatcct gaagtggttc cagagcaggg accagaagca gcaccccagc   1500
agctacgagg gcgtggtgtg cgaggccgac gcctgcagcg tggccagcca ggacgtgttc   1560
aaggtgatca gcgacggcag cacctgcagg ctgaggagct tcatcaagaa gaacagggag   1620
ggcctgaaga agctggacaa gctgaacgcc acccccctgc accacgccgc cggcaagggc   1680
cagctggagc tgatgcagat gatcatggac gacagcagct cgaggccct gaacgtgacc   1740 gacagcagcg gcaacacccc cctgcactgg gccaccaaga gcagcagac cgagagcgtg   1800 aagctgctgc tgagcagggg cgccaacccc aacatcctga cagcaacat ggtgagcccc   1860 ctgcactggg ccgtgcagta cctgtgcaac gacctggtga agatcttcct ggagtgcagc   1920
atcaccgacg tgaacctgga gggcgagggc ggcaacaccc ccatcctggt ggcctgctac   1980
```

-continued

```
aaggacaaca gcgaggccct gaagctgctg atcgagaacg gcggcgacat cgccaaggcc    2040
aacaacatgg gctgcatgcc cgtgcacgcc gccgccttca gcggcagcaa gctgtgcctg    2100
gagatcatca tcaagagggg cgtggagctg ggctacagcc ccgagaacca catcaacttc    2160
accaacaacg gcaagtgcag ccccctgcac ctggccgtgc agagcaggga cctggagatg    2220
atcaagatgt gcatcgagta cggcgcccag atcgacctga agcagaacga caactgcacc    2280
gccctgcact cgccgccac ccagggcgcc accgagatcc tgaagctgat gatgagcagc    2340
tacaccggcg aggagagcat catcaacgcc ctggacggca acaaggagac cctgctgcac    2400
agggccgccc tgttcgacca ccacgagctg gccgagtacc tgatcagcaa gggcgccaac    2460
atcaacagcg tggacatcga gggcaggacc cccctgctgc tggccaccag ctgcgccagc    2520
tggaagatcg tgaacctgct gctgagcaag ggcgccaacg tggagctgaa ggacctgctg    2580
ggccacaact tcctgcacct gaccgtgctg cagcccggcg gcctgcagca cctgaacgag    2640
gacttcctga agatgaagca catcagggac ctgatcaccg aggaggacca ggagggctgc    2700 accccccctgc actacgccag caagcagggc gtgcccctga gcgtgaacat cctgctggag    2760
atgaacgtga gcgtgtacgc caagagcagg gacaagaaga gccccctgca cttcgccgcc    2820
agctacggca ggatcaacac ctgcctgagg ctgctggagg ccatggagga caccaggctg    2880
ctgaacgagg gcgacaagaa gggcatgacc ccctgcacc tggccgccca gaacggccac    2940
gagaaggtgg tgcagttcct gctgaagaag ggcgccctgt tcctgtgcga ctacaagggc    3000
tggaccgccc tgcaccacgc cgccttcggc ggctacacca ggaccatgca gatcatcctg    3060
aacaccaaca tgaaggccac cgacaaggtg aacgacgagg gcaacaccgc cctgcacctg    3120
gccgccaggg agggccacgc caaggccgtg aagctgctgc tggacgacaa cgccaagatc    3180
ctgctgaaca gcgccgaggc cagcttcctg cacgaggcca tccacaacgg caggaaggac    3240
gtggtgaacg ccgtgatcct gcacaagagg tgggaggaga gcatcaccac cttcagccac    3300
cacagcagca tcaacaagtg cgccatcctg gagatggtgg agtacctgcc cgagtgcctg    3360
aagctggtgc tggacaactg catcatcgag agccccgacg agaagggcag caaggacttc    3420
tgcatcgagt acaacttcag gtacctgcag tgcccCCtga agctgaagaa gaagttcaag    3480
gagaacgagg gcatcatcta cgagcccctg ctggccctga acggcatggt gaggcacaac    3540
agggtggagc tgctgagcca ccccgtgtgc accgagtacc tgctgatgaa gtggatggcc    3600
tacggcttca gggcccacat cctgaacctg gccgtgtaca gcctgggcct gatcccctg    3660 accctgctgg tgacccacct ggagcccgac gtgtgcttca acgccaccgg cagcggcagc    3720
ggcttcgcca acgagctggg ccccaggctg atgggcaagg gcagcggcct gaagtacggc    3780
cccttcgaca acaaggacag caacttcatc aaggtgtgca tgagcctggt gttcatcatg    3840
agcctgttcg gcatctgcaa ggagatcatc cagctgttcc agcagaagct gaactacctg    3900
ctggactaca gcaacctgct ggactggacc atctacacca ccagcatcat cttcgtgagc    3960
agcctgttcg tgatgctgcc catcaggctg cagtgggact gcggcgccat cgccatcctg    4020
ctggcctgga ccaacttcct gctgtacctg cagaggttcg agaactacgg catctacatc    4080
gtgatgttct gggagatcct gaggaccctg atcaggatcg tgatcgtgtt cttcttcctg    4140
atgctggcct tcggcctgag cttctacgtg ctgctgggca gccagcagac ctacggcacc    4200
ccctacctga gcgtgatgca gaccttcagc atgatgatcg gcgacaacaa ctacaggggag    4260 gccttcctgg agcccatgct ggccgacaag ctgcccttcc ccttcctgag cttcatcatc    4320
ctgatcatct tcagcatgct gatccccatc ctgctgatga acctgctgat cggcctggcc    4380
```

```
gtgggcgaca tcgccgaggt gcagaagttc gccgccatga agaggatcgc catgcaggtg    4440
aacctgcaca ccaacctgga gaagaagctg ccctactggt tcctgagcag ggtggaccag    4500
gagagcatcg tggtgtaccc caacaagccc aggtactgcg gcttcatgac cgtgttccag    4560
tactgcttcg gctgggacaa caccgccgcc gacacccaga gcgccgacac caccctggag    4620
ctggaggtgc tgaagcagaa gtacaggctg aaggacatcg ccgccctggt ggagaagcag    4680
cacaacctgc tgaagctggt ggcccagaag atggagatca tgagcgaggc cgaggacgag    4740
gaccccaacg acctgttcca gaacaagttc aggaaggagc agctggagca caagaacagc    4800
aagtgggaca ccgtgctgaa ggccgtgaag agcaagtgcg ccgtcgaggg cagaggaagt    4860
cttctaacat gcggtgacgt ggaggagaat cccggccctg caccgggatc caccatggtg    4920
agcaagggcg aggaggataa catggccatc atcaaggagt tcatgcgctt caaggtgcac    4980
atggagggct ccgtgaacgg ccacgagttc gagatcgagg gcgagggcga gggccgcccc    5040
tacgagggca cccagaccgc caagctgaag gtgaccaagg gtggcccct gcccttcgcc    5100 tgggacatcc tgtcccctca gttcatgtac ggctccaagg cctacgtgaa gcaccccgcc    5160 gacatcccg actacttgaa gctgtccttc cccgagggct tcaagtggga gcgcgtgatg    5220
aacttcgagg acggcggcgt ggtgaccgtg acccaggact cctccctgca ggacggcgag    5280
ttcatctaca aggtgaagct gcgcggcacc aacttcccct ccgacggccc cgtaatgcag    5340
aagaagacca tgggctggga ggcctcctcc gagcggatgt accccgagga cggcgccctg    5400
aagggcgaga tcaagcagag gctgaagctg aaggacggcg gccactacga cgctgaggtc    5460
aagaccacct acaaggccaa gaagcccgtg cagctgcccg gcgcctacaa cgtcaacatc    5520
aagttggaca tcacctccca caacgaggac tacaccatcg tggaacagta cgaacgcgcc    5580
gagggccgcc actccaccgg cggcatggac gagctgtaca gtaatgaga attcgatatc    5640 aagcttatcg ataatcaacc tctggattac aaaatttgtg aaagattgac tggtattctt    5700
aactatgttg ctccttttac gctatgtgga tacgctgctt taatgccttt gtatcatgct    5760
attgcttccc gtatggcttt catttttctc tccttgtata aatcctggtt gctgtctctt    5820
tatgaggagt tgtggcccgt tgtcaggcaa cgtggcgtgg tgtgcactgt gtttgctgac    5880
gcaaccccca ctggttgggg cattgccacc acctgtcagc tcctttccgg gactttcgct    5940
ttccccctcc ctattgccac ggcggaactc atcgccgcct gccttgcccg ctgctggaca    6000
ggggctcggc tgttgggcac tgacaattcc gtggtgttgt cggggaaatc atcgtccttt    6060
ccttggctgc tcgcctatgt tgccacctgg attctgcgcg ggacgtcctt ctgctacgtc    6120
ccttcggccc tcaatccagc ggaccttcct tcccgcggcc tgctgccggc tctgcggcct    6180
cttccgcgtc ttcgccttcg ccctcagacg agtcggatct cctttgggc cgcctccccg    6240 catcgatacc gagcgctgct cgagagatct acgggtggca tccctgtgac ccctccccag    6300
tgcctctcct ggccctggaa gttgccactc cagtgcccac cagccttgtc ctaataaaat    6360
taagttgcat cattttgtct gactaggtgt ccttctataa tattatgggg tggaggggggg   6420 tggtatggag caaggggcaa gttgggaaga caacctgtag ggcctgcggg gtctattggg    6480
aaccaagctg gagtgcagtg gcacaatctt ggctcactgc aatctccgcc tcctgggttc    6540
aagcgattct cctgcctcag cctcccgagt tgttgggatt ccaggcatgc atgaccaggc    6600
tcagctaatt tttgtttttt tggtagagac ggggtttcac catattggcc aggctggtct    6660
ccaactccta atctcaggtg atctacccac cttggcctcc caaattgctg ggattacagg    6720
```

-continued

```
cgtgaaccac tgctcccttc cctgtccttc tgattttgta ggtaaccacg tgcggaccga      6780
gcggccgcag gaacccctag tgatggagtt ggccactccc tctctgcgcg ctcgctcgct      6840
cactgaggcc gggcgaccaa aggtcgcccg acgcccgggc tttgcccggg cggcctcagt      6900
gagcgagcga gcgcgcagct gcctgcagg                                        6929

<210> SEQ ID NO 11
<211> LENGTH: 6929
<212> TYPE: DNA
<213> ORGANISM: Mus musculus

<400> SEQUENCE: 11
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc tgcggccgca cgcgtaagct ttgcaaagat ggataaagtt       180
ttaaacagag aggaatcttt gcagctaatg gaccttctag gtcttgaaag gagtgggaat       240
tggctccggt gcccgtcagt gggcagagcg cacatcgccc acagtccccg agaagttggg       300
gggaggggtc ggcaattgaa ccggtgccta gagaaggtgg cgcggggtaa actgggaaag       360
tgatgtcgtg tactggctcc gccttttttcc cgagggtggg ggagaaccgt atataagtgc       420
agtagtcgcc gtgaacgttc tttttcgcaa cgggtttgcc gccagaacac aggtaagtgc       480
cgtgtgtggt tcccgcgggc ctggcctctt tacgggttat ggcccttgcg tgccttgaat       540
tacttccact ggctgcagta cgtgattctt gatcccgagc ttcgggttgg aagtgggtgg       600
gagagttcga ggccttgcgc ttaaggagcc ccttcgcctc gtgcttgagt tgaggcctgg       660
cctgggcgct ggggccgccg cgtgcgaatc tggtggcacc ttcgcgcctg tctcgctgct       720
ttcgataagt ctctagccat ttaaaatttt tgatgacctg ctgcgacgct tttttttctgg       780 caagatagtc ttgtaaatgc gggccaagat ctgcacactg gtatttcggt ttttggggcc       840
gcgggcggcg acggggcccg tgcgtcccag cgcacatgtt cggcgaggcg gggcctgcga       900
gcgcggccac cgagaatcgg acgggggtag tctcaagctg gccggcctgc tctggtgcct       960
ggcctcgcgc cgccgtgtat cgccccgccc tgggcggcaa ggctggcccg gtcggcacca      1020
gttgcgtgag cggaaagatg gccgcttccc ggccctgctg cagggagctc aaaatggagg      1080
acgcggcgct cgggagagcg ggcgggtgag tcacccacac aaaggaaaag ggcctttccg      1140
tcctcagccg tcgcttcatg tgactccacg gagtaccggg cgccgtccag gcacctcgat      1200
tagttctcga gcttttggag tacgtcgtct ttaggttggg gggaggggtt ttatgcgatg      1260
gagtttcccc acactgagtg ggtggagact gaagttaggc cagcttggca cttgatgtaa      1320
ttctccttgg aatttgccct ttttgagttt ggatcttggt tcattctcaa gcctcagaca      1380
gtggttcaaa gttttttttct tccatttcag gtgtcgtgag gtaccggatc cgctagcgcc      1440
accatgaaga ggagcatcct gaagtggttc cagagcaggg accagaagca gcaccccagc      1500
agctacgagg gcgtggtgtg cgaggccgac gcctgcagcg tggccagcca ggacgtgttc      1560
aaggtgatca gcgacggcag cacctgcagg ctgaggagct tcatcaagaa gaacagggag      1620
ggcctgaaga agctggacaa gctgaacgcc accccctgc accacgccgc cggcaagggc      1680
cagctggagc tgatgcagat gatcatggac gacagcagct cgaggccct gaacgtgacc      1740 gacagcagcg gcaacacccc cctgcactgg gccaccaaga gcagcagac cgagagcgtg      1800 aagctgctgc tgagcagggg cgccaacccc aacatcctga acagcaacat ggtgagcccc      1860
ctgcactggg ccgtgcagta cctgtgcaac gacctggtga agatcttcct ggagtgcagc      1920
```

-continued

```
atcaccgacg tgaacctgga gggcgagggc ggcaacaccc ccatcctggt ggcctgctac   1980
aaggacaaca gcgaggccct gaagctgctg atcgagaacg gcggcgacat cgccaaggcc   2040
aacaacatgg gctgcatgcc cgtgcacgcc gccgccttca gcggcagcaa gctgtgcctg   2100
gagatcatca tcaagagggg cgtggagctg ggctacagcc ccgagaacca catcaacttc   2160
accaacaacg gcaagtgcag ccccctgcac ctggccgtgc agagcaggga cctggagatg   2220
atcaagatgt gcatcgagta cggcgcccag atcgacctga agcagaacga caactgcacc   2280
gccctgcact tcgccgccac ccagggcgcc accgagatcc tgaagctgat gatgagcagc   2340
tacaccggcg aggagagcat catcaacgcc ctggacggca acaaggagac cctgctgcac   2400
agggccgccc tgttcgacca ccacgagctg gccgagtacc tgatcagcaa gggcgccaac   2460
atcaacagcg tggacatcga gggcaggacc ccctgctgc tggccaccag ctgcgccagc    2520
tggaagatcg tgaacctgct gctgagcaag ggcgccaacg tggagctgaa ggacctgctg   2580
ggccacaact tcctgcacct gaccgtgctg cagcccggcg gcctgcagca cctgaacgag   2640
gacttcctga agatgaagca catcagggac ctgatcaccg aggaggacca ggagggctgc   2700 accccccctgc actacgccag caagcagggc gtgcccctga gcgtgaacat cctgctggag   2760
atgaacgtga gcgtgtacgc caagagcagg gacaagaaga gccccctgca cttcgccgcc   2820
agctacggca ggatcaacac ctgcctgagg ctgctggagg ccatggagga caccaggctg   2880
ctgaacgagg gcgacaagaa gggcatgacc cccctgcacc tggccgccca gaacggccac   2940
gagaaggtgg tgcagttcct gctgaagaag ggcgccctgt tcctgtgcga ctacaagggc   3000
tggaccgccc tgcaccacgc cgccttcggc ggctacacca ggaccatgca gatcatcctg   3060
aacaccaaca tgaaggccac cgacaaggtg aacgacgagg gcaacaccgc cctgcacctg   3120
gccgccaggg agggccacgc caaggccgtg aagctgctgc tggacgacaa cgccaagatc   3180
ctgctgaaca gcgccgaggc cagcttcctg cacgaggcca tccacaacgg caggaaggac   3240
gtggtgaacg ccgtgatcct gcacaagagg tgggaggaga gcatcaccac cttcagccac   3300
cacagcagca tcaacaagtg cgccatcctg gagatggtgg agtacctgcc cgagtgcctg   3360
aagctggtgc tggacaactg catcatcgag agccccgacg agaagggcag caaggacttc   3420
tgcatcgagt acaacttcag gtacctgcag tgcccctga agctgaagaa gaagttcaag    3480
gagaacgagg gcatcatcta cgagcccctg ctggccctga cggcatggt gaggcacaac    3540 agggtggagc tgctgagcca ccccgtgtgc accgagtacc tgctgatgaa gtggatggcc   3600
tacggcttca gggcccacat cctgaacctg gccgtgtaca gcctgggcct gatcccctg    3660 accctgctgg tgacccacct ggagcccgac gtgtgcttca acgccaccct gaagtacggc   3720
cccttcgaca acaaggacag caacttcatc aaggtgtgca tgagcctggt gttcatcatg   3780
agcctgttcg gcatctgcaa ggagatcatc cagctgttcc agcagaagct gaactacctg   3840
ctggactaca gcaacctgct ggactggacc atctacacca ccagcatcat cttcgtgagc   3900
agcctgttcg tgatgggcag cggcagcggc ttcgccaacg agctgggccc caggctgatg   3960
ggcaagggca gcggcctgcc catcaggctg cagtgggact gcggcgccat cgccatcctg   4020
ctggcctgga ccaacttcct gctgtacctg cagaggttca gaaactacgg catctacatc   4080
gtgatgttct gggagatcct gaggaccctg atcaggatcg tgatcgtgtt cttcttcctg   4140
atgtggccct cggcctgag cttctacgtg ctgctgggca ccagcagac ctacggcacc     4200 ccctacctga gcgtgatgca gaccttcagc atgatgatcg gcgacaacaa ctacagggag   4260
```

-continued

```
gccttcctgg agcccatgct ggccgacaag ctgcccttcc ccttcctgag cttcatcatc      4320
ctgatcatct tcagcatgct gatccccatc ctgctgatga acctgctgat cggcctggcc      4380
gtgggcgaca tcgccgaggt gcagaagttc gccgccatga agaggatcgc catgcaggtg      4440
aacctgcaca ccaacctgga gaagaagctg ccctactggt tcctgagcag ggtggaccag      4500
gagagcatcg tggtgtaccc caacaagccc aggtactgcg gcttcatgac cgtgttccag      4560
tactgcttcg gctgggacaa caccgccgcc gacacccaga gcgccgacac caccctggag      4620
ctggaggtgc tgaagcagaa gtacaggctg aaggacatcg ccgccctggt ggagaagcag      4680
cacaacctgc tgaagctggt ggcccagaag atggagatca tgagcgaggc cgaggacgag      4740
gaccccaacg acctgttcca gaacaagttc aggaaggagc agctggagca caagaacagc      4800
aagtgggaca ccgtgctgaa ggccgtgaag agcaagtgcg ccgtcgaggg cagaggaagt      4860
cttctaacat gcggtgacgt ggaggagaat cccggccctg caccgggatc caccatggtg      4920
agcaagggcg aggaggataa catggccatc atcaaggagt tcatgcgctt caaggtgcac      4980
atggagggct ccgtgaacgg ccacgagttc gagatcgagg gcgagggcga gggccgcccc      5040
tacgagggca cccagaccgc caagctgaag gtgaccaagg gtggccccct gcccttcgcc      5100
tgggacatcc tgtcccctca gttcatgtac ggctccaagg cctacgtgaa gcaccccgcc      5160
gacatccccg actacttgaa gctgtccttc cccgagggct tcaagtggga gcgcgtgatg      5220
aacttcgagg acggcggcgt ggtgaccgtg acccaggact cctccctgca ggacggcgag      5280
ttcatctaca aggtgaagct gcgcggcacc aacttcccct ccgacggccc cgtaatgcag      5340
aagaagacca tgggctggga ggcctcctcc gagcggatgt accccgagga cggcgccctg      5400
aagggcgaga tcaagcagag gctgaagctg aaggacggcg gccactacga cgctgaggtc      5460
aagaccacct acaaggccaa gaagcccgtg cagctgcccg gcgcctacaa cgtcaacatc      5520
aagttggaca tcacctccca caacgaggac tacaccatcg tggaacagta cgaacgcgcc      5580
gagggccgcc actccaccgg cggcatggac gagctgtaca gtaatgagaa attcgatatc      5640
aagcttatcg ataatcaacc tctggattac aaaatttgtg aaagattgac tggtattctt      5700
aactatgttg ctccttttac gctatgtgga tacgctgctt taatgccttt gtatcatgct      5760
attgcttccc gtatggcttt cattttctcc tccttgtata atcctggtt gctgtctctt      5820 tatgaggagt tgtggcccgt tgtcaggcaa cgtggcgtgg tgtgcactgt gtttgctgac      5880 gcaacccccca ctggttgggg cattgccacc acctgtcagc tcctttccgg gactttcgct      5940 ttcccccctcc ctattgccac ggcggaactc atcgccgcct gccttgcccg ctgctggaca      6000
ggggctcggc tgttgggcac tgacaattcc gtggtgttgt cggggaaatc atcgtccttt      6060
ccttggctgc tcgcctatgt tgccacctgg attctgcgcg ggacgtcctt ctgctacgtc      6120
ccttcggccc tcaatccagc ggaccttcct tcccgcggcc tgctgccggc tctgcggcct      6180
cttccgcgtc ttcgccttcg ccctcagacg agtcggatct cccttttgggc cgcctccccg      6240 catcgatacc gagcgctgct cgagagatct acgggtggca tccctgtgac ccctccccag      6300
tgcctctcct ggccctggaa gttgccactc cagtgcccac cagccttgtc ctaataaaat      6360
taagttgcat cattttgtct gactaggtgt ccttctataa tattatgggg tggaggggggg      6420 tggtatggag caagggcaa gttgggaaga caacctgtag ggcctgcggg gtctattggg      6480
aaccaagctg gagtgcagtg gcacaatctt ggctcactgc aatctccgcc tcctgggttc      6540
aagcgattct cctgcctcag cctcccgagt tgttgggatt ccaggcatgc atgaccaggc      6600
tcagctaatt tttgtttttt tggtagagac ggggtttcac catattggcc aggctggtct      6660
```

-continued

```
ccaactccta atctcaggtg atctacccac cttggcctcc caaattgctg ggattacagg    6720
cgtgaaccac tgctcccttc cctgtccttc tgattttgta ggtaaccacg tgcggaccga    6780
gcggccgcag gaacccctag tgatggagtt ggccactccc tctctgcgcg ctcgctcgct    6840
cactgaggcc gggcgaccaa aggtcgcccg acgcccgggc tttgcccggg cggcctcagt    6900
gagcgagcga gcgcgcagct gcctgcagg                                      6929
```

```
<210> SEQ ID NO 12
<211> LENGTH: 14
<212> TYPE: PRT
<213> ORGANISM: Mus musculus

<400> SEQUENCE: 12

Ser Gly Phe Ala Asn Glu Leu Gly Pro Arg Leu Met Gly Lys
1               5                   10

<210> SEQ ID NO 13
<211> LENGTH: 24
<212> TYPE: PRT
<213> ORGANISM: Mus musculus

<400> SEQUENCE: 13

Leu Glu Gly Arg Gly Ser Leu Leu Thr Cys Gly Asp Val Glu Glu Asn
1               5                   10                  15

Pro Gly Pro Ala Pro Gly Ser Thr
            20
```